US010918420B2

(12) United States Patent
Jackson et al.

(10) Patent No.: US 10,918,420 B2
(45) Date of Patent: *Feb. 16, 2021

(54) PIVOTAL BONE ANCHOR ASSEMBLY WITH FORCED DOWNWARD DISPLACEMENT OF A COMPRESSION INSERT BY A TOOL

(71) Applicant: Roger P. Jackson, Prairie Village, KS (US)

(72) Inventors: Roger P. Jackson, Prairie Village, KS (US); James L. Surber, Kansas City, KS (US)

(73) Assignee: Roger P. Jackson, Prairie Village, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/363,195

(22) Filed: Mar. 25, 2019

(65) Prior Publication Data
US 2019/0216511 A1    Jul. 18, 2019

Related U.S. Application Data

(63) Continuation of application No. 15/638,039, filed on Jun. 29, 2017, now Pat. No. 10,238,431, which is a continuation of application No. 14/872,621, filed on Oct. 1, 2015, now Pat. No. 9,717,534, which is a continuation of application No. 13/573,303, filed on Sep. 7, 2012, now Pat. No. 9,393,047, and a continuation-in-part of application No. 13/506,365,
(Continued)

(51) Int. Cl.
*A61B 17/70* (2006.01)
*A61B 17/86* (2006.01)

(52) U.S. Cl.
CPC ...... *A61B 17/7037* (2013.01); *A61B 17/7005* (2013.01); *A61B 17/7007* (2013.01); *A61B 17/7053* (2013.01); *A61B 17/8605* (2013.01); *A61B 17/701* (2013.01); *A61B 17/702* (2013.01); *A61B 17/7008* (2013.01); *A61B 17/7031* (2013.01); *A61B 17/7032* (2013.01); *A61B 17/7035* (2013.01); *A61B 17/7043* (2013.01)

(58) Field of Classification Search
CPC ............ A61B 17/7035; A61B 17/7037; A61B 17/7038
See application file for complete search history.

(56) References Cited

U.S. PATENT DOCUMENTS

| 5,501,684 A | 3/1996 | Schlapfer |
| 5,584,834 A | 12/1996 | Errico et al. |

(Continued)

*Primary Examiner* — Nicholas W Woodall
(74) *Attorney, Agent, or Firm* — Polsinelli PC

(57) ABSTRACT

A polyaxial bone screw assembly includes a threaded shank body having an integral upper portion receivable in an integral receiver, the receiver having an upper channel for receiving a longitudinal connecting member and a lower cavity cooperating with a lower opening. A down-loadable compression insert, a down-loadable friction fit split retaining ring having inner and outer tangs and an up-loadable shank upper portion cooperate to provide for pop- or snap-on assembly of the shank with the receiver either prior to or after implantation of the shank into a vertebra. The shank and receiver once assembled cannot be disassembled.

17 Claims, 40 Drawing Sheets

Related U.S. Application Data filed on Apr. 13, 2012, now Pat. No. 8,444,681, and a continuation-in-part of application No. 13/385,212, filed on Feb. 8, 2012, now Pat. No. 9,216,041, and a continuation-in-part of application No. 13/374,439, filed on Dec. 29, 2011, now Pat. No. 9,980,753, and a continuation-in-part of application No. 13/373,289, filed on Nov. 9, 2011, now Pat. No. 9,907,574, and a continuation-in-part of application No. 13/136,331, filed on Jul. 28, 2011, now abandoned, and a continuation-in-part of application No. 12/924,802, filed on Oct. 5, 2010, now Pat. No. 8,556,938, and a continuation-in-part of application No. 12/802,849, filed on Jun. 15, 2010, now abandoned.

(60) Provisional application No. 61/573,508, filed on Sep. 7, 2011, provisional application No. 61/517,088, filed on Apr. 13, 2011, provisional application No. 61/463,037, filed on Feb. 11, 2011, provisional application No. 61/460,267, filed on Dec. 29, 2010, provisional application No. 61/460,234, filed on Dec. 29, 2010, provisional application No. 61/456,649, filed on Nov. 10, 2010, provisional application No. 61/403,915, filed on Sep. 23, 2010, provisional application No. 61/400,504, filed on Jul. 29, 2010, provisional application No. 61/403,696, filed on Sep. 20, 2010, provisional application No. 61/402,959, filed on Sep. 8, 2010, provisional application No. 61/398,807, filed on Jul. 1, 2010, provisional application No. 61/396,390, filed on May 26, 2010, provisional application No. 61/395,752, filed on May 17, 2010, provisional application No. 61/395,564, filed on May 14, 2010, provisional application No. 61/343,737, filed on May 3, 2010, provisional application No. 61/336,911, filed on Jan. 28, 2010, provisional application No. 61/278,240, filed on Oct. 5, 2009, provisional application No. 61/270,754, filed on Jul. 13, 2009, provisional application No. 61/268,708, filed on Jun. 15, 2009.

(56) References Cited

U.S. PATENT DOCUMENTS

| | | |
|---|---|---|
| 5,672,176 A | 9/1997 | Biedermann et al. |
| 5,735,853 A | 4/1998 | Olerud |
| 5,891,145 A | 4/1999 | Morrison et al. |
| 6,063,090 A | 5/2000 | Schlapfer |
| 6,146,383 A | 11/2000 | Studer et al. |
| 6,241,731 B1 | 6/2001 | Fiz |
| 6,280,442 B1 | 8/2001 | Barker et al. |
| 6,626,908 B2 | 9/2003 | Cooper et al. |
| 6,648,888 B1 | 11/2003 | Shluzas |
| 6,660,004 B2 | 12/2003 | Barker et al. |
| 6,716,214 B1 | 4/2004 | Jackson |
| 6,740,086 B2 | 5/2004 | Richelsoph |
| 6,837,889 B2 * | 1/2005 | Shluzas ............ A61B 17/7037 606/267 |
| 7,001,389 B1 | 2/2006 | Navarro et al. |
| 7,066,937 B2 | 6/2006 | Shluzas |
| 7,087,057 B2 | 8/2006 | Konieczynski et al. |
| 7,160,300 B2 | 1/2007 | Jackson |
| 7,179,261 B2 | 2/2007 | Sicvol et al. |
| 7,186,255 B2 | 3/2007 | Baynham |
| 7,306,606 B2 | 12/2007 | Sasing |
| 7,322,981 B2 | 1/2008 | Jackson |
| 7,377,923 B2 | 5/2008 | Purcell et al. |
| 7,491,218 B2 | 2/2009 | Landry et al. |
| 7,530,992 B2 | 5/2009 | Biedermann et al. |
| 7,618,444 B2 | 11/2009 | Shluzas |
| 7,625,396 B2 | 12/2009 | Jackson |
| 7,686,835 B2 | 3/2010 | Warnick |
| 7,766,945 B2 | 8/2010 | Nilsson et al. |
| 7,776,067 B2 | 8/2010 | Jackson |
| 7,833,251 B1 | 11/2010 | Ahlgren et al. |
| 7,857,834 B2 | 12/2010 | Boschert |
| 7,875,065 B2 | 1/2011 | Jackson |
| 7,922,748 B2 | 4/2011 | Hoffman |
| 7,947,065 B2 | 5/2011 | Hammill et al. |
| 8,021,397 B2 | 9/2011 | Farris et al. |
| 8,034,089 B2 | 10/2011 | Matthis et al. |
| 8,048,112 B2 | 11/2011 | Suziki et al. |
| 8,048,126 B2 | 11/2011 | Altarac et al. |
| 8,066,744 B2 | 11/2011 | Justis et al. |
| 8,100,946 B2 | 1/2012 | Strasbaugh et al. |
| 8,133,262 B2 | 3/2012 | Whipple |
| 8,137,386 B2 | 3/2012 | Jackson |
| 8,206,422 B2 | 6/2012 | Hestad et al. |
| 8,277,485 B2 | 10/2012 | Krishna et al. |
| 8,361,129 B2 | 1/2013 | Chao |
| 8,377,102 B2 | 2/2013 | Jackson |
| 8,430,914 B2 | 4/2013 | Spratt et al. |
| 8,444,681 B2 | 5/2013 | Jackson et al. |
| 8,449,578 B2 | 5/2013 | Keiser et al. |
| 8,506,609 B2 | 8/2013 | Biedermann et al. |
| 8,591,558 B2 | 11/2013 | Matthis et al. |
| 8,771,324 B2 | 7/2014 | Black |
| 8,814,913 B2 | 8/2014 | Jackson |
| 8,876,869 B1 | 11/2014 | Schafer et al. |
| 8,888,827 B2 | 11/2014 | Harper et al. |
| 8,986,349 B1 | 3/2015 | German |
| 9,155,567 B2 | 10/2015 | Auerbach et al. |
| 9,168,069 B2 | 10/2015 | Jackson |
| 9,198,694 B2 | 12/2015 | Mishra et al. |
| 9,393,047 B2 | 9/2016 | Jackson et al. |
| 9,439,681 B2 | 9/2016 | Keyer et al. |
| 9,456,853 B2 | 10/2016 | Jackson |
| 9,480,517 B2 | 11/2016 | Jackson et al. |
| 9,504,496 B2 | 11/2016 | Jackson et al. |
| 9,572,599 B1 | 2/2017 | Casey et al. |
| 9,700,354 B2 | 7/2017 | Jackson |
| 9,717,534 B2 | 8/2017 | Jackson et al. |
| 9,801,665 B2 | 10/2017 | Jackson |
| 9,883,892 B2 | 2/2018 | Jackson et al. |
| 9,895,172 B2 | 2/2018 | Biedermann et al. |
| 9,907,574 B2 | 3/2018 | Jackson et al. |
| 9,918,745 B2 | 3/2018 | Jackson |
| 9,956,006 B2 | 5/2018 | Jackson |
| 9,980,743 B2 | 5/2018 | Jackson et al. |
| 9,980,753 B2 | 5/2018 | Jackson |
| 10,085,774 B2 | 10/2018 | Jackson |
| 10,172,649 B2 | 1/2019 | Jackson et al. |
| 10,179,010 B2 | 1/2019 | Jackson et al. |
| 10,456,173 B1 | 10/2019 | Casey et al. |
| 10,478,225 B2 | 11/2019 | Jackson et al. |
| 2002/0022842 A1 | 2/2002 | Horvath et al. |
| 2002/0026193 A1 | 2/2002 | Barker et al. |
| 2002/0133159 A1 | 9/2002 | Jackson |
| 2002/0143341 A1 | 10/2002 | Biedermann et al. |
| 2002/0193794 A1 | 12/2002 | Taylor |
| 2004/0039383 A1 | 2/2004 | Jackson |
| 2004/0049196 A1 | 3/2004 | Jackson |
| 2004/0167526 A1 | 8/2004 | Jackson |
| 2004/0267264 A1 | 12/2004 | Konieczynski et al. |
| 2005/0080415 A1 | 4/2005 | Keyer et al. |
| 2005/0187548 A1 | 8/2005 | Butler et al. |
| 2005/0228379 A1 | 10/2005 | Jackson |
| 2005/0240180 A1 | 10/2005 | Vienney |
| 2006/0025771 A1 | 2/2006 | Jackson |
| 2006/0036252 A1 | 2/2006 | Baynham et al. |
| 2006/0155277 A1 | 7/2006 | Metz-Stavenhagen |
| 2006/0173454 A1 | 8/2006 | Spitler et al. |
| 2006/0200131 A1 | 9/2006 | Chao et al. |
| 2006/0217716 A1 | 9/2006 | Baker |
| 2006/0293664 A1 | 12/2006 | Schumacher |
| 2007/0088357 A1 | 4/2007 | Johnson et al. |
| 2007/0090238 A1 | 4/2007 | Justis |
| 2007/0093826 A1 | 4/2007 | Hawkes et al. |
| 2007/0093827 A1 | 4/2007 | Warnick |

(56) References Cited

U.S. PATENT DOCUMENTS

| | | |
|---|---|---|
| 2007/0118117 A1 | 5/2007 | Altarac et al. |
| 2007/0118123 A1* | 5/2007 | Strausbaugh ...... A61B 17/7038 606/272 |
| 2007/0123862 A1 | 5/2007 | Warnick |
| 2007/0161999 A1 | 7/2007 | Biedermann et al. |
| 2007/0233087 A1 | 10/2007 | Schlapfer |
| 2007/0270813 A1 | 11/2007 | Garamszegi |
| 2007/0270831 A1 | 11/2007 | Dewey et al. |
| 2008/0045953 A1 | 2/2008 | Garamszegi |
| 2008/0086132 A1 | 4/2008 | Biedermann et al. |
| 2008/0132957 A1 | 6/2008 | Matthis et al. |
| 2008/0140135 A1 | 6/2008 | Konieczynski et al. |
| 2008/0140136 A1 | 6/2008 | Jackson |
| 2008/0147129 A1 | 6/2008 | Biedermann et al. |
| 2008/0154315 A1 | 6/2008 | Jackson |
| 2008/0161863 A1 | 7/2008 | Arnold et al. |
| 2008/0215100 A1 | 9/2008 | Matthis et al. |
| 2008/0221681 A1 | 9/2008 | Trieu et al. |
| 2008/0234761 A1 | 9/2008 | Jackson |
| 2008/0269809 A1 | 10/2008 | Garamszegi |
| 2008/0294202 A1 | 11/2008 | Peterson et al. |
| 2008/0319490 A1 | 12/2008 | Jackson |
| 2009/0012567 A1 | 1/2009 | Biedermann et al. |
| 2009/0062866 A1 | 3/2009 | Jackson |
| 2009/0062867 A1 | 3/2009 | Schumacher |
| 2009/0069852 A1 | 3/2009 | Farris et al. |
| 2009/0069853 A1 | 3/2009 | Schumacher |
| 2009/0105769 A1 | 4/2009 | Rock et al. |
| 2009/0105770 A1 | 4/2009 | Berrevoets et al. |
| 2009/0204155 A1 | 8/2009 | Aschmann |
| 2009/0240290 A1 | 9/2009 | Choi |
| 2010/0023061 A1 | 1/2010 | Randol et al. |
| 2010/0087865 A1 | 4/2010 | Biedermann et al. |
| 2010/0094343 A1 | 4/2010 | Pham et al. |
| 2010/0094349 A1 | 4/2010 | Hammer et al. |
| 2010/0100137 A1 | 4/2010 | Justis et al. |
| 2010/0114170 A1 | 5/2010 | Barrus et al. |
| 2010/0152787 A1 | 6/2010 | Walsh et al. |
| 2010/0198272 A1 | 8/2010 | Keyer et al. |
| 2010/0234902 A1 | 9/2010 | Biedermann et al. |
| 2010/0256686 A1 | 10/2010 | Fisher |
| 2010/0262195 A1 | 10/2010 | Jackson |
| 2010/0274288 A1 | 10/2010 | Prevost et al. |
| 2010/0305621 A1 | 12/2010 | Wang et al. |
| 2011/0040338 A1 | 2/2011 | Jackson |
| 2011/0077694 A1 | 3/2011 | Biedermann et al. |
| 2011/0152949 A1 | 6/2011 | Biedermann et al. |
| 2011/0160778 A1 | 6/2011 | Elsbury |
| 2011/0196430 A1 | 8/2011 | Walsh et al. |
| 2011/0213424 A1 | 9/2011 | Biedermann et al. |
| 2011/0282399 A1 | 11/2011 | Jackson |
| 2012/0010661 A1 | 1/2012 | Farris et al. |
| 2012/0035670 A1 | 2/2012 | Jackson et al. |
| 2012/0041490 A1 | 2/2012 | Jacob et al. |
| 2012/0046699 A1 | 2/2012 | Jones et al. |
| 2012/0046700 A1 | 2/2012 | Jackson et al. |
| 2012/0078307 A1 | 3/2012 | Nihalani |
| 2012/0165881 A1 | 6/2012 | Biedermann et al. |
| 2012/0165882 A1 | 6/2012 | Biedermann et al. |
| 2012/0179210 A1 | 7/2012 | Garamszegi |
| 2012/0179212 A1 | 7/2012 | Jackson et al. |
| 2012/0232598 A1 | 9/2012 | Hestad et al. |
| 2012/0265257 A1 | 10/2012 | Jackson |
| 2012/0303070 A1 | 11/2012 | Jackson |
| 2012/0310284 A1 | 12/2012 | Gerchow |
| 2012/0310290 A1 | 12/2012 | Jackson |
| 2013/0018428 A1 | 1/2013 | Harper et al. |
| 2013/0046345 A1 | 2/2013 | Jones et al. |
| 2013/0060292 A1 | 3/2013 | Jackson |
| 2013/0079830 A1 | 3/2013 | Garamszegi et al. |
| 2013/0103098 A1 | 4/2013 | Jackson et al. |
| 2013/0123861 A1 | 5/2013 | Biedermann et al. |
| 2013/0131730 A1 | 5/2013 | Jackson et al. |
| 2013/0144346 A1 | 6/2013 | Jackson et al. |
| 2013/0150852 A1 | 6/2013 | Shluzas et al. |
| 2013/0211465 A1* | 8/2013 | Savage ............... A61B 17/7037 606/308 |
| 2013/0268006 A1 | 10/2013 | Garamszegi |
| 2013/0345756 A1 | 12/2013 | Berrevoets et al. |
| 2014/0128927 A1 | 5/2014 | Jackson |
| 2014/0135854 A1 | 5/2014 | Dec et al. |
| 2014/0172018 A1 | 6/2014 | Gephart et al. |
| 2014/0172023 A1 | 6/2014 | Garamszegi |
| 2014/0188173 A1 | 7/2014 | Mishra et al. |
| 2014/0188175 A1 | 7/2014 | Mishra et al. |
| 2014/0303675 A1 | 10/2014 | Mishra |
| 2014/0379031 A1 | 12/2014 | Biedermann et al. |
| 2015/0182260 A1 | 7/2015 | Jackson et al. |
| 2015/0223844 A1 | 8/2015 | Leff et al. |
| 2015/0374413 A1 | 12/2015 | Spangler et al. |
| 2016/0045228 A1 | 2/2016 | Biedermann et al. |
| 2016/0220280 A1 | 8/2016 | Jackson |
| 2016/0302831 A1 | 10/2016 | Nichols et al. |
| 2016/0367293 A1 | 12/2016 | Keyer et al. |
| 2017/0119437 A1 | 5/2017 | Harper et al. |
| 2017/0128104 A1 | 5/2017 | Nichols et al. |
| 2017/0135729 A1 | 5/2017 | Garamszegi |
| 2017/0172627 A1 | 6/2017 | Kruger |
| 2017/0189074 A1 | 7/2017 | Biedermann et al. |
| 2017/0224386 A1 | 8/2017 | Leff et al. |
| 2017/0245897 A1 | 8/2017 | Nichols et al. |
| 2017/0265902 A1 | 9/2017 | Jackson |
| 2017/0296234 A1 | 10/2017 | Jackson et al. |
| 2017/0333086 A1 | 11/2017 | Jackson |
| 2017/0354443 A1 | 12/2017 | Jackson |
| 2018/0000523 A1 | 1/2018 | Jackson |
| 2018/0014859 A1 | 1/2018 | Biedermann et al. |
| 2018/0098795 A1 | 4/2018 | Jackson |
| 2018/0250036 A1 | 9/2018 | Jackson et al. |
| 2018/0263665 A1 | 9/2018 | Yacoub et al. |
| 2018/0325558 A1 | 11/2018 | Yacoub et al. |
| 2018/0325559 A1 | 11/2018 | Jackson |
| 2018/0325560 A1 | 11/2018 | Jackson et al. |
| 2019/0117271 A1 | 4/2019 | Jackson et al. |
| 2019/0247093 A1 | 8/2019 | Jackson et al. |
| 2019/0247094 A1 | 8/2019 | Yacoub et al. |
| 2019/0282278 A1 | 9/2019 | Schlapfer et al. |
| 2019/0307489 A1 | 10/2019 | Jackson et al. |
| 2019/0336174 A1 | 11/2019 | Jackson et al. |
| 2019/0357944 A1 | 11/2019 | Jackson et al. |
| 2019/0357945 A1 | 11/2019 | Jackson et al. |
| 2019/0365425 A1 | 12/2019 | Casey et al. |
| 2019/0365430 A1 | 12/2019 | Jackson et al. |
| 2020/0030004 A1 | 1/2020 | Jackson et al. |
| 2020/0030005 A1 | 1/2020 | Jackson et al. |
| 2020/0069337 A1 | 3/2020 | Jackson et al. |

\* cited by examiner

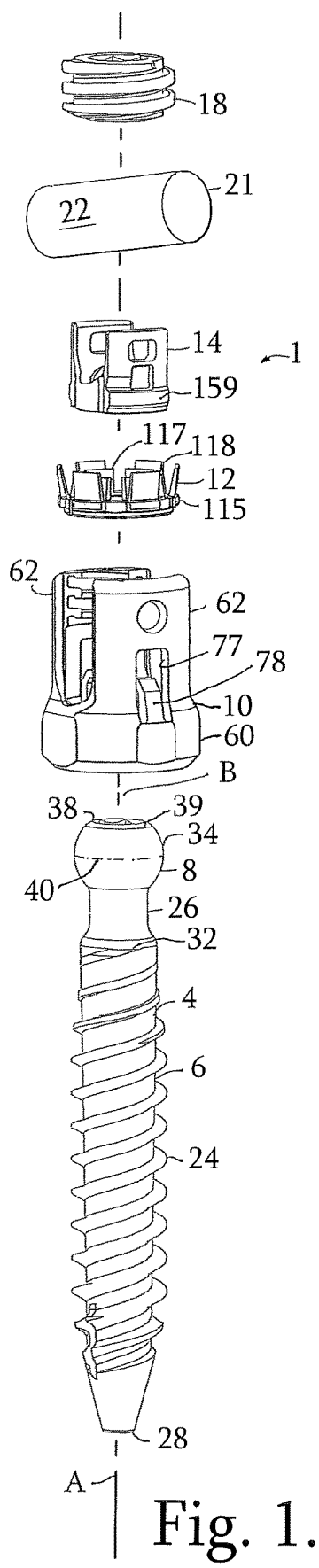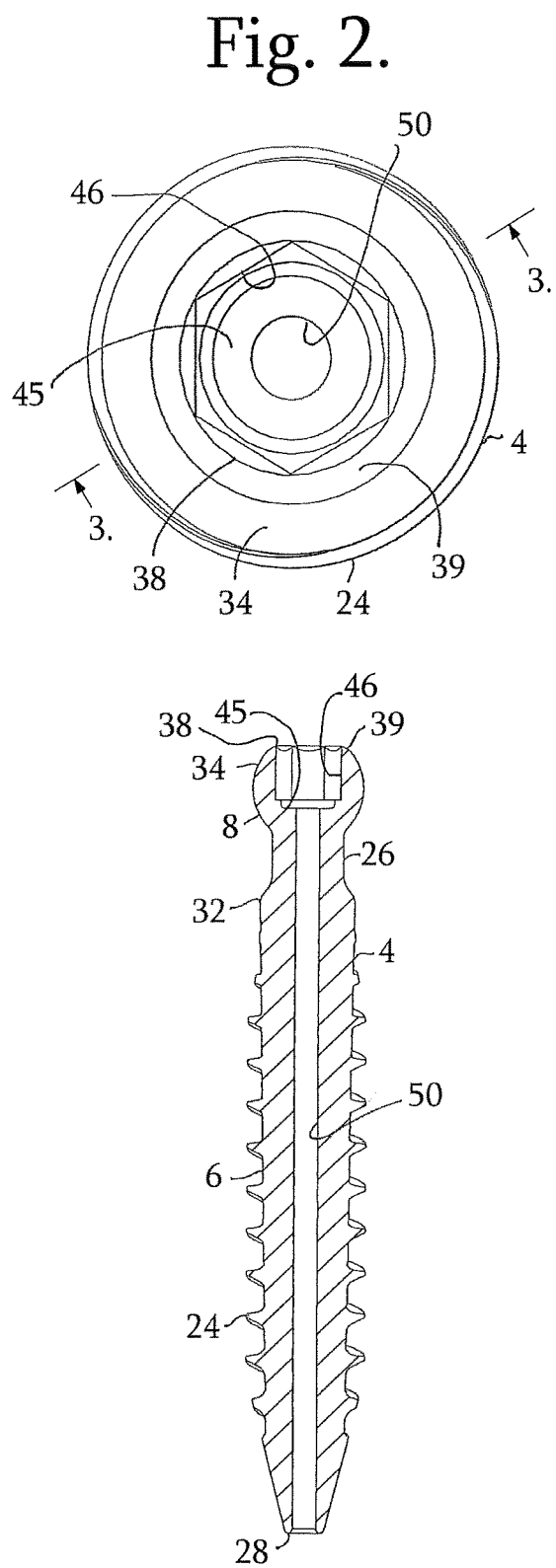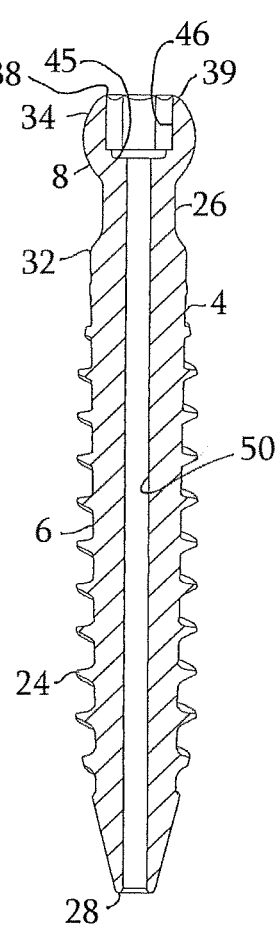

Fig. 15.
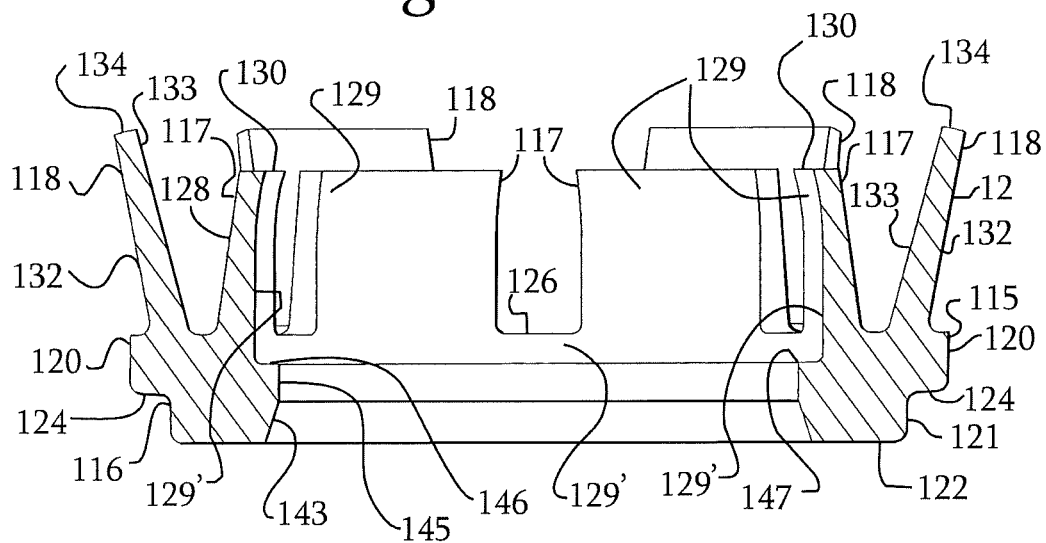
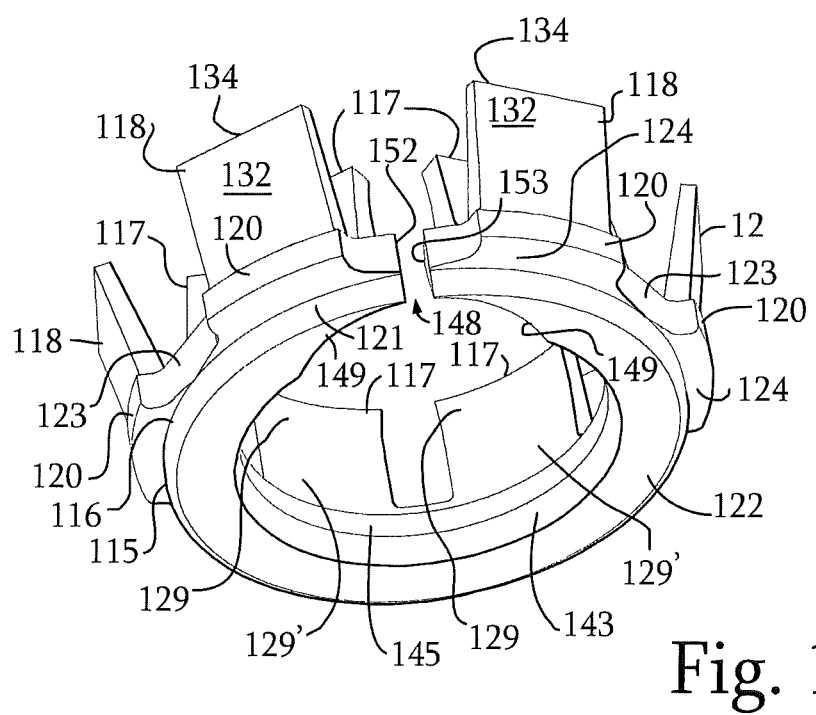
Fig. 16.

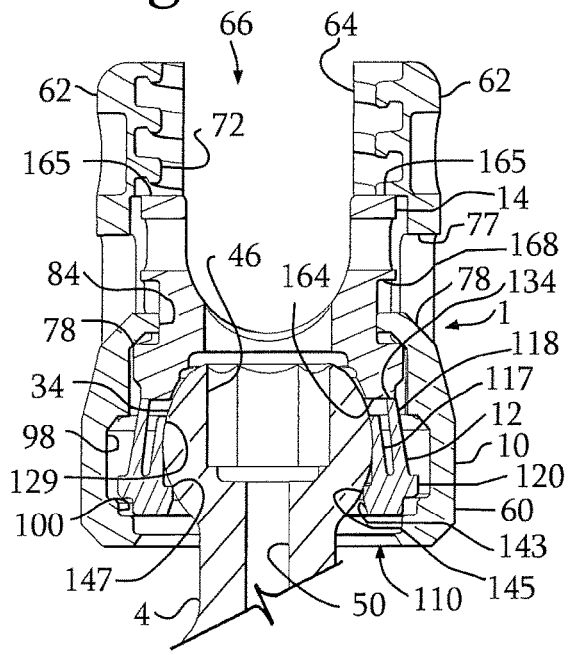
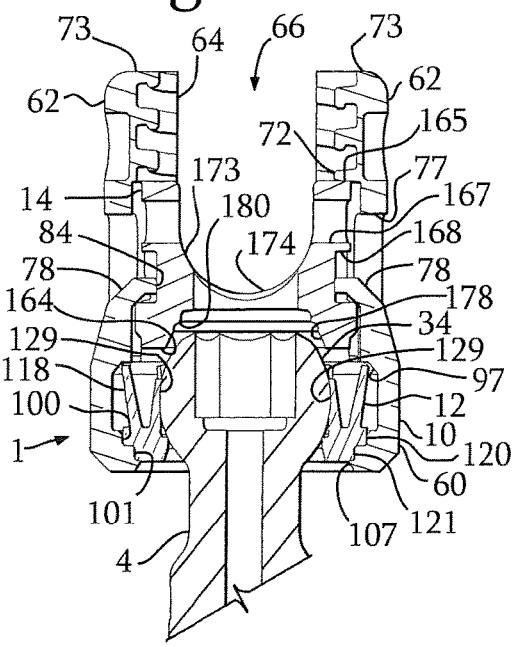
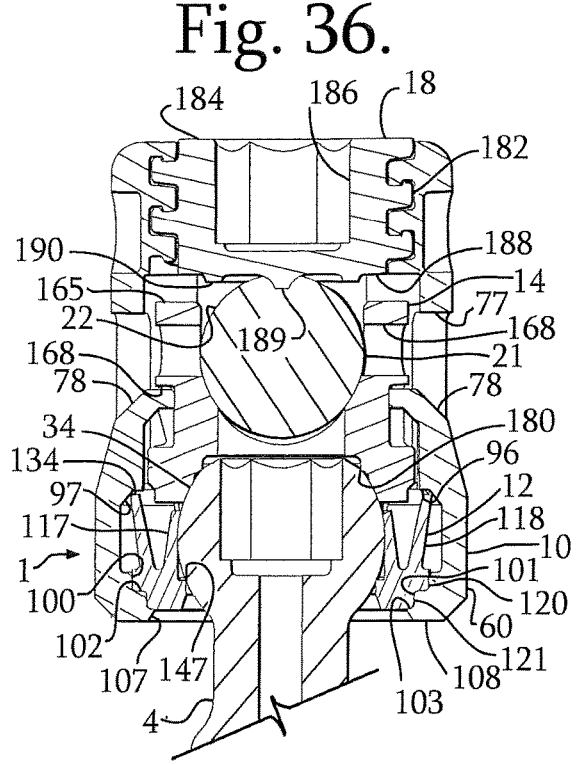
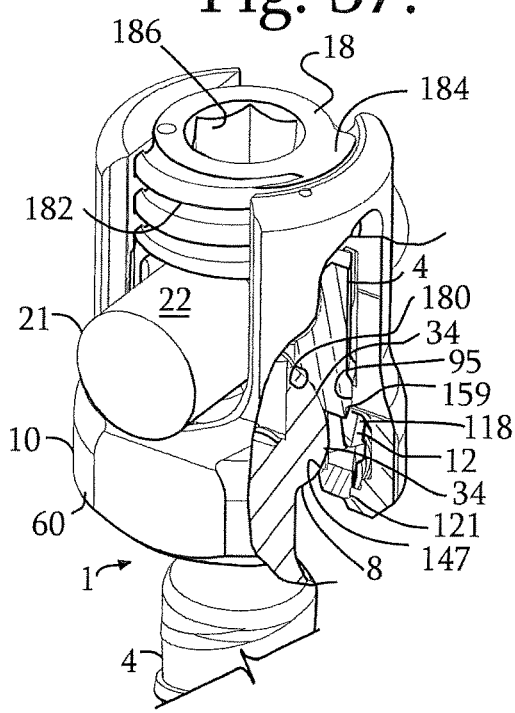

Fig. 38.
Fig. 39.
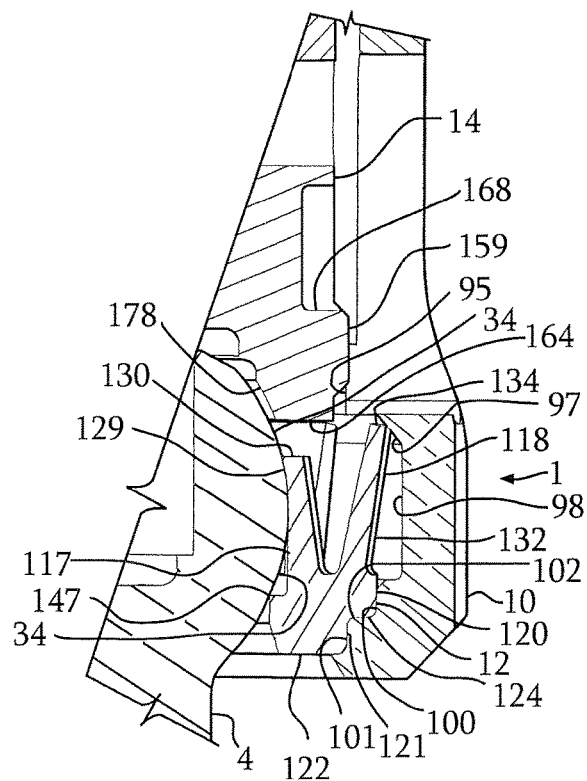
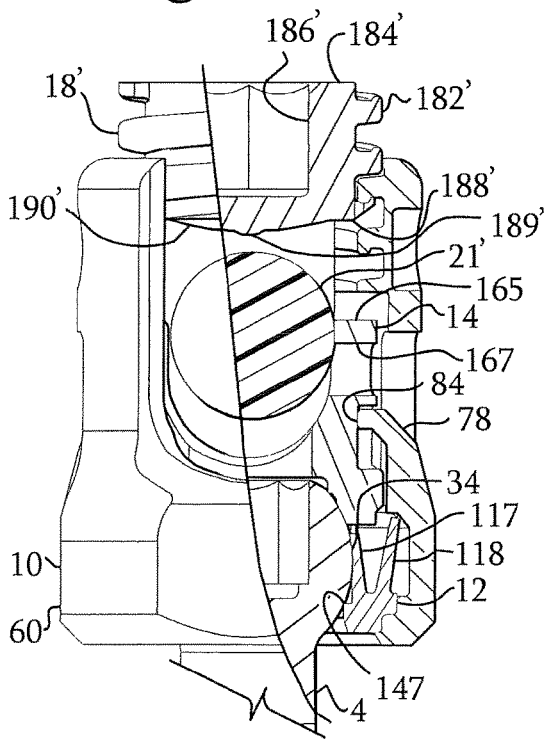
Fig. 40.

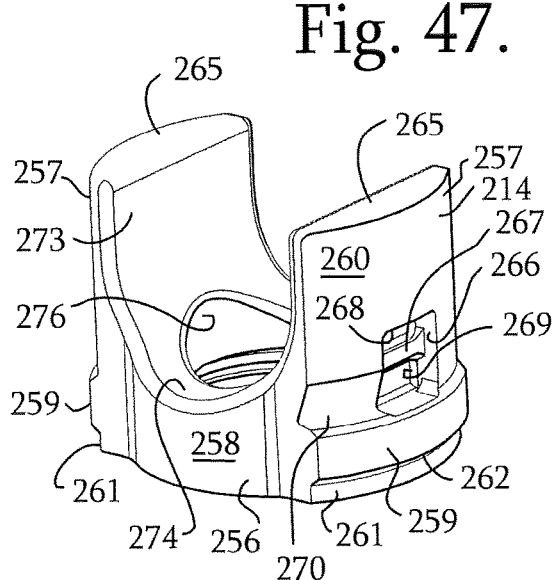
Fig. 47.
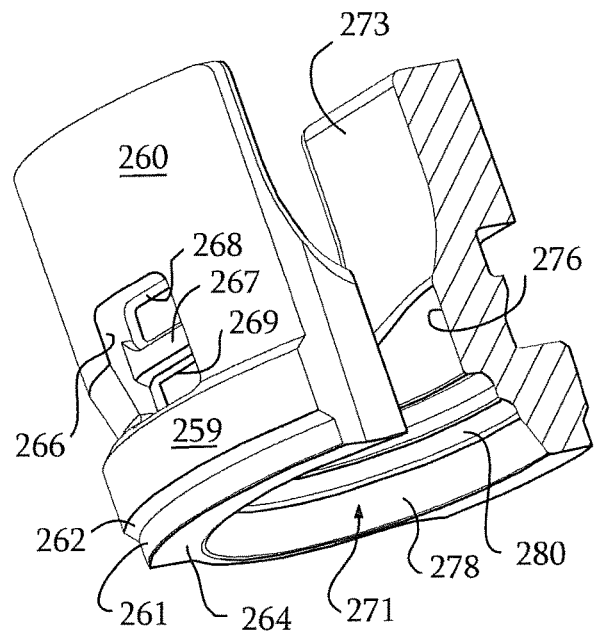
Fig. 48.
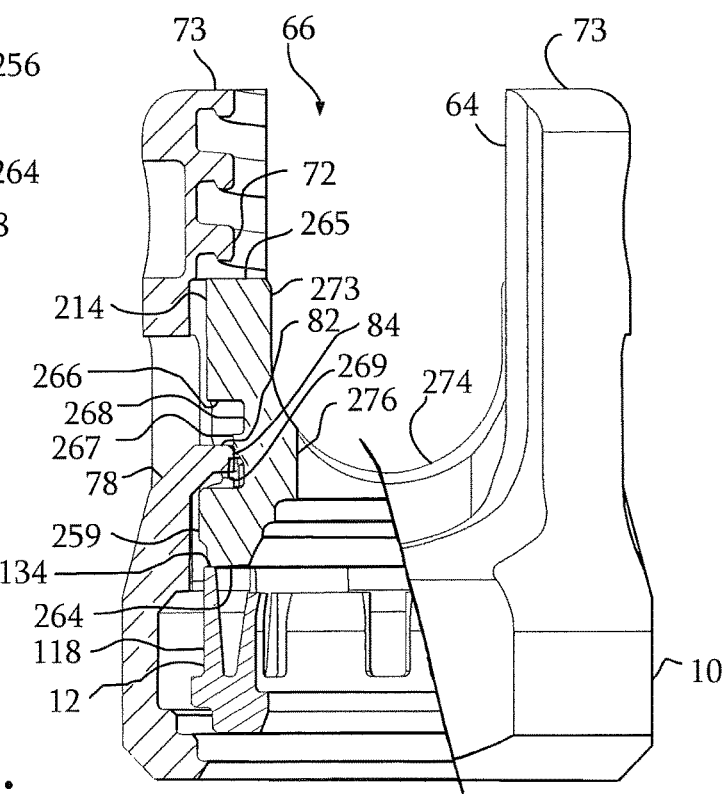
Fig. 49.
Fig. 50.

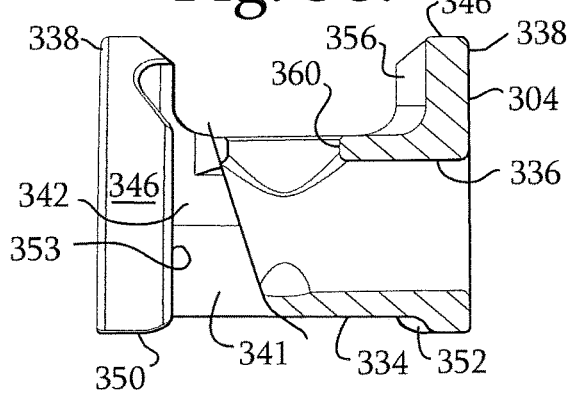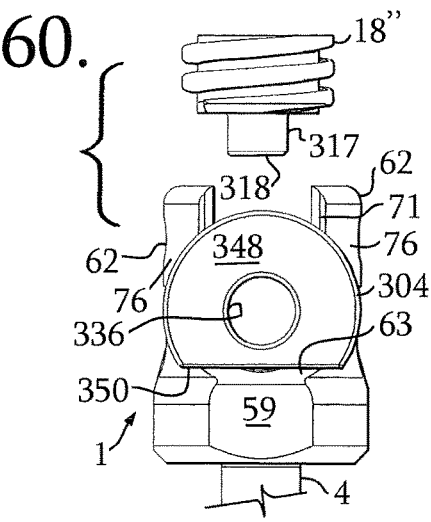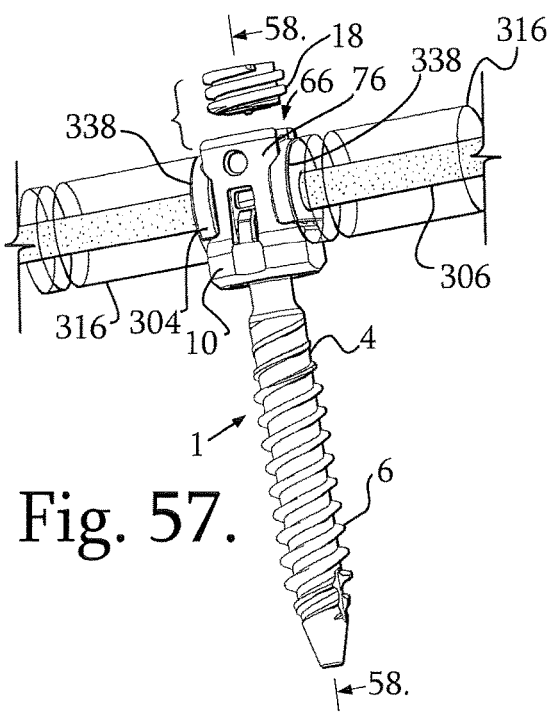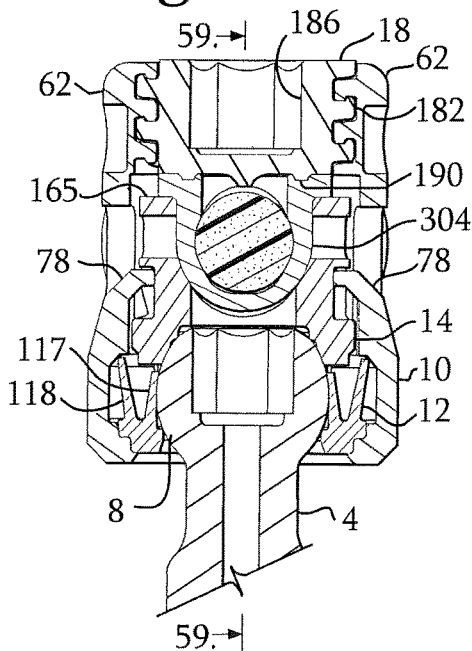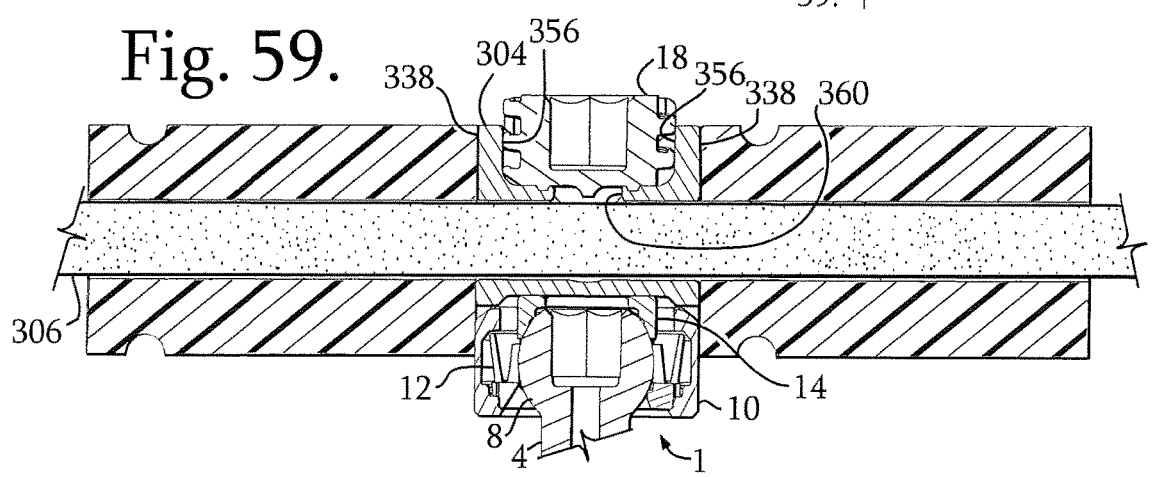

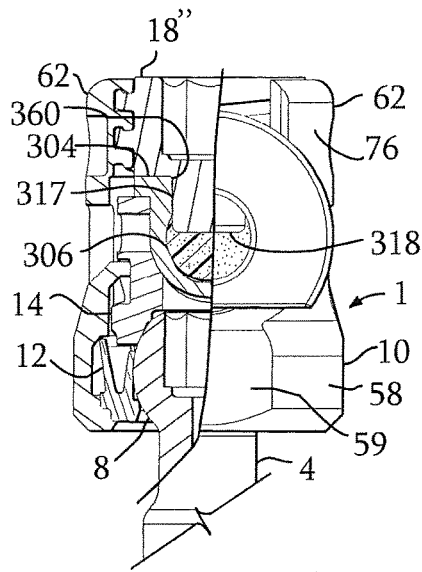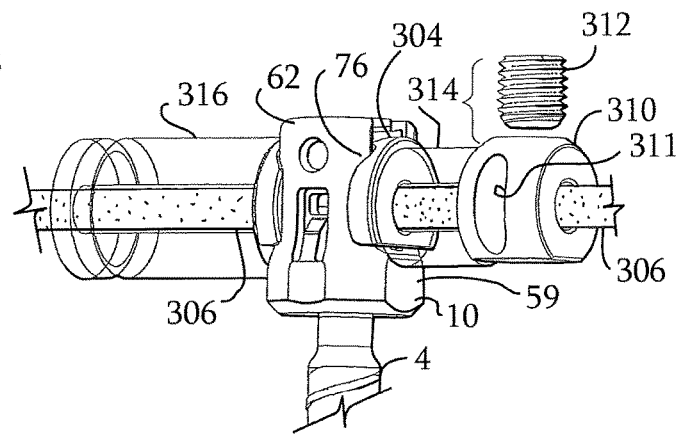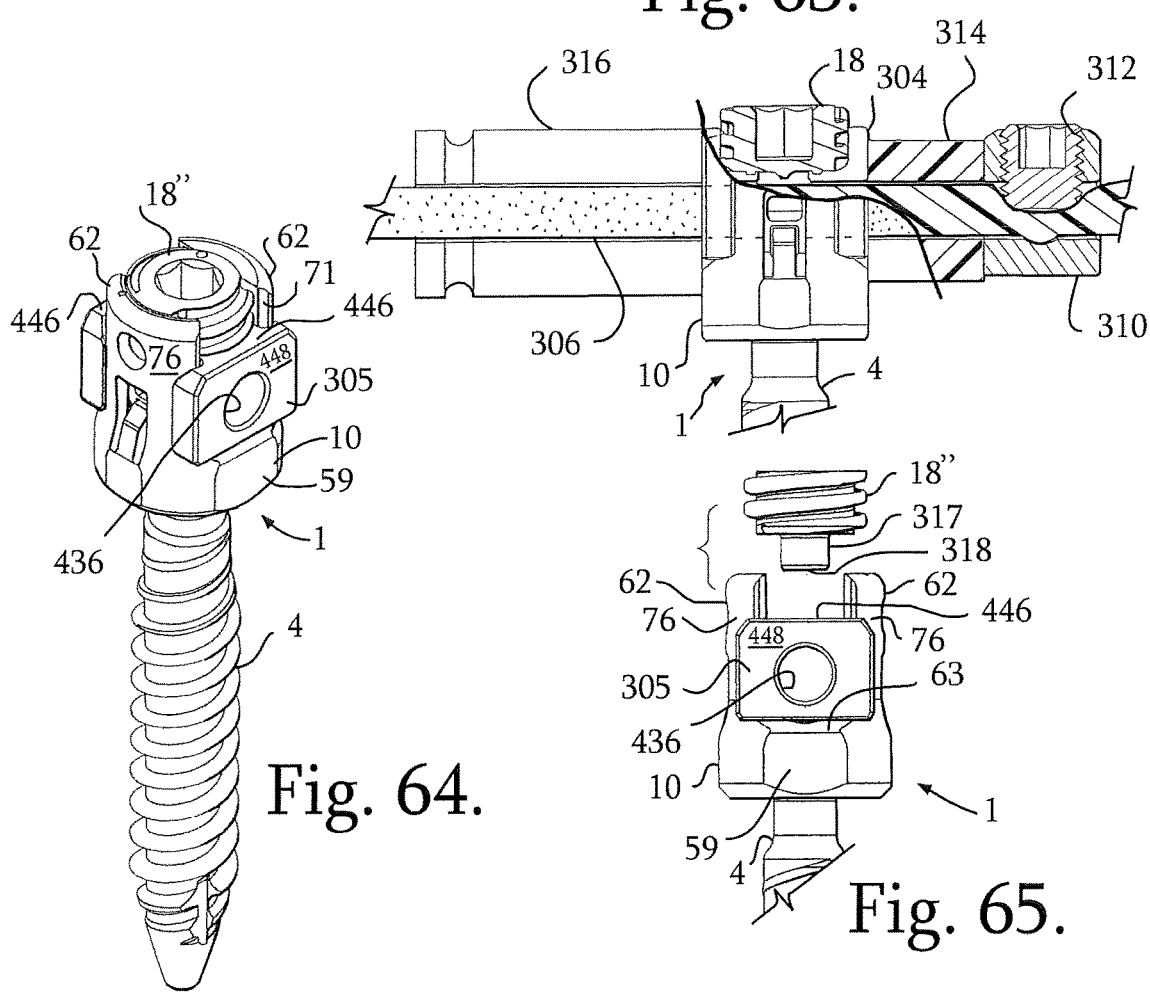
Fig. 61.
Fig. 62.
Fig. 63.
Fig. 64.
Fig. 65.

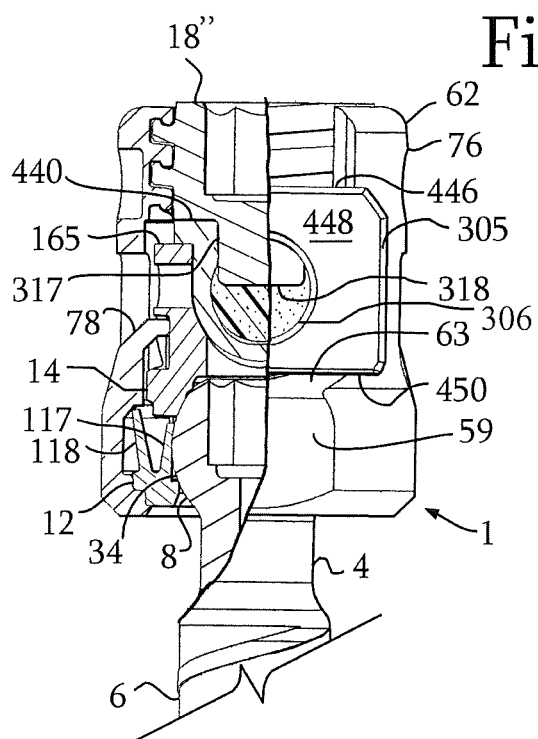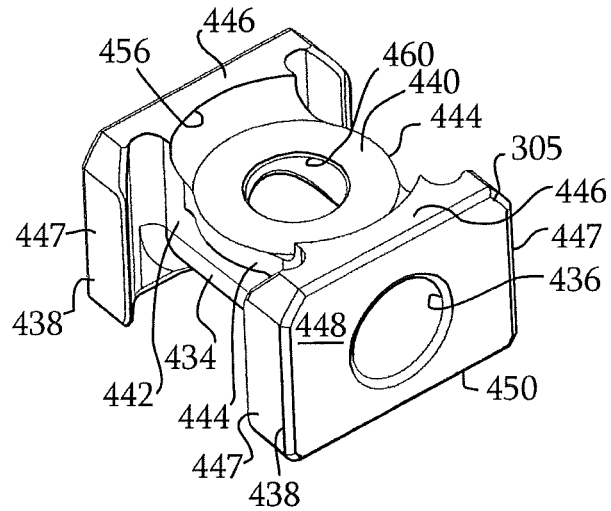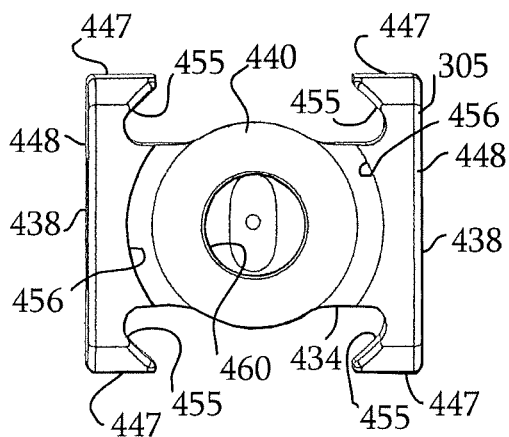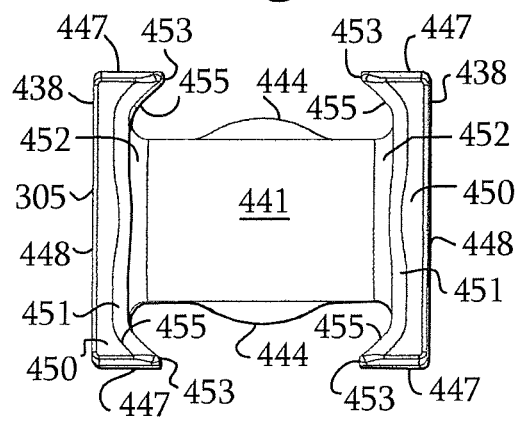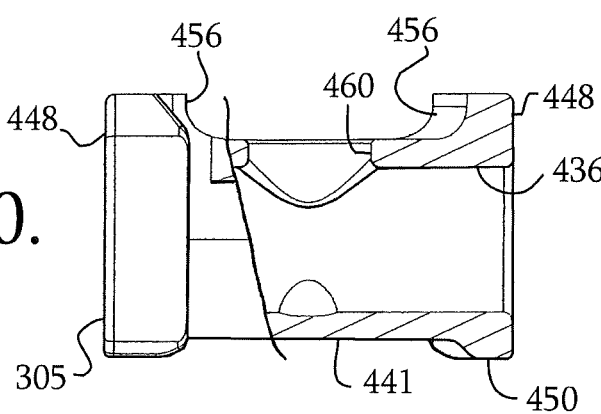

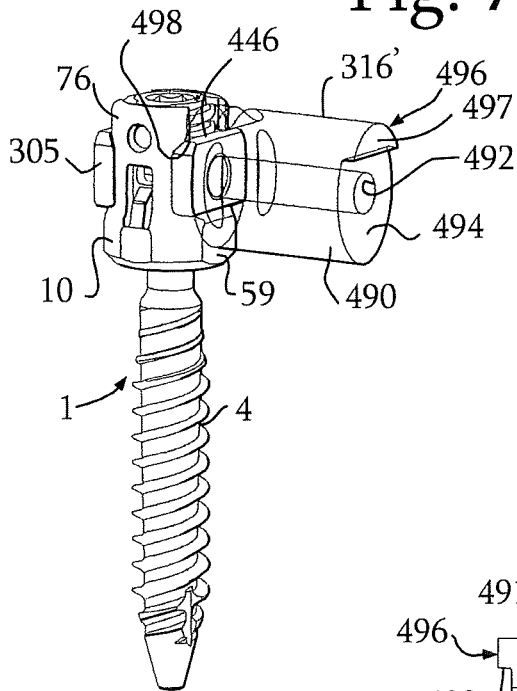
Fig. 71.
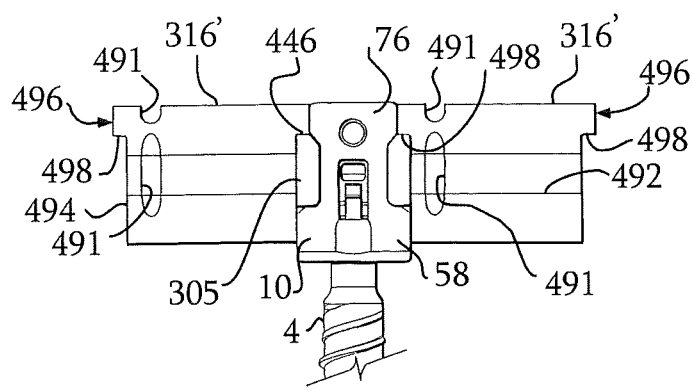
Fig. 72.
Fig. 73.
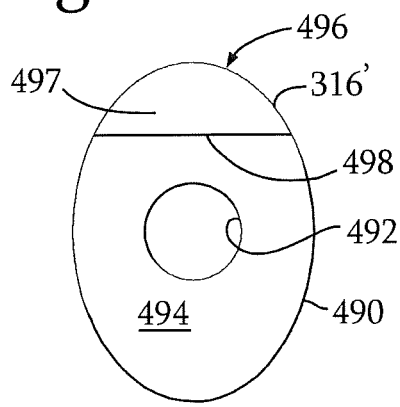
Fig. 74.
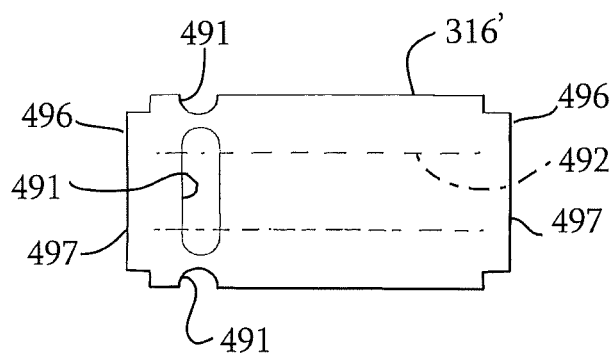

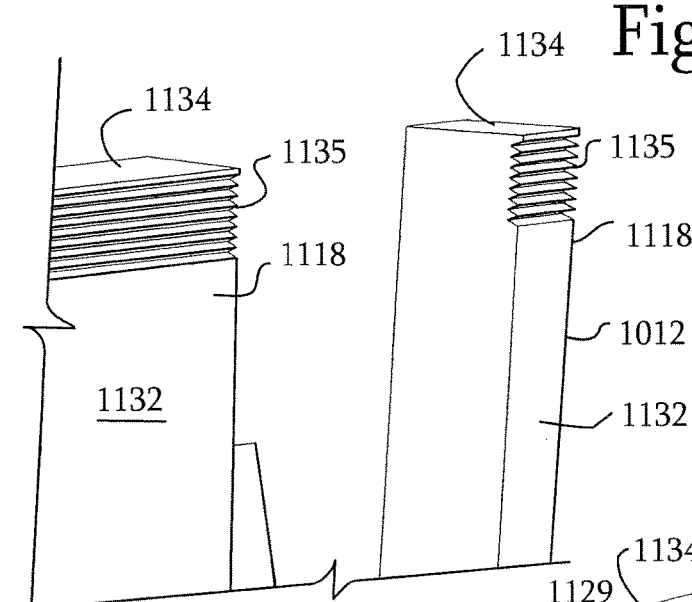
Fig. 81.
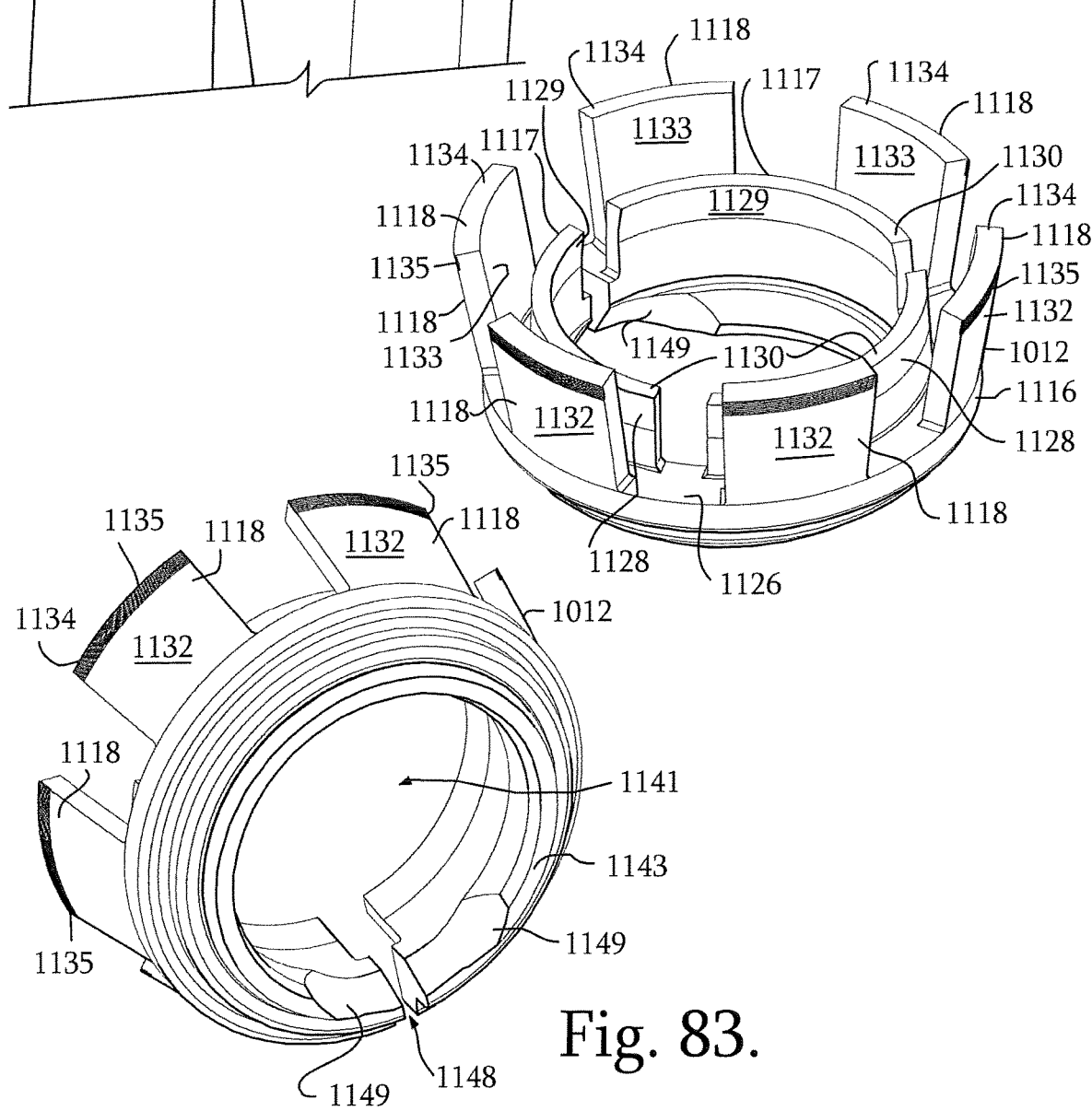
Fig. 82.
Fig. 83.

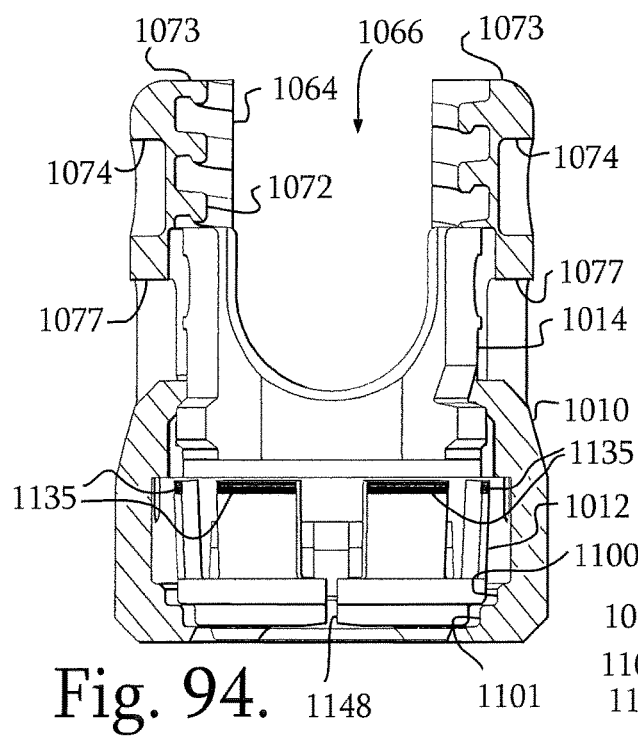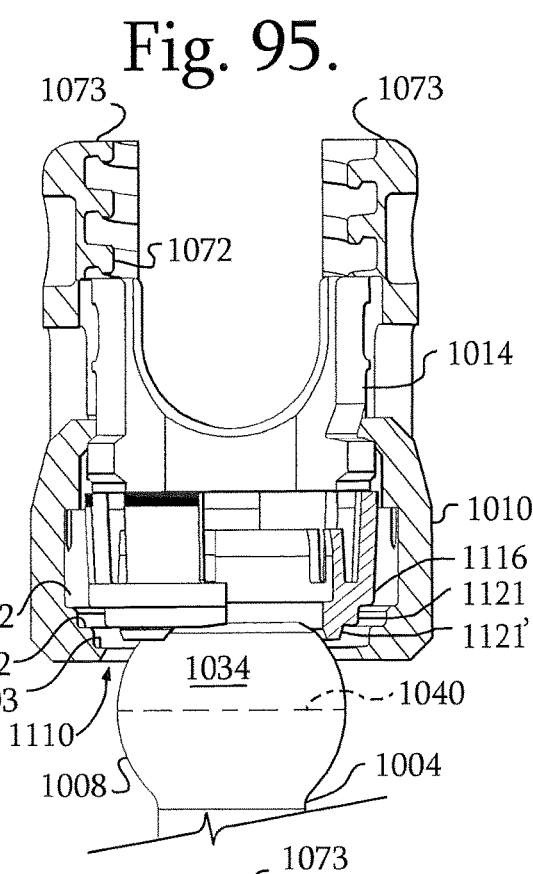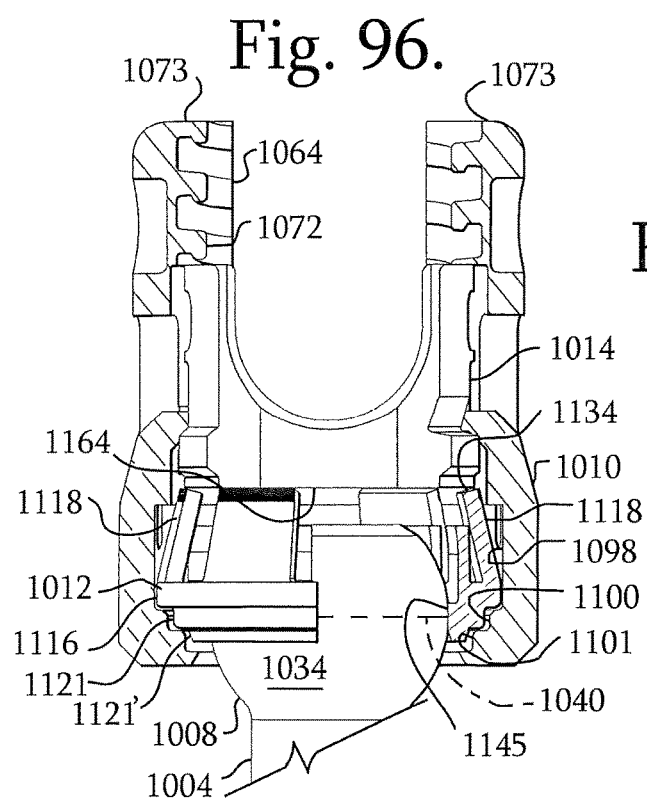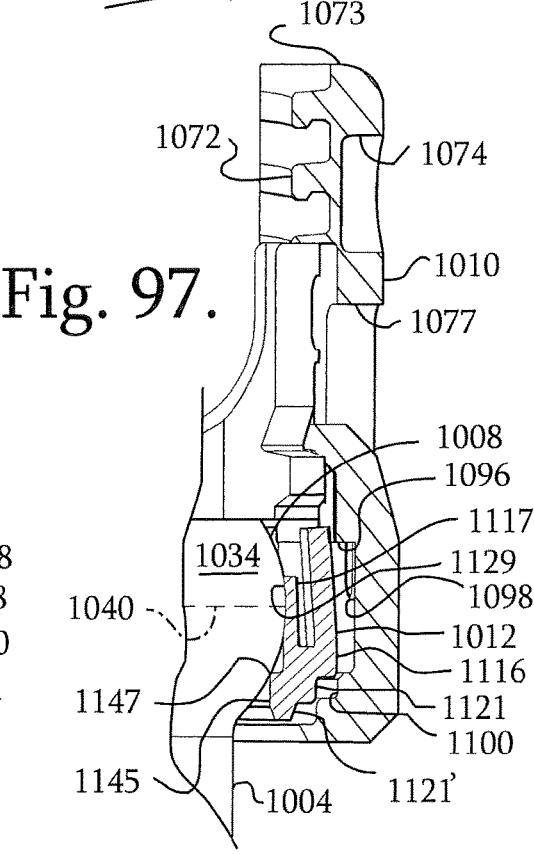

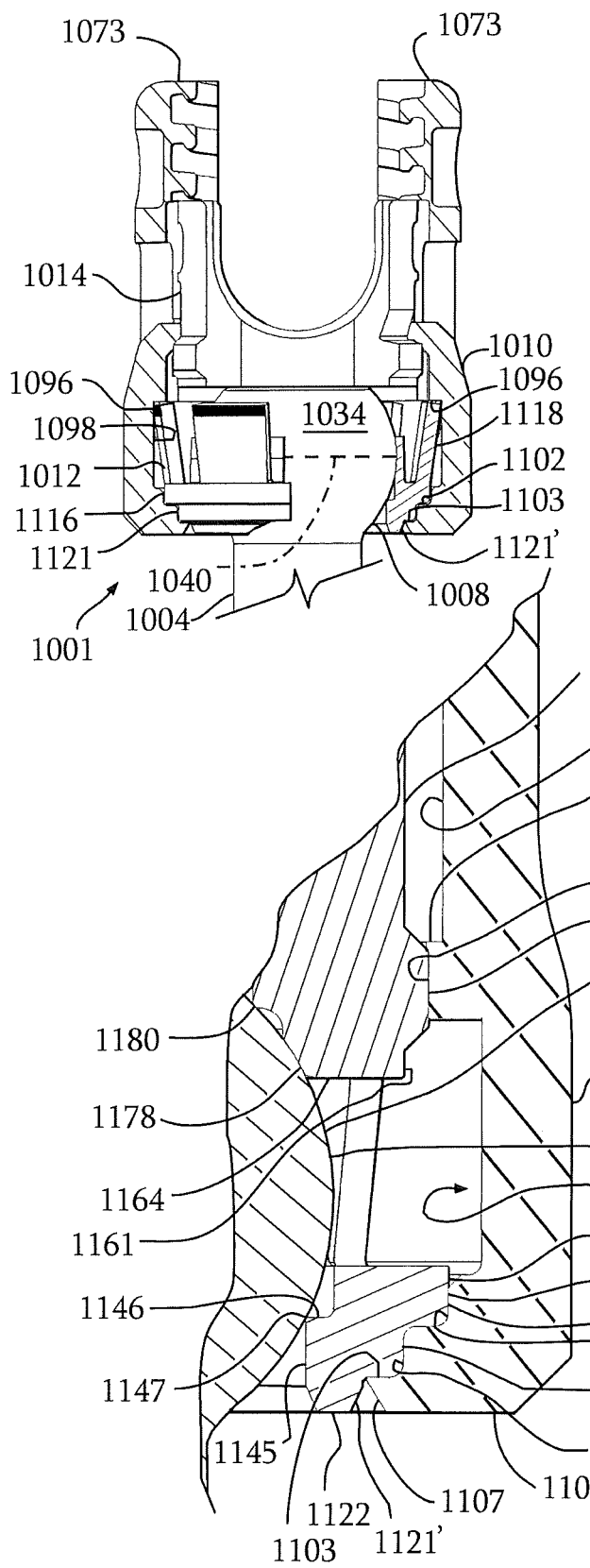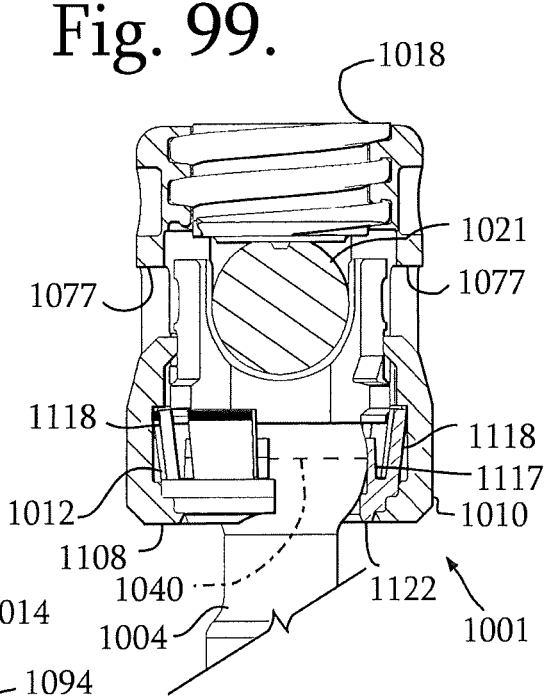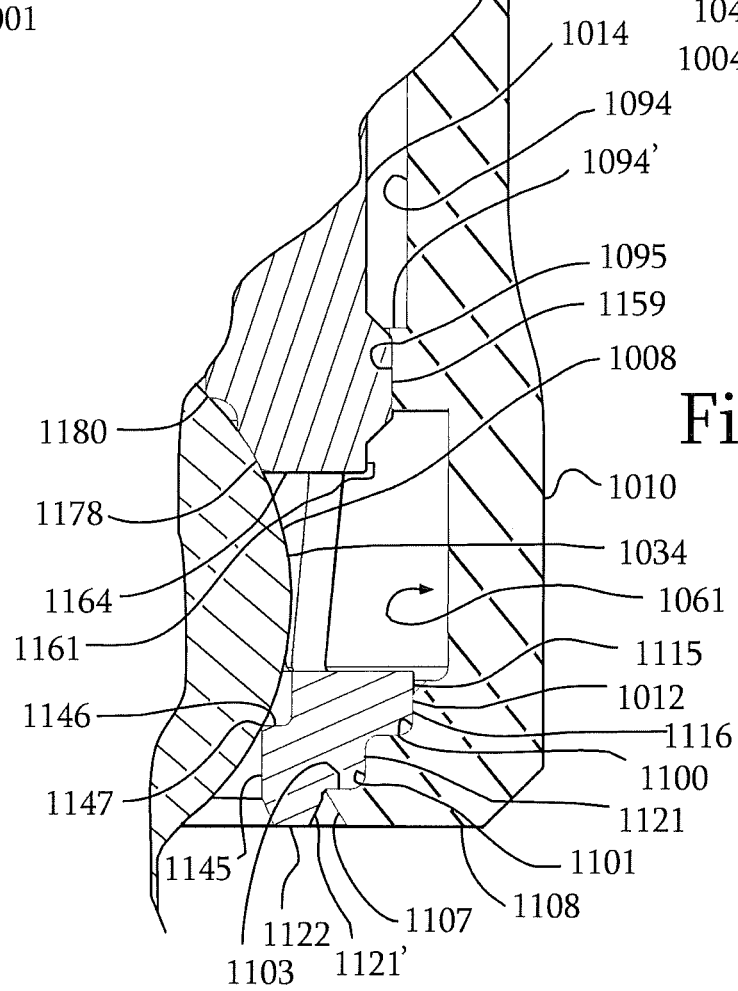

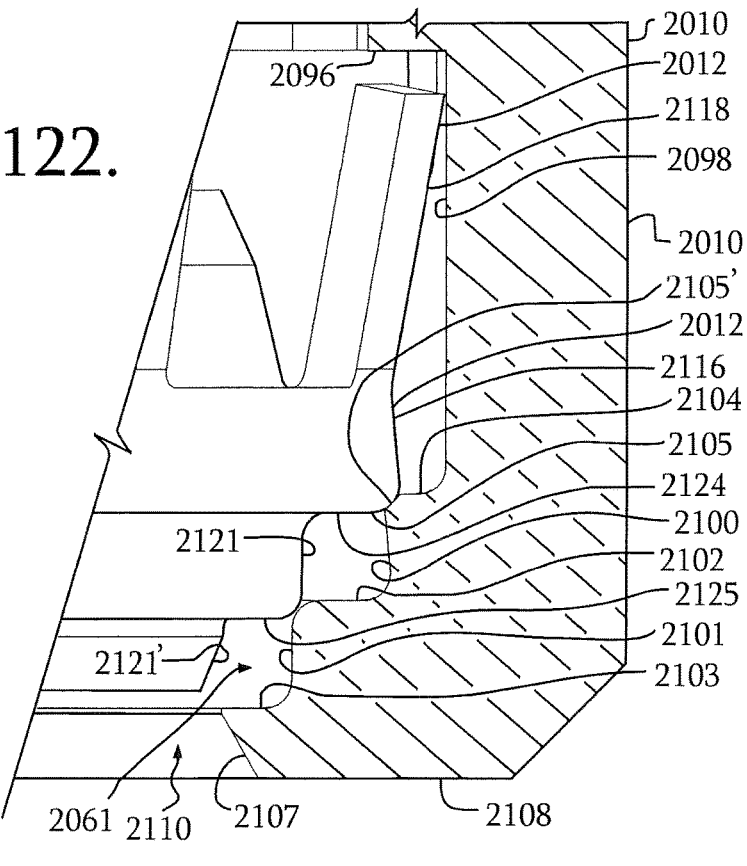
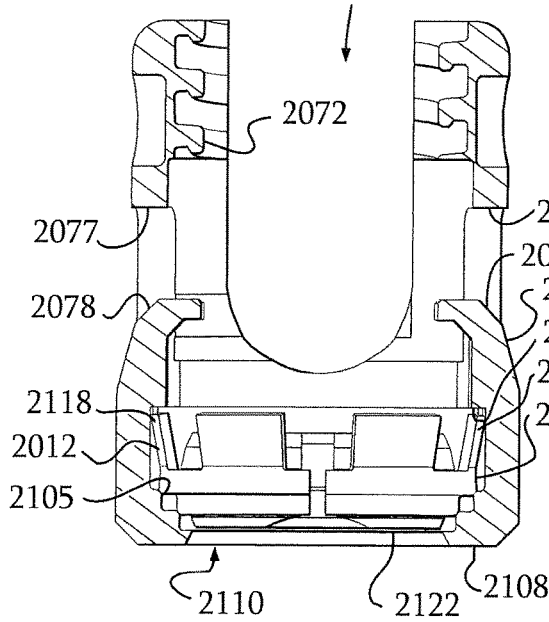
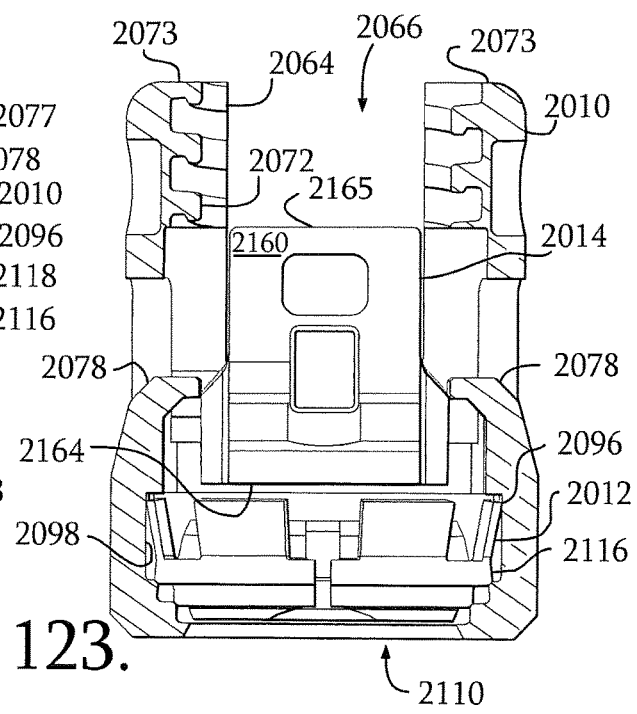
Fig. 122.
Fig. 121.
Fig. 123.

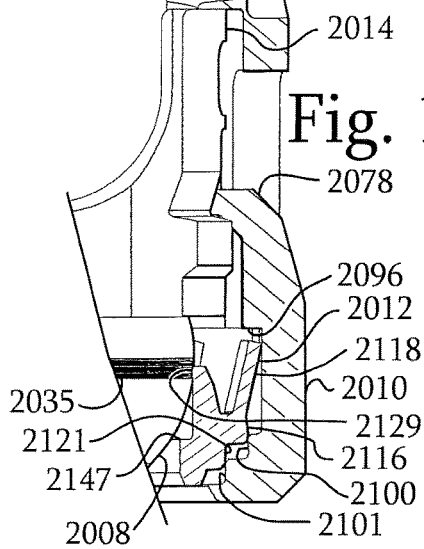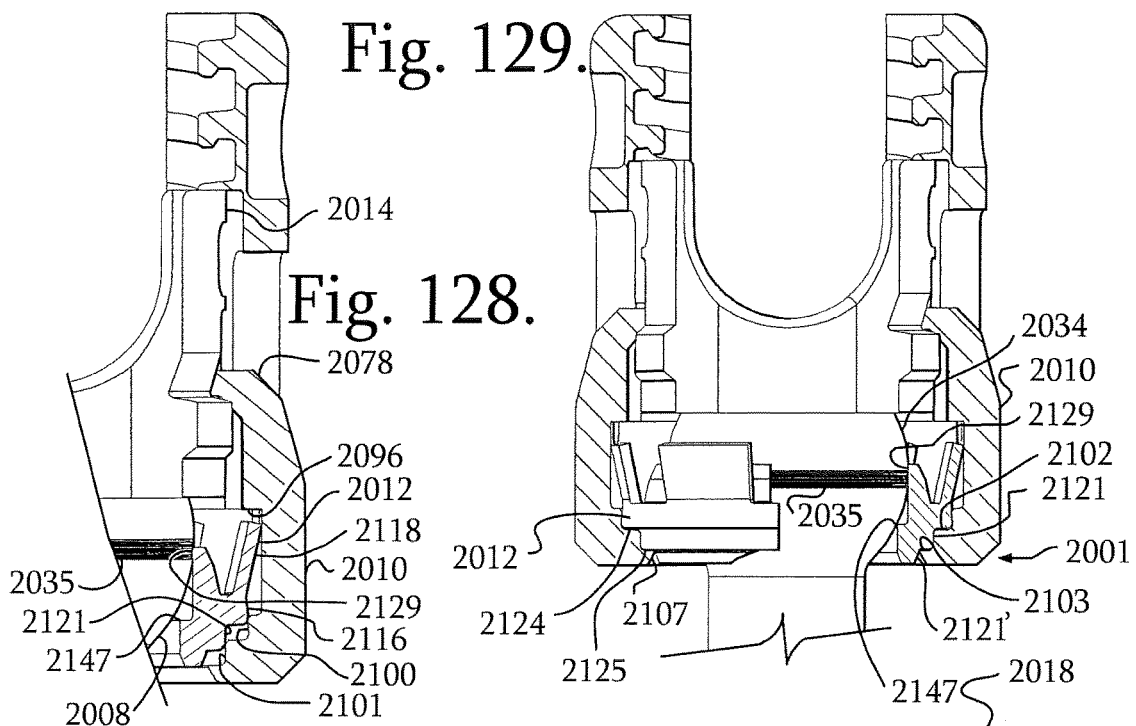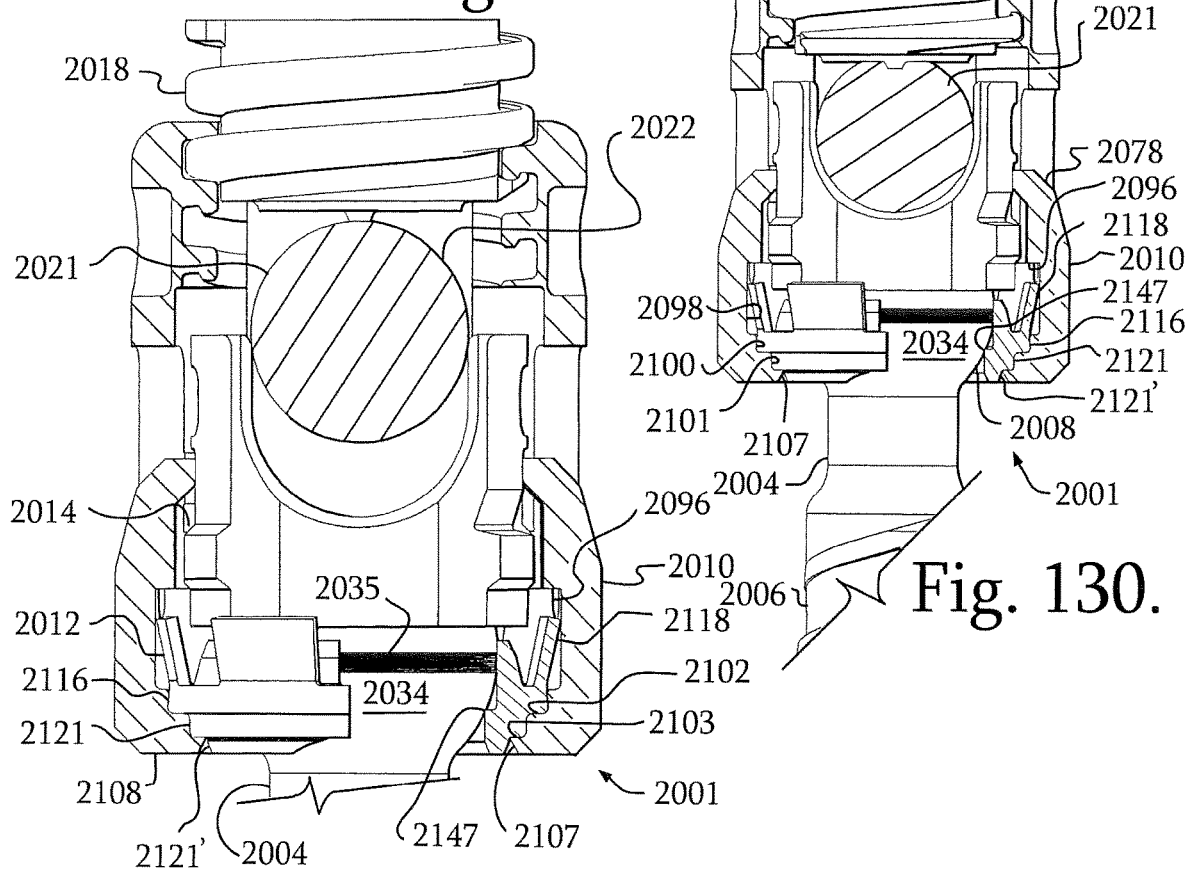
Fig. 128.
Fig. 129.
Fig. 130.
Fig. 131.

Fig. 135.
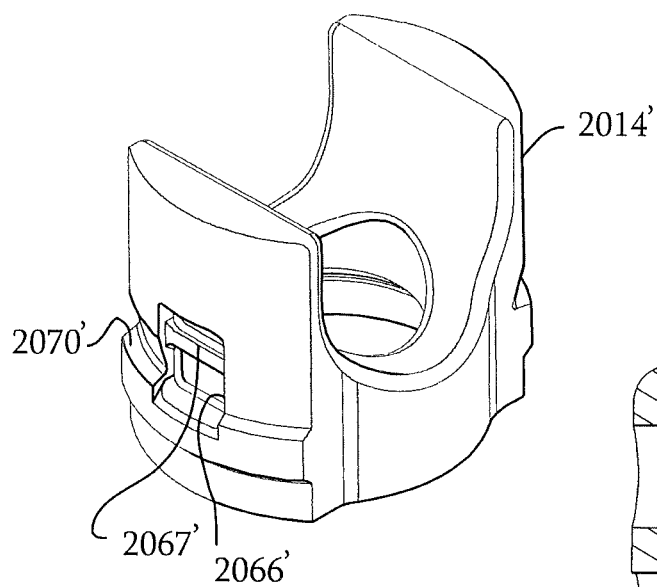
Fig. 136.
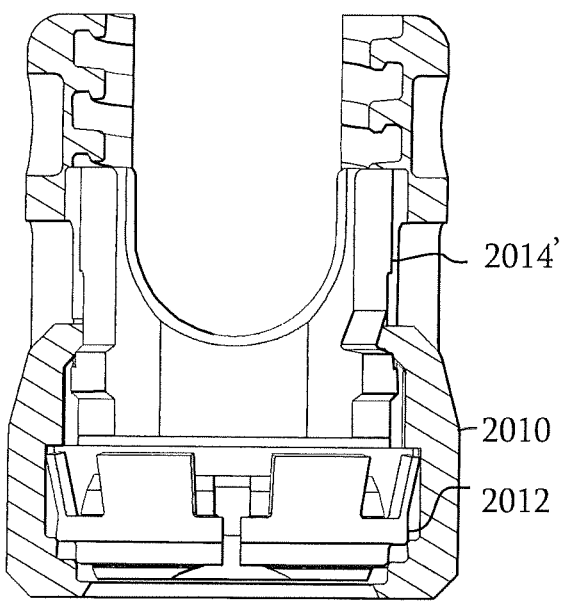
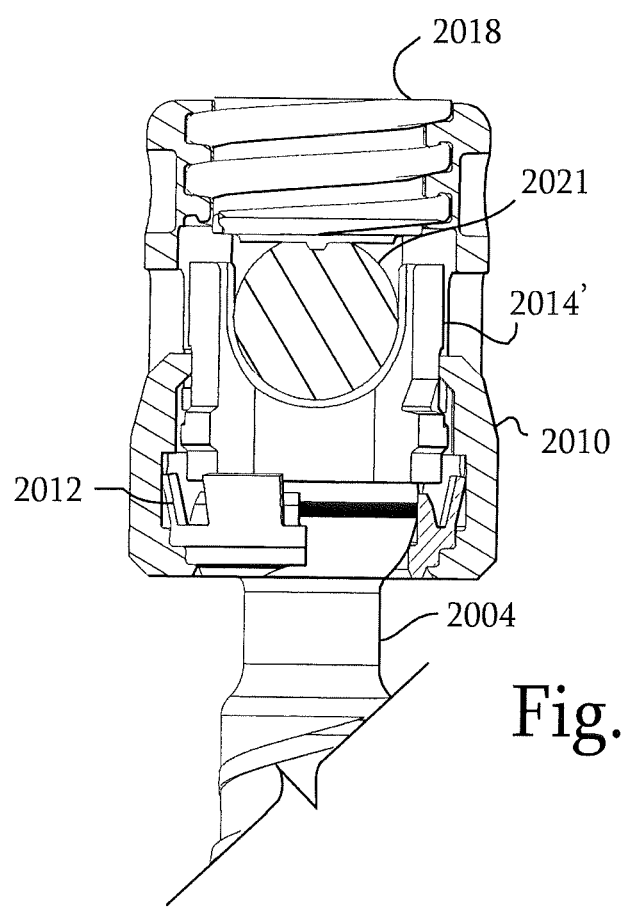
Fig. 137.

PIVOTAL BONE ANCHOR ASSEMBLY WITH FORCED DOWNWARD DISPLACEMENT OF A COMPRESSION INSERT BY A TOOL

CROSS-REFERENCE TO RELATED APPLICATIONS

This application is a continuation of U.S. application Ser. No. 15/638,039 filed Jun. 29, 2017, which is a continuation of U.S. application Ser. No. 14/872,621 filed Oct. 1, 2015 now U.S. Pat. No. 9,717,534, which is a continuation of U.S. application Ser. No. 13/573,303 filed Sep. 7, 2012 now U.S. Pat. No. 9,393,047, which claims the benefit of U.S. Provisional Application No. 61/573,508 filed Sep. 7, 2011, each of which is incorporated by reference herein for all purposes.

U.S. application Ser. No. 14/872,621 is also a continuation-in-part of U.S. application Ser. No. 13/506,365 filed Apr. 13, 2012 now U.S. Pat. No. 8,444,681, which claims the benefit of U.S. Provisional Application No. 61/517,088 filed Apr. 13, 2011, each of which is incorporated by reference herein for all purposes.

U.S. application Ser. No. 14/872,621 is also a continuation-in-part of U.S. application Ser. No. 13/385,212 filed Feb. 8, 2012 now U.S. Pat. No. 9,216,041, which claims the benefit of U.S. Provisional Application No. 61/463,037 filed Feb. 11, 2011, each of which is incorporated by reference herein for all purposes.

U.S. application Ser. No. 14/872,621 is also a continuation-in-part of U.S. application Ser. No. 13/374,439 filed Dec. 29, 2011, which claims the benefit of U.S. Provisional Application No. 61/463,037 filed Feb. 11, 2011 and U.S. Provisional Application No. 61/460,267 filed Dec. 29, 2010, each of which is incorporated by reference herein for all purposes.

U.S. application Ser. No. 14/872,621 is also a continuation-in-part of U.S. application Ser. No. 13/373,289 filed Nov. 9, 2011, which claims the benefit of U.S. Provisional Application No. 61/460,234 filed Dec. 29, 2010 and U.S. Provisional Application No. 61/456,649 filed Nov. 10, 2010, each of which is incorporated by reference herein for all purposes.

U.S. application Ser. No. 14/872,621 is also a continuation-in-part of U.S. application Ser. No. 13/136,331 filed Jul. 28, 2011 now abandoned, which claims the benefit of U.S. Provisional Application No. 61/403,915 filed Sep. 23, 2010 and U.S. Provisional Application No. 61/400,504 filed Jul. 29, 2010, each of which is incorporated by reference herein for all purposes.

U.S. application Ser. No. 14/872,621 is also a continuation-in-part of U.S. application Ser. No. 12/924,802 filed Oct. 5, 2010 now U.S. Pat. No. 8,556,938, which claims the benefit of U.S. Provisional Application No. 61/403,915 filed Sep. 23, 2010; U.S. Provisional Application No. 61/403,696 filed Sep. 20, 2010; U.S. Provisional Application No. 61/402,959 filed Sep. 8, 2010; U.S. Provisional Application No. 61/400,504 filed Jul. 29, 2010; U.S. Provisional Application No. 61/398,807 filed Jul. 1, 2010; U.S. Provisional Application No. 61/396,390 filed May 26, 2010; U.S. Provisional Application No. 61/395,752 filed May 17, 2010; U.S. Provisional Application No. 61/395,564 filed May 14, 2010; U.S. Provisional Application No. 61/343,737 filed May 3, 2010; U.S. Provisional Application No. 61/336,911 filed Jan. 28, 2010; and U.S. Provisional Application No. 61/278,240 filed Oct. 5, 2009, each of which is incorporated by reference herein for all purposes.

U.S. application Ser. No. 14/872,621 is also a continuation-in-part of U.S. application Ser. No. 12/802,849 filed Jun. 15, 2010 now abandoned, which claims the benefit of U.S. Provisional Application No. 61/396,390 filed May 26, 2010; U.S. Provisional Application No. 61/395,752 filed May 17, 2010; U.S. Provisional Application No. 61/395,564 filed May 14, 2010; U.S. Provisional Application No. 61/336,911 filed Jan. 28, 2010; U.S. Provisional Application No. 61/270,754 filed Jul. 13, 2009; and U.S. Provisional Application No. 61/268,708 filed Jun. 15, 2009, each of which is incorporated by reference herein for all purposes.

BACKGROUND OF THE INVENTION

The present invention is directed to polyaxial bone screws for use in bone surgery, particularly spinal surgery and particularly to such screws with compression or pressure inserts and expansion lock split retainers to snap over, capture and retain the bone screw shank head in the receiver member assembly and later fix the bone screw shank with respect to the receiver assembly.

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw. Generally, the screws must be inserted into the bone as an integral unit along with the head, or as a preassembled unit in the form of a shank and pivotal receiver, such as a polyaxial bone screw assembly.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include similar open ends for receiving rods or portions of other fixation and stabilization structure.

A common approach for providing vertebral column support is to implant bone screws into certain bones which then in turn support a longitudinal structure such as a rod, or are supported by such a rod. Bone screws of this type may have a fixed head or receiver relative to a shank thereof, or may be of a polyaxial screw nature. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred. Open-ended polyaxial bone screws typically allow for a loose or floppy rotation of the head or receiver about the shank until a desired rotational position of the receiver is achieved by fixing such position relative to the shank during a final stage of a medical procedure when a rod or other longitudinal connecting member is inserted into the receiver, followed by a locking screw or other closure. This floppy feature can be, in some cases, undesirable and make the procedure more difficult. Also, it is often desirable to insert the bone screw shank separate from the receiver or head due to its bulk which can get in the way of what the surgeon needs to do. Such screws that allow for this capability are sometimes referred to as modular polyaxial screws.

With specific reference to modular snap-on or pop-on polyaxial pedicle screw systems having shank receiver assemblies, the prior art has shown and taught the concept of the receiver and certain retainer parts forming an assembly wherein a contractile locking engagement between the parts is created to fix the shank head with respect to the receiver and retainer. The receiver and shank head retainer assemblies in the prior art have included a slotted contractile retainer ring and/or a lower pressure slotted insert with an expansion and contraction collet-type of structure having contractile locking engagement for the shank head due to direct contact between the retainer and/or the collet structure with the receiver resulting in contraction of the slotted retainer ring and/or the collet-type type structure of the insert against the shank head. The receiver and slotted insert have generally included tapered locking engagement surfaces.

The prior art for modular polyaxial screw assemblies has also shown and taught that the contact surfaces on the outside of the slotted collet and/or retainer and the inside of the receiver, in addition to being tapered, can be conical, radiused, spherical, curvate, multi-curvate, rounded, as well as other configurations to create a contractile type of locking engagement for the shank head with respect to the receiver.

In addition, the prior art for modular polyaxial screw assemblies has shown and taught that the shank head can both enter and escape from a collet-like structure on the insert or from the retainer when the insert or retainer is in the up position and within an expansion recess or chamber of the receiver. This is the case unless the slotted insert and/or the slotted retainer are blocked or constrained from being able to be pushed or manipulated back up into the receiver bore or cavity, or unless the screw assemblies are otherwise uniquely configured to prevent this from happening.

SUMMARY OF THE INVENTION

The present invention differentiates from the prior art by not allowing the receiver to be removed from the shank head once the parts are snapped-on and connected. This is true even if the retainer can go back up into the expansion chamber. This approach or design has been found to be more secure and to provide more resistance to pull-out forces compared to the prior art for modular polyaxial screw designs. Collect-like structures extending downwardly from lower pressure inserts, when used in modular polyaxial screw designs, as shown in the prior art, have been found to be somewhat weak with respect to pull-out forces encountered during some spinal reduction procedures. The present invention is designed to solve these problems.

The present invention also differentiates from the prior art by providing a split retainer ring with inner friction fit surfaces that may be partially radiused that do not participate in the final locking engagement for the shank head with respect to the receiver. In addition, the retainer ring itself for the present invention is uniquely characterized by a base portion providing expansion to receive and capture the shank head and then having expansion (not contraction) locking engagement between the shank head and the retainer ring base and between the retainer ring base and horizontal and vertical loading surfaces near a bottom opening of the receiver.

The expansion-only retainer ring base portion in the present invention is positioned entirely below the shank head hemisphere in the receiver and can be a stronger, more substantial structure to resist larger pull out forces on the assembly. The retainer ring base can also be better supported on a generally horizontal loading surface near the lower opening in the bottom of the receiver. This design has been found to be stronger and more secure when compared to that of the prior art which uses some type of contractile locking engagement between the parts, as described above; and, again, once assembled it cannot be disassembled.

Thus, a polyaxial bone screw assembly according to the invention includes a shank having an integral upper portion or integral radiused or spherical head and a body for fixation to a bone; a separate receiver defining an upper open channel, a central bore, a lower cavity and a lower opening; a top drop and turn in place lower compression insert; and a friction fit resilient expansion locking split retainer for capturing the shank head in the receiver lower cavity, the shank head being frictionally engaged with, but still movable in a non-floppy manner with respect to the friction fit retainer and the receiver prior to locking of the shank into a desired configuration. The shank is finally locked into a fixed position relative to the receiver by frictional engagement between the insert and a lower split ring-like portion of the retainer, as described previously, due to a downward force placed on the compression insert by a closure top pressing on a rod, or other longitudinal connecting member, captured within the receiver bore and channel. In the illustrated embodiments, retainers and compression inserts are downloaded into the receiver, but uploaded embodiments are also foreseen. The shank head can be positioned into the receiver lower cavity at the lower opening thereof prior to or after insertion of the shank into bone. In some embodiments, the compression insert may include a lock and release feature for independent locking of the polyaxial mechanism so the screw can be used like a fixed monoaxial screw. Also, in some embodiments the shank can be cannulated for minimally invasive surgery applications. The retainer includes upwardly extending tangs that are deployed in the receiver cavity so that the retainer and captured shank head are stabilized and retained in the region of the receiver locking chamber once, but are free to rotate within the cavity. In this way, the shank head and retainer are partially constrained and cannot go back up into the receiver cavity, but can be manipulated there-within.

Again, a pre-assembled receiver, compression insert and friction fit split retainer may be "pushed-on", "snapped-on" or "popped-on" to the shank head prior to or after implantation of the shank into a vertebra. Such a "snapping on" procedure includes the steps of uploading the shank head into the receiver lower opening, the shank head pressing against the base portion of the split retainer ring and expanding the resilient lower open retainer portion out into an expansion portion or chamber of the receiver cavity followed by an elastic return of the retainer back to a nominal or near nominal shape thereof after the hemisphere of the shank head or upper portion passes through the lower ring-like portion of the retainer. The shank head enters into friction fit engagement with portions of the retainer, defined at least in part, by inner tangs of the retainer. The retainer snapping onto the shank head as the retainer returns to a neutral or close to neutral orientation, providing a non-floppy connection between the retainer and the shank head. In the illustrated embodiments, when the shank is ultimately locked between the compression insert and the lower portion of the retainer, a lower retainer edge surface locks against the shank head. The final fixation occurs as a result of a locking expansion-type of contact between the shank head and the lower edge portion of the split retainer and an expansion-type of non-tapered locking engagement between the lower portion of the retainer ring and the locking chamber in the lower portion of the receiver cavity. The retainer can expand more in the upper portion or expansion chamber of the receiver cavity to allow the shank head to pass through, but has restricted expansion to retain the shank head when the retainer lower ring portion is against the locking chamber surfaces in the lower portion of the receiver cavity and the shank head is forced down against the retainer ring during final locking. In some embodiments, when the polyaxial mechanism is locked, the pressure or compression insert is forced or wedged against a surface of the receiver resulting in an interference locking engagement, allowing for adjustment or removal of the rod or other connecting member without loss of a desired angular relationship between the shank and the receiver. This independent locking feature allows the polyaxial screw to function like a fixed monoaxial screw.

The lower pressure insert may also be configured to be independently locked by a tool or instrument, thereby allowing the pop-on polyaxial screw to be distracted, compressed and/or rotated along and around the rod to provide for improved spinal correction techniques. Such a tool engages the receiver from the sides and then engages outwardly extending winged arms of the insert to force or wedge the insert down into a locked position within the receiver. With the tool still in place and the correction maintained, the rod is then locked within the receiver channel by a closure top followed by removal of the tool. This process may involve multiple screws all being manipulated simultaneously with multiple tools to achieve the desired correction.

Objects of the invention further include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded perspective view of a polyaxial bone screw assembly according to the present invention including a shank, a receiver, an open friction fit retainer and a top drop and turn in place lower compression insert, further shown with a portion of a longitudinal connecting member in the form of a rod and a closure top.

FIG. 2 is an enlarged top plan view of the shank of FIG. 1.

FIG. 3 is a reduced cross-sectional view taken along the line 3-3 of FIG. 2.

FIG. 15 is an enlarged cross-sectional view taken along the line 15-15 of FIG. 13.

FIG. 16 is another perspective view of the retainer of FIG. 11.

FIG. 34 is a reduced and partial front elevational view with portions broken away, similar to FIG. 33, the spherical shank upper portion or head shown fully captured by the retainer.

FIG. 35 is a reduced and partial front elevational view with portions broken away, similar to FIG. 34, the shank upper portion with attached retainer being shown pulled down into a seated position within the lower receiver cavity, the retainer spring tabs in a substantially neutral state, extending outwardly and captured beneath a surface of the receiver.

FIG. 36 is an enlarged and partial front elevational view with portions broken away, similar to FIG. 35, the insert being shown pushed down into a fully seated position within the lower receiver cavity by pressure being placed thereon from above by the rod and closure top of FIG. 1, also shown in partial front elevation, the insert being placed in locking interference fit with the receiver.

FIG. 37 is a partial perspective view of the locked assembly of FIG. 36 with portions broken away to show the detail thereof.

FIG. 38 is an enlarged and partial front elevational view with portions broken away, similar to FIG. 36, but with the locking insert having been pulled slightly upwardly by tooling (not shown) to result in an unlocked polyaxial mechanism.

FIG. 39 is an enlarged and partial front elevational view with portions broken away, similar to FIG. 36, but shown with the rod and closure top of FIG. 36 having been removed, the locking insert keeping the shank locked in place, the figure further showing an alternative deformable rod and cooperating closure top being installed in the receiver.

FIG. 40 is a reduced and partial front elevational view with portions broken away, similar to FIG. 39, showing the alternative rod and closure top fixed to the receiver.

FIG. 47 is an enlarged perspective view of an alternative non-locking insert according to the invention for use in lieu of the locking insert shown in FIG. 1.

FIG. 48 is another enlarged perspective view of the alternative insert of FIG. 47 with a portion broken away to show the detail thereof.

FIG. 49 is a side elevational view of the alternative insert of FIG. 47 with a portion broken away to show the detail thereof.

FIG. 50 is an enlarged front elevational view of the receiver and retainer of FIG. 1 shown in a stage of assembly with the alternative insert of FIG. 47, also in front elevation, with portions broken away to show the detail thereof.

FIG. 56 is a side elevational view of the sleeve of FIG. 52 with portions broken away to show the detail thereof.

FIG. 57 is a reduced perspective view of the sleeve of FIG. 52 shown assembled with a bone screw assembly of FIG. 1 (shown partially exploded), with the rod of FIG. 1 being replaced by a cord, and further showing a pair of transparent compressible cylindrical spacers located about the cord and at either side of the sleeve.

FIG. 58 is an enlarged cross-sectional view taken along the line 58-58 of FIG. 57 with the closure top shown mated with the receiver.

FIG. 59 is a reduced cross-sectional view taken along the line 59-59 of FIG. 58.

FIG. 60 is a partially exploded, front elevational view of the sleeve of FIG. 52 and bone screw assembly of FIG. 1, but with the rod and closure top of FIG. 1 being replaced by a cord and an alternative cord-locking closure top.

FIG. 61 is a front elevational view, similar to FIG. 60, with portions broken away to show the detail thereof, showing the alternative cord-locking closure top engaging the sleeve and the receiver.

FIG. 62 is an enlarged and partial, perspective view of the assembly shown in FIG. 57, but with one of the spacers being replaced with a bumper (shown transparent) and blocker/set screw combination, shown partially exploded.

FIG. 63 is an enlarged and partial side elevational view of the assembly of FIG. 62 with portions broken away to show the detail thereof, showing the set screw fixing the cord with respect to the blocker and the cord in slidable relationship with the bone screw.

FIG. 64 is an enlarged perspective view of the assembly of FIG. 1, but with the rod and closure top of FIG. 1 being replaced by a second alternative sleeve with rectangular faces, a cord and alternative cord-locking closure top of the invention.

FIG. 65 is a partial and partially exploded front elevational view of the assembly of FIG. 64.

FIG. 66 is an enlarged and partial front elevational view of the assembly of FIG. 64 with portions broken away to show the detail thereof.

FIG. 67 is an enlarged perspective view of the alternative sleeve of FIG. 64.

FIG. 68 is a top plan view of the alternative sleeve of FIG. 67.

FIG. 69 is a bottom plan view of the alternative sleeve of FIG. 67.

FIG. 70 is a side elevational view of the alternative sleeve of FIG. 67 with portions broken away to show the detail thereof.

FIG. 71 is a reduced perspective view of the assembly of FIG. 64 further shown with an alternative compressible spacer having an oval profile (shown transparent).

FIG. 72 is a partial side elevational view of the assembly of FIG. 71 further shown with a second alternative compressible spacer with an oval profile (also shown transparent).

FIG. 73 is an enlarged front elevational view of the compressible spacer with oval profile shown in FIG. 71.

FIG. 74 is a top plan view of the spacer of FIG. 73.

FIG. 81 is an enlarged and partial front elevational view of the retainer of FIG. 80.

FIG. 82 is a perspective view of the retainer of FIG. 80.

FIG. 83 is another perspective view of the retainer of FIG. 80.

FIG. 94 is a front elevational view of the retainer and receiver with portions broken away, similar to what is shown in FIG. 93, further showing the insert being rotated to a desired position in the receiver with the receiver spring tabs pressing into apertures of the insert and further showing the retainer tangs being squeezed (tool not shown) in preparation for moving the retainer upwardly toward the insert.

FIG. 95 is a front elevational view of the retainer and receiver with portions broken away, similar to what is shown in FIG. 94, the retainer shown in a position wherein the tangs push resiliently outwardly against the receiver, holding the retainer against the receiver and keeping the retainer in an upward position during shipping and assembly with the shank of FIG. 75, the figure further showing the shank of FIG. 75 in an enlarged and partial front elevational view at an early stage of assembly with the retainer, a hemisphere of the shank head is shown in phantom.

FIG. 96 is an enlarged and partial front elevational view with portions broken away, similar to FIG. 95, showing the retainer lower portion in an expanded state about a midportion of the shank head.

FIG. 97 is an enlarged and partial front elevational view with portions broken away, similar to FIG. 96, the spherical shank upper portion or head shown fully captured by the retainer.

FIG. 98 is a reduced and partial front elevational view with portions broken away, similar to FIG. 97, the shank upper portion with attached retainer being shown pulled down into a seated position within the lower receiver cavity, the retainer tangs in a substantially neutral state, extending outwardly and captured beneath a surface of the receiver.

FIG. 99 is a reduced and partial front elevational view with portions broken away, similar to FIG. 98, the insert being shown pushed down into a fully seated position within the lower receiver cavity by pressure being placed thereon from above by the rod and closure top of FIG. 75, also shown in partial front elevation, the insert being placed in locking interference fit with the receiver.

FIG. 100 is an enlarged and partial front elevational view with portions broken away of the assembly as shown in FIG. 99.

FIG. 120 is a perspective view of the retainer and receiver with portions broken away, similar to what is shown in FIG. 119, showing the retainer in a subsequent stage of assembly and in a maximum state of compression.

FIG. 121 is a front elevational view of the retainer and receiver with portions broken away, similar to what is shown in FIG. 119, showing the retainer tangs fully deployed within the receiver cavity, but the retainer not fully seated within the receiver cavity.

FIG. 122 is an enlarged and partial front elevational view of the assembly as shown in FIG. 121.

FIG. 123 is a front elevational view of the retainer and receiver with portions broken away, similar to FIG. 121 and further including the insert in side elevation, being downloaded into the receiver and at a location suitable for rotation within the receiver.

Figures 107, 108:
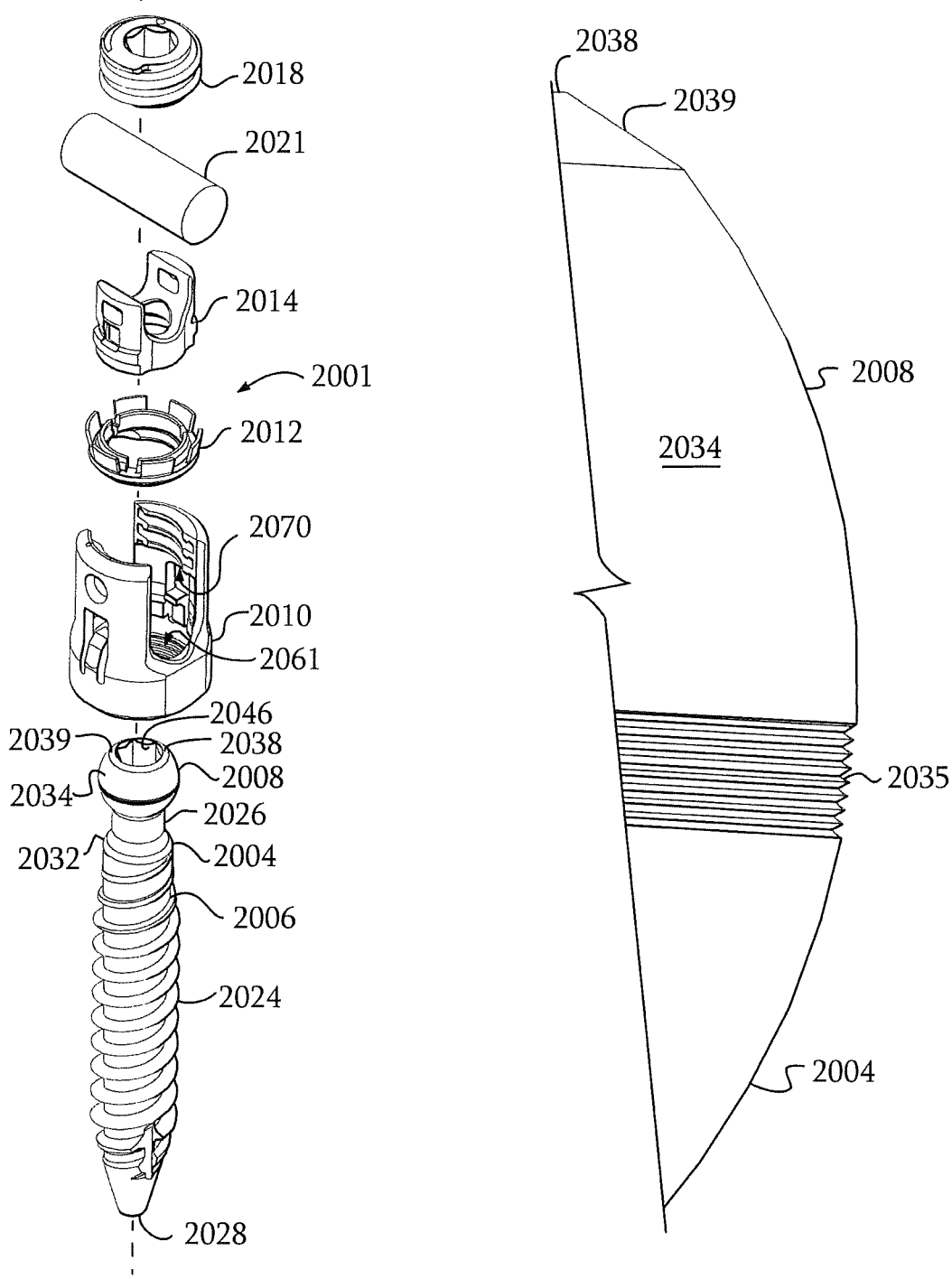
FIG. 107 is an exploded perspective view of another alternative polyaxial bone screw assembly according to the present invention including a shank, a receiver, an open friction fit retainer and a top drop and turn in place lower compression insert, further shown with a portion of a longitudinal connecting member in the form of a rod and a closure top.
FIG. 108 is an enlarged and partial front elevational view of the shank of FIG. 107.
Figure 124:
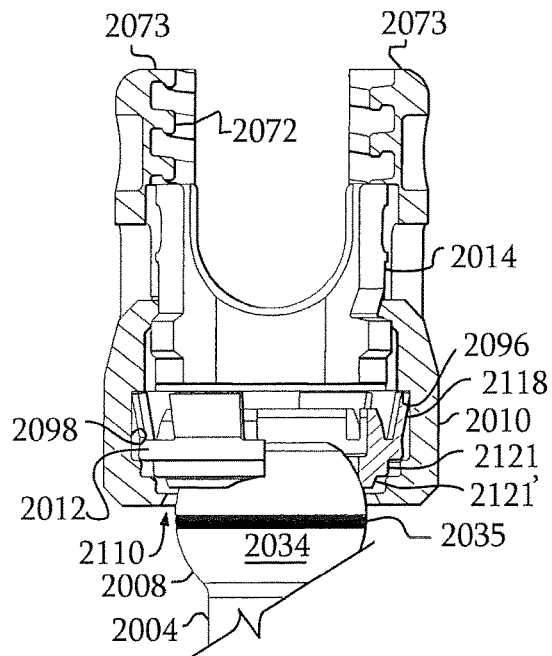

FIG. 124 is a reduced front elevational view of the retainer and receiver with portions broken away, similar to what is shown in FIG. 123, further showing the insert being rotated to a desired position in the receiver with the receiver spring tabs pressing into apertures of the insert and further showing the shank of FIG. 107 in an enlarged and partial front elevational view at an early stage of assembly with the retainer.

Figure 125:
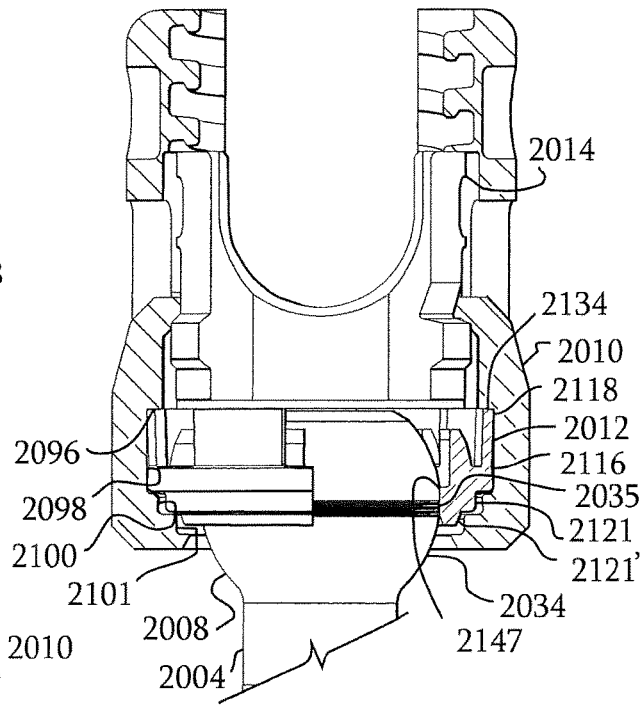

FIG. 125 is an enlarged and partial front elevational view with portions broken away, similar to FIG. 124, showing the retainer lower portion in an expanded state about a mid-portion of the shank head.

Figure 126:
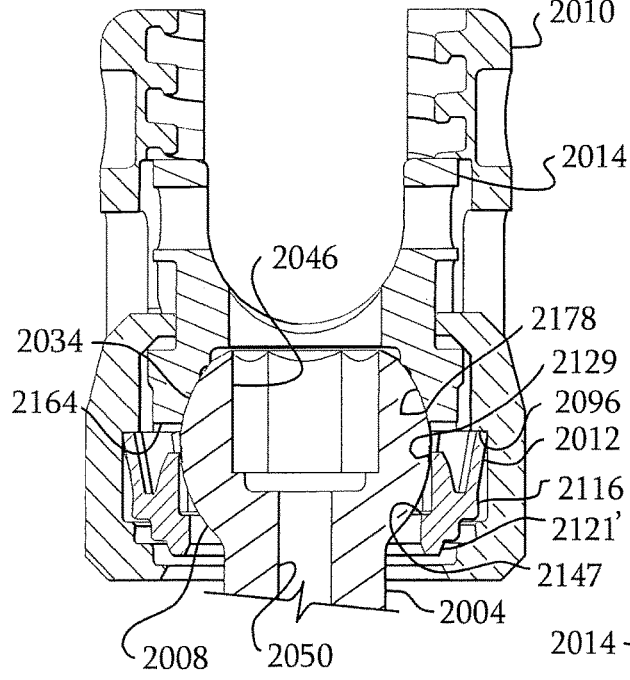

FIG. 126 is an enlarged and partial front elevational view with portions broken away, similar to FIG. 125, the spherical shank upper portion or head shown fully captured by the retainer and the shank head being shown pressing up against the insert.

Figure 127:
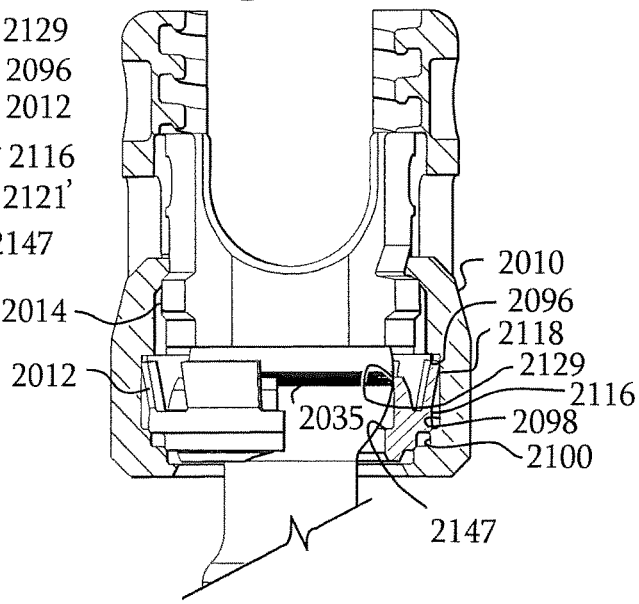

FIG. 127 is a reduced and partial front elevational view with portions broken away, similar to FIG. 126, the shank upper portion being shown partially pulled down into the receiver cavity, the retainer outer tangs in a substantially neutral state and the inner tangs contacting ridges on the shank head.

FIG. 128 is an enlarged and partial front elevational view with portions broken away, similar to FIG. 127, showing a further pull-down of the shank head with respect to inner retainer tangs.

FIG. 129 is an enlarged and partial front elevational view with portions broken away, similar to FIG. 128, showing a further pull-down of the shank head and attached retainer, the retainer being pulled down to a seated position within the receiver cavity.

FIG. 130 is a reduced and partial front elevational view with portions broken away, similar to FIG. 129, the insert being pushed down into a fully seated position within the lower receiver cavity by pressure being placed thereon from above by the rod and closure top of FIG. 107, also shown in partial front elevation, the insert being placed in locking interference fit with the receiver.

FIG. 131 is an enlarged and partial front elevational view with portions broken away of the assembly of FIG. 130, but with the closure top loosened and the rod lifted up, the insert however remaining locked into place against the receiver, maintaining the retainer and shank in a locked position.

Figure 132:
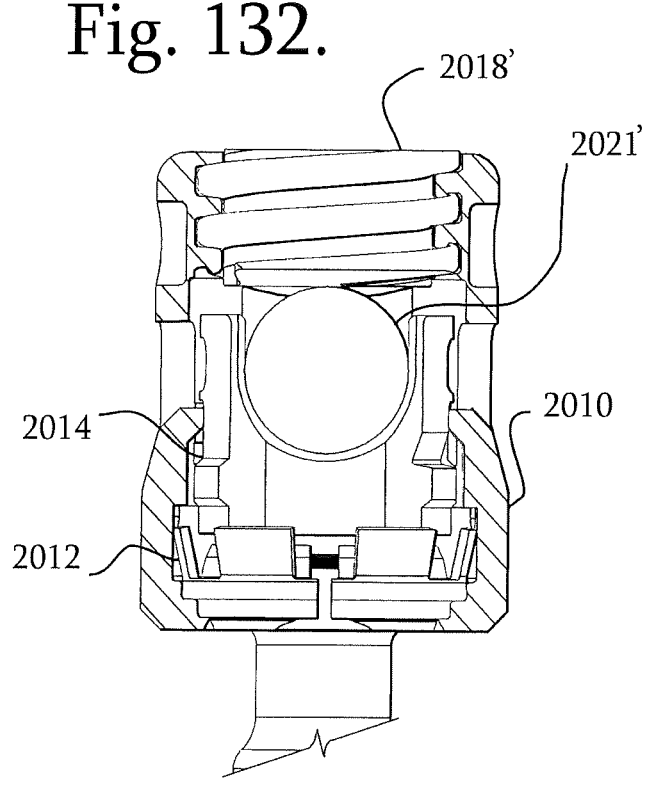

FIG. 132 is a reduced and partial front elevational view with portions broken away of the assembly of FIG. 131 with the exception that the rod and closure top have been removed and replaced with an alternative deformable rod and cooperating alternative closure top.

Figure 133:
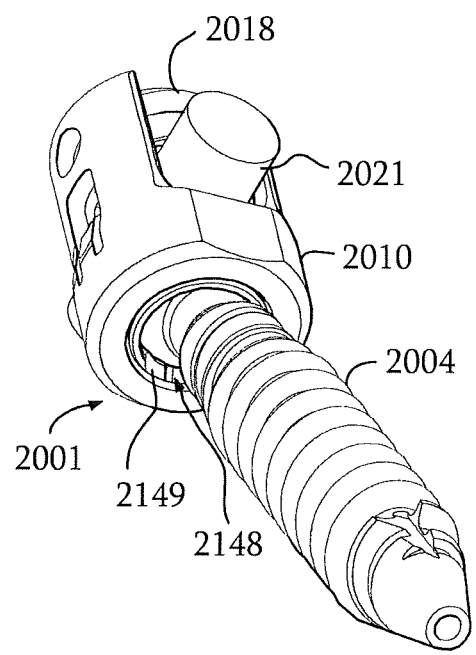

FIG. 133 is an enlarged and partial perspective view of the assembly of FIG. 107, shown fully assembled with the shank disposed at a twenty degree (cephalad) angle with respect to the receiver.

Figure 134:
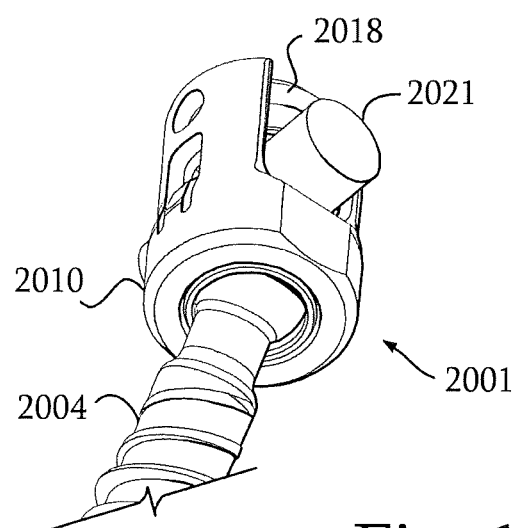

FIG. 134 is an enlarged and partial perspective view of the assembly of FIG. 107, shown fully assembled with the shank disposed at a thirty degree (caudad) angle with respect to the receiver.

FIG. 135 is an enlarged perspective view of an alternative non-locking insert according to the invention for use in lieu of the locking insert shown in FIG. 107.

FIG. 136 is an enlarged front elevational view of the alternative insert of FIG. 135 shown in a stage of assembly with the receiver and retainer of FIG. 107, with portions broken away to show the detail thereof.

FIG. 137 is an enlarged and partial front elevational view of the receiver, retainer, rod and closure top of FIG. 107 shown fully assembled with the alternative insert of FIG. 135, also in front elevation, with portions broken away to show the detail thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

With reference to FIGS. 1-38 and 41-46, the reference number 1 generally represents a polyaxial bone screw apparatus or assembly according to the present invention. The assembly 1 includes a shank 4, that further includes a body 6 integral with an upwardly extending upper portion or head 8; a receiver 10; a friction fit retainer 12, and a crown-like compression or pressure insert 14. The receiver 10, retainer 12 and compression insert 14 are initially assembled and may be further assembled with the shank 4 either prior or subsequent to implantation of the shank body 6 into a vertebra 17, as will be described in greater detail below. FIGS. 1 and 36-37 further show a closure structure 18 for capturing a longitudinal connecting member, for example, a rod 21 which in turn engages the compression insert 14 that presses against the shank head 8 into fixed frictional contact with the retainer 12, so as to capture, and fix the longitudinal connecting member 21 within the receiver 10 and thus fix the member 21 relative to the vertebra 17. The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure. The illustrated rod 21 is hard, stiff, non-elastic and cylindrical, having an outer cylindrical surface 22. In some embodiments, the rod 21 may be elastic, deformable and/or of different materials and cross-sectional geometries (see, e.g., FIGS. 39 and 40). It is foreseen that in other embodiments (not shown) the closure top could deform the rod and press directly on the insert 14.

Figure 31:
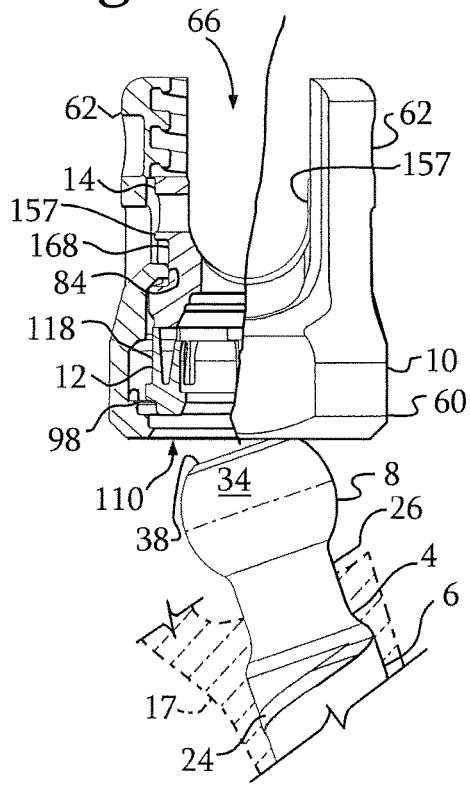
FIG. 31 is a reduced front elevational view with portions broken away, similar to FIG. 30, showing the insert fully rotated within the receiver with the receiver spring tabs pressing into apertures of the insert and with retainer spring tabs located to push resiliently outwardly against the receiver, holding the retainer against the receiver and keeping the retainer in an upward position during shipping and assembly with the shank of FIG. 1, the figure further showing the shank of FIG. 1 in an enlarged and partial front elevational view and implanted into a portion of a vertebra, a hemisphere of the shank head and the vertebra portion are both shown in phantom.

The shank 4, best illustrated in FIGS. 1-3, is elongate, with the shank body 6 having a helically wound bone implantable thread 24 (single or dual lead thread form and different thread types) extending from near a neck 26 located adjacent to the upper portion or head 8, to a tip 28 of the body 6 and extending radially outwardly therefrom. During use, the body 6 utilizing the thread 24 for gripping and advancement is implanted into the vertebra 17 leading with the tip 28 and driven down into the vertebra with an installation or driving tool (not shown), so as to be implanted in the vertebra to a location at or near the neck 26, as shown in FIG. 31, for example, and more fully described in the paragraphs below. The shank 4 has an elongate axis of rotation generally identified by the reference letter A.

The neck 26 extends axially upward from the shank body 6. The neck 26 may be of the same or is typically of a slightly reduced radius as compared to an adjacent upper end or top 32 of the body 6 where the thread 24 terminates. Further extending axially and outwardly from the neck 26 is the shank upper portion or head 8 that provides a connective or capture apparatus disposed at a distance from the upper end 32 and thus at a distance from the vertebra 17 when the body 6 is implanted in such vertebra.

The shank upper portion 8 is configured for a pivotable connection between the shank 4 and the retainer 12 and receiver 10 prior to fixing of the shank 4 in a desired position with respect to the receiver 10. The shank upper portion 8 has an outer, convex and substantially spherical surface 34 that extends outwardly and upwardly from the neck 26 that in some embodiments terminates at a substantially a circular or polygonal edge or rim 38. In the illustrated embodiment, a frusto-conical surface 39 extends from the spherical surface 34 inwardly to the top edge 38, providing additional clearance during pivoting of the shank with respect to the receiver 10 and the insert 14. The spherical surface 34 has an outer radius configured for temporary frictional, non-floppy, sliding cooperation with one or more edges and/or surfaces of the retainer 12, as well as ultimate frictional engagement with the retainer 12 at a lower inner edge thereof and ultimate frictional engagement with the insert 14 at an inner partially spherical surface thereof and/or stepped or ridged surfaces thereof, as will be discussed more fully in the paragraphs below. In FIG. 1 and some of the other figures, a dotted line 40 designates a hemisphere of the spherical surface 34. The spherical surface 34 shown in the present embodiment is substantially smooth, but in some embodiments may include a roughening or other surface treatment and is sized and shaped for cooperation and ultimate frictional engagement with the compression insert 14 as well as ultimate frictional engagement with a lower ring-like edge of the retainer 12. The shank spherical surface 34 is locked into place exclusively by the insert 14 and the retainer 12 lower edged portion and not by inner surfaces defining the receiver cavity.

A counter sunk and stepped or graduated annular seating surface or base 45 partially defines a portion of an internal drive feature or imprint 46. In some embodiments of the invention, the surface 45 is substantially planar. The illustrated internal drive feature 46 is an aperture formed in the top 38 and has a hex shape designed to receive a tool (not shown) of an Allen wrench type, into the aperture for rotating and driving the bone screw shank 4 into the vertebra 17. It is foreseen that such an internal tool engagement structure may take a variety of tool-engaging forms and may include one or more apertures of various shapes, such as a pair of spaced apart apertures or a multi-lobular or star-shaped aperture. The graduated seat or base surfaces 45 of the drive feature 46 are disposed substantially perpendicular to the axis A with the drive feature 46 otherwise being coaxial with the axis A. As illustrated in FIGS. 2 and 3, the drive seat 45 having beveled or stepped surfaces advantageously further enhances gripping with the driving tool. In operation, the driving tool (not shown) is received in the internal drive feature 46, being seated at the base 45 and engaging the faces of the drive feature 46 for both driving and rotating the shank body 6 into the vertebra 17, either before or after the shank 4 is connected to the receiver 10 via the retainer 12, the driving tool extending into the receiver 10 when the shank 4, retainer 12 and receiver 10 combination is driven into the vertebra 17.

The shank 4 shown in the drawings is cannulated, having a small central bore 50 extending an entire length of the shank 4 along the axis A. The bore 50 is defined by an inner cylindrical wall of the shank 4 and has a circular opening at the shank tip 28 and an upper circular opening communicating with the external drive 46 at the driving seat 45. The bore 50 is coaxial with the threaded body 6 and the upper portion or head 8. The bore 50 provides a passage through the shank 4 interior for a length of wire (not shown) inserted into the vertebra 17 prior to the insertion of the shank body 6, the wire providing a guide for insertion of the shank body 6 into the vertebra 17. It is foreseen that the shank could be solid and made of different materials, including metal and non-metals.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to:

alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 1 and 4-10, the receiver 10 has a generally U-shaped appearance with partially discontinuous cylindrical inner and outer profiles as well as planar and other curved surfaces. The receiver 10 has an axis of rotation B that is shown in FIG. 1 as being aligned with and the same as the axis of rotation A of the shank 4, such orientation being desirable, but not required during assembly of the receiver 10 with the shank 4. After the receiver 10 is pivotally attached to the shank 4, either before or after the shank 4 is implanted in a vertebra 17, the axis B is typically disposed at an angle with respect to the axis A, as shown, for example, in FIGS. 41-46.

The receiver 10 includes a base 60 with various curved and mostly cylindrical surfaces 58 and opposed outer planar surfaces 59, the base 60 defining a bore or inner cavity, generally 61, the base 60 being integral with a pair of opposed upstanding arms 62. At the base 60, the planar surfaces 59 are located between the arms 62 and an inset surface portion 63 is located above and adjacent to each planar surface 59, each inset surface portion 63 spanning between the pair of arms 62. The arms 62 form a cradle and define a U-shaped channel 64 between the arms 62 with an upper opening, generally 66, and a U-shaped lower channel portion or seat 68, the channel 64 having a width for operably snugly receiving the rod 21 or portion of another longitudinal connector or sleeve (such as those shown in FIGS. 52-74) between the arms 62, the channel 64 communicating with the base cavity 61. Inner opposed substantially planar arm surfaces 69 partially define the channel 64 above the curved seat 68 and partially define outer sides of each arm interior surface generally 70, that includes various inner cylindrical profiles, an upper one of which is a partial helically wound guide and advancement structure 72 located adjacent top surfaces 73 of each of the arms 62. In the illustrated embodiment, the guide and advancement structure 72 is a partial helically wound interlocking flangeform configured to mate under rotation with a similar structure on the closure structure 18, as described more fully below. However, it is foreseen that for certain embodiments of the invention, the guide and advancement structure 72 could alternatively be a square-shaped thread, a buttress thread, a reverse angle thread or other thread-like or non-thread-like helically wound discontinuous advancement structures, for operably guiding under rotation and advancing the closure structure 18 downward between the arms 62, as well as eventual torquing when the closure structure 18 abuts against the rod 21 or other longitudinal connecting member. It is foreseen that the arms 62 could have break-off extensions.

An opposed pair of circular tool receiving and engaging apertures 74 are formed on outer substantially cylindrical surfaces 76 of the arms 62 near the top surfaces 73. Furthermore, below each aperture 74 is a through aperture or bore 77 also formed in and through each of the outer surfaces 76, each aperture 77 having a generally up-side down U-shape, the U-shape aperture defining a central inwardly and upwardly extending holding tab 78 integral with the respective arm 62 at or near the base 60, generally extending upwardly from the receiver base 60 and inwardly toward the receiver axis B. Each aperture 77 extends through the respective arm surface 76 to the respective inner arm surface 70. Each aperture 77 is located spaced from the adjacent aperture 74 and near or adjacent the receiver base 60. Some or all of the apertures 74 and 77 may be used for holding the receiver 10 during assembly with the insert 14, the retainer 12 and the shank 4, during the implantation of the shank body 6 into a vertebra when the shank is pre-assembled with the receiver 10, and during assembly of the bone anchor assembly 1 with the rod 21 or other longitudinal connecting member and the closure structure 18. It is foreseen that tool receiving grooves or apertures may be configured in a variety of shapes and sizes and be disposed at other locations on the receiver arms 62.

The assembly 1 is typically provided to a user with the insert 14 being held within the receiver by the pair of inwardly extending holding tabs 78, that are typically somewhat resilient, firmly holding the insert 14 during assembly with the shank 4 and keeping the insert 14 relatively stationary with respect to the receiver 10 in an upward position between the arms 62 until the insert 14 is pressed downwardly into locking friction fit with the shank upper portion or head 8. The holding tabs 78 advantageously hold the insert 14 in a centered position (the insert arms being held in alignment with the receiver arms) during rotation and torquing of the closure top 18 onto the rod 21 or other connecting member. The opposed holding tabs 78 include outer surfaces and also various inner surfaces for contacting the insert 14. The tab surfaces include a first outer surface 80 extending from the base 60 and sloping upwardly and slightly inwardly toward the receiver axis B. A second inwardly sloping surface 81 is adjacent to the surface 80 and is directed toward the axis B at an angle with respect thereto. The surface 81 generally extends between the receiver outer periphery to the inner arm surface 70. Adjacent to the surface 81 is a tab top surface 82 that runs toward the axis B and is substantially perpendicular thereto. An inner insert engaging surface 84 is substantially perpendicular to the top surface 82. The surface 84 is adjacent to a lower tab surface 85 and is perpendicular thereto. The insert engaging surface 84 is illustrated as having a slightly concave or cylindrical shape (may also be planar), sized and shaped for engagement with an outer substantially cylindrical surface of the insert 14 as will be described in greater detail below. The lower surface 85 is parallel to the top surface 82. The holding tabs 78 are stable, but exhibit some resilience, being pushed outwardly away from the axis B during rotation of the insert 14 when the insert 14 is being assembled with the receiver 10 as shown, for example, in FIG. 30. Each holding tab 78 further includes opposed side surfaces 88 that partially define the U-shaped portion of the through aperture 77. The aperture 77 is further defined by a top surface 89, opposed outer substantially planar side surfaces 90 and a pair of spaced, curved bottom surfaces 91.

Returning to the interior surface 70 of the receiver arms 62, located below the guide and advancement structure 72 is a discontinuous cylindrical surface 92 partially defining a run-out feature for the guide and advancement structure 72. The cylindrical surface 92 is sized and shaped to receive the insert 14 as will be described in greater detail below. The surface 92 has a diameter slightly greater than a greater diameter of the guide and advancement structure 72. The illustrated receiver 10 further includes sloped, stepped or chamfered surface above and below the surface 92. The surface 92 is divided not only by the U-shaped channel 64, but also by each of the through apertures 77. A lower partially sloping or stepped ledge 94 at the base of the cylindrical surface 92 slopes downwardly toward the receiver base 60 and extends inwardly toward the axis B, the surface 94 terminating at a cylindrical surface 95 that extends completely around the receiver base 60 and thus runs beneath each arm 62 and is adjacent to the lower seat 68. The inner surface 95 thus defines an upper and inner portion of the receiver base 60. The cylindrical surface has a diameter slightly smaller than the diameter of the surface 92. Lower legs of the through aperture 77 partially defined by the surfaces 88 extend through the surface 95. The surface 95 terminates at a ledge surface or chamber ceiling 96 that extends outwardly away from the axis B, the surface 96 being substantially perpendicular to the axis B, but could be oblique. The surface 96 is annular and defines an upper ceiling or stop of a retainer ring expansion portion or chamber of the inner cavity 61 that is further defined by an adjacent outwardly sloping surface 97 and a cylindrical surface 98 that is adjacent the surface 97. The surface 97 acts as a stop for and slidingly cooperates with outwardly and upwardly projecting retainer tangs or panels as will be described in greater detail below. The cylindrical surface 98 has a diameter greater than the diameter of the cylindrical surface 95. The cylindrical surfaces 92, 95 and 98 are all centrally aligned with and run parallel to the receiver axis B. Lower surface portions 91 that define the through aperture 77 extend into and through the sloping surface 97. The surface 98 defines a circumferential recess that is sized and shaped to receive the retainer 12 as it expands around the shank upper portion 8 as the shank 8 moves upwardly toward the channel 64 during assembly. It is foreseen that the recess could be tapered or conical in configuration.

A pair of cylindrical surfaces 100 and 101 with an annular step surface 102 therebetween as well as a lower annular step 103 located below and adjacent to the surface 101 provide a lower seat for the retainer 12 as will be described in greater detail below. The surfaces 102 and 103 are substantially perpendicular to the surfaces 100 and 101 and the receiver axis B. The surfaces 100, 101, 102 and 103 are located below the cylindrical surface 98 in the lower part of the base 60 and are sized and shaped to closely receive and surround a lower base portion and lower skirt or substructure of the retainer 12 when the retainer is in a reduced deployment position as shown in FIGS. 35-38, for example. Thus, the cylindrical surface 101 has a diameter smaller than the diameter of the cylindrical surface 98 that defines the expansion area or expansion chamber for the retainer 12. The surface 101 is joined or connected to the surface 98 by one or more beveled, curved or conical transition step surfaces 104. The surfaces 104 allow for sliding and nominal or deployment positioning of the retainer 12 into the space defined by the surfaces 100 and 101 and ultimate seating of the retainer 12 on the lower substantially horizontal annular surfaces 102 and 103.

Located below and adjacent to the annular seating surface 103 is a lower edge or rim surface 106 that communicates with a beveled or flared bottom opening surface 107, the surface 107 communicating with an exterior base or bottom surface 108 of the base 60, defining a lower opening, generally 110, into the base cavity 61 of the receiver 10. In some embodiments of the invention, it is foreseen that a curvate cut-out or cupped surface may be formed in a portion of the base surface 108, as well as in portions of the surfaces 107, 106 and 100-104 located substantially centrally and directly below one of the arms 62. Such a cupped surface may be sized and shaped for providing clearance for an increased angle of articulation between the shank 4 and the receiver 10.

With particular reference to FIGS. 1 and 11-16, the lower open or split friction fit retainer 12, that operates to capture the shank upper portion 8 within the receiver 10 is shown. In certain stages of assembly and operation, the retainer 12 is partially constrained within the receiver, being captured within the receiver cavity 61 at a location below the surface 97, the retainer 12 being rotatable with respect to the receiver, but not pivotable thereto and not readily removable out of the receiver once deployed downward into the receiver cavity 61. The retainer 12 has a central axis that is operationally the same as the axis B associated with the receiver 10 when the shank upper portion 8 and the retainer 12 are installed within the receiver 10. The retainer 12 includes a substantially annular discontinuous body 115 having a substantially cylindrical outer surface 116. Extending upwardly and outwardly from the body 115, and integral thereto, is a superstructure that includes two sets of flexible panels or tangs, in particular, inner panels or tangs 117 and outer panels or tangs 118, the panels 117 and 118 extending upwardly in aligned pairs, allowing for lateral spaces between the pairs panels or tangs to provide clearance during assembly of the retainer 12 with the receiver 10 inner surfaces (see, e.g., FIGS. 24 and 25). The illustrated embodiment includes six pairs of inner and outer panels or tangs 117, 118, but it is foreseen that more or fewer panels or tangs may be used. The pairs of panels or tangs are generally equally spaced about the body 115. Also integral to the body 115 are six outer discontinuous cylindrical support surfaces 120, each surface 120 located beneath one of the outer panels 118. Below the surfaces 120, the cylindrical surface 116 forms a lower outer cylindrical skirt 121 broken only by a gap that will be described in greater detail below. The outer surface 116 is adjacent a bottom surface 122 and also includes portions 123 that are located between the outer panels 118. The surface portions 123 are illustrated as substantially planar, but may be cylindrical, generally having a diameter that is the same as the surface 116. At each of the panels 118, the surface 116 is adjacent to a ledge surface 124 that in turn is adjacent to one of the outer support surfaces 120. The lower skirt 121 and the ledge surfaces 124, as well as the surfaces 120 are receiver seating surfaces as will be described in greater detail below. In the illustrated embodiment, transition areas where the surface 116 meets the panels 117 and 118 or the retainer bottom 122 are curved or chamfered. Each body portion 123 is adjacent to a body top surface 126 that is substantially located between pairs of panels 117 and 118. Each top surface portion 126 is substantially planar and trapezoidal in outer profile.

Figure 4:
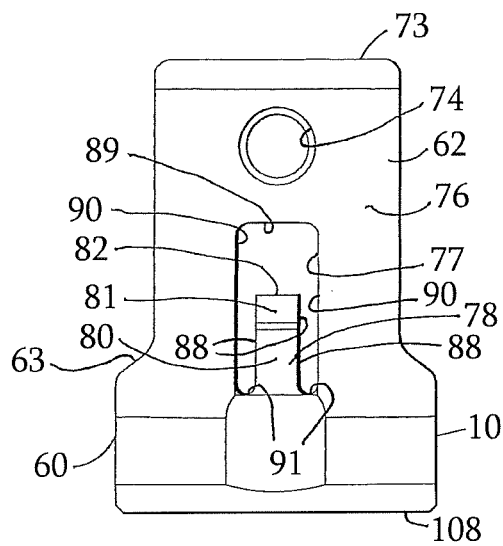
FIG. 4 is an enlarged side elevational view of the receiver of FIG. 1.
Figure 5:
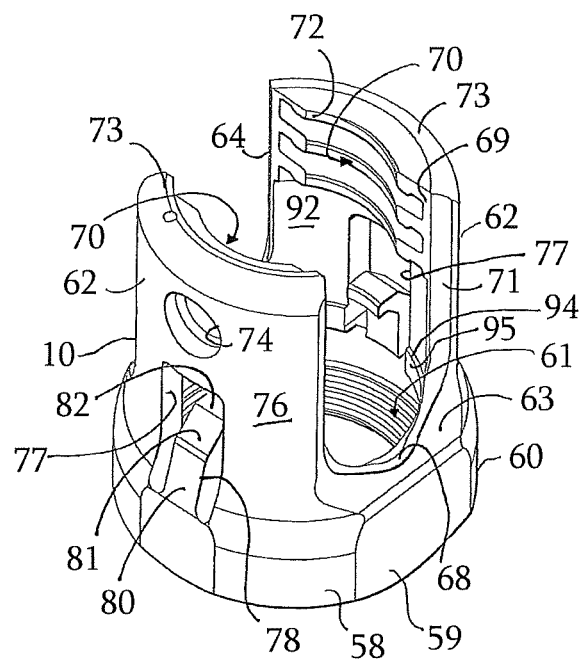
FIG. 5 is a perspective view of the receiver of FIG. 4.
Figure 6:
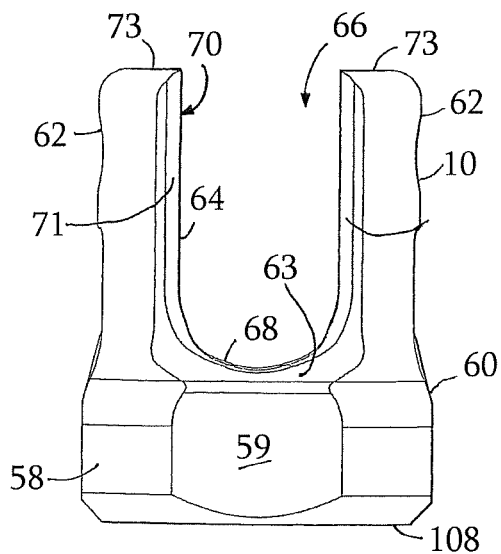
FIG. 6 is a front elevational view of the receiver of FIG. 4.
Figure 7:
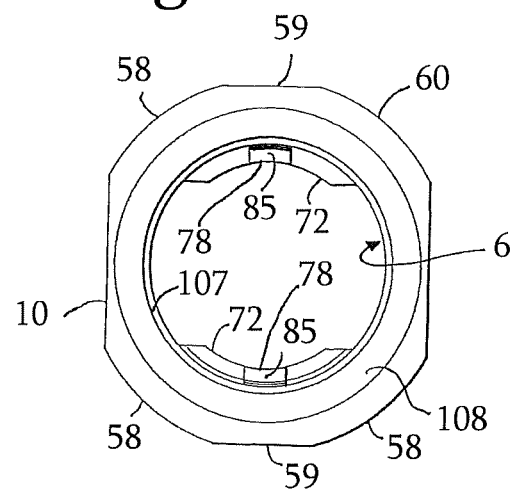
FIG. 7 is a bottom plan view of the receiver of FIG. 4.
Figure 8:
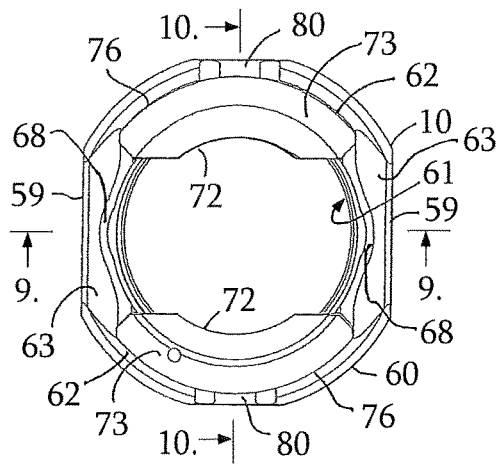
FIG. 8 is a top plan view of the receiver of FIG. 4.
Figure 9:
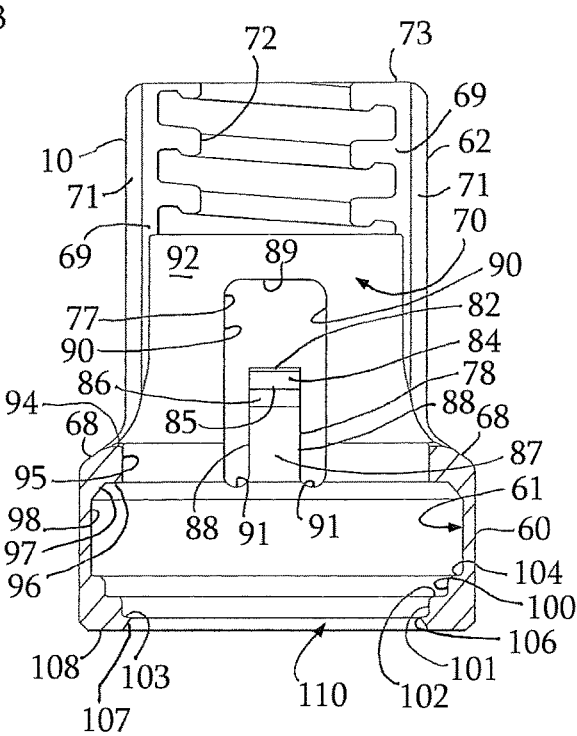
FIG. 9 is a cross-sectional view taken along the line 9-9 of FIG. 8.
Figure 10:
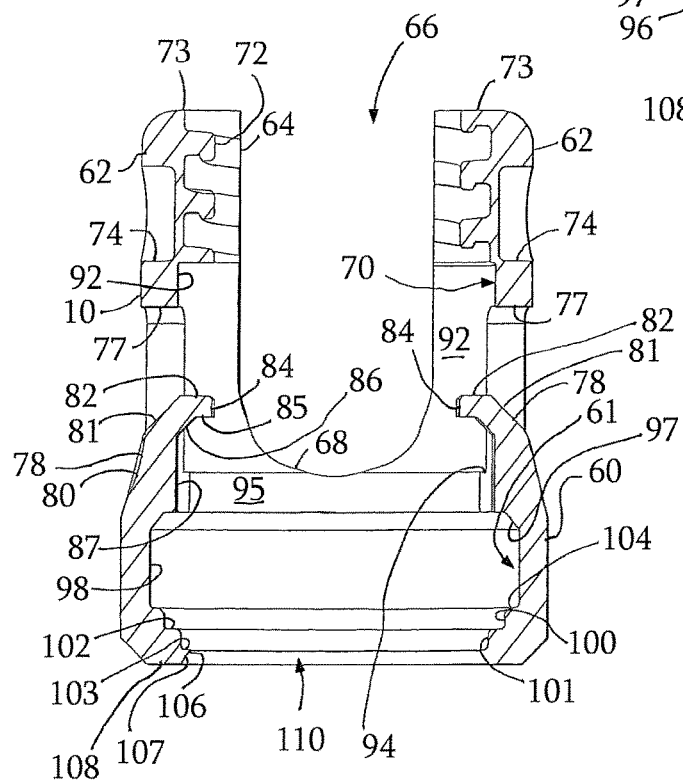
FIG. 10 is a cross-sectional view taken along the line 10-10 of FIG. 8.
Figure 11:
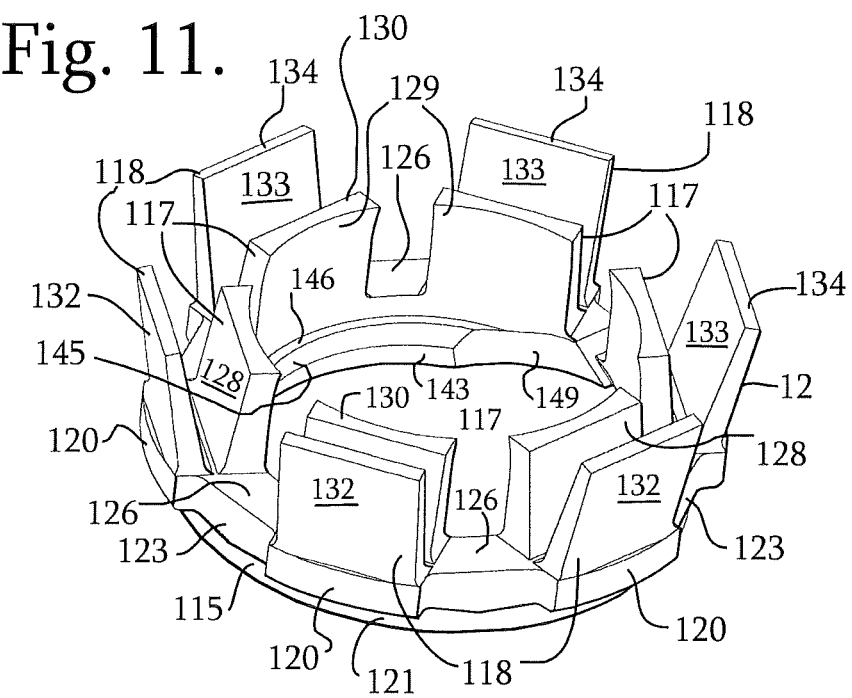
FIG. 11 is an enlarged perspective view of the retainer of FIG. 1.
Figure 12:
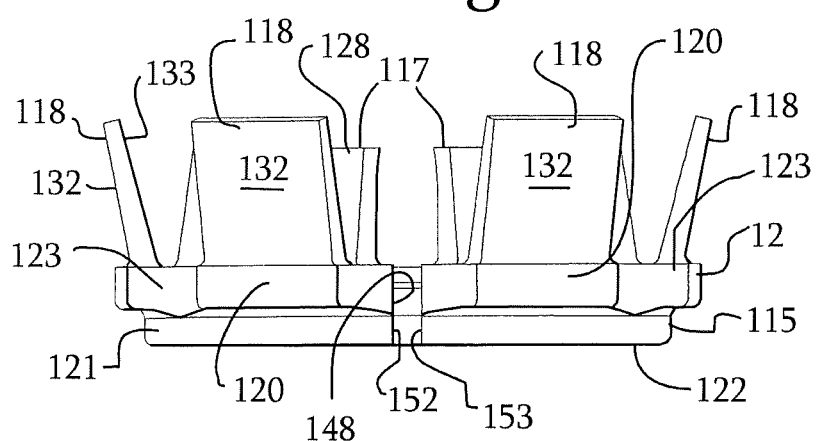
FIG. 12 is a front elevational view of the retainer of FIG. 11.
Figure 13:
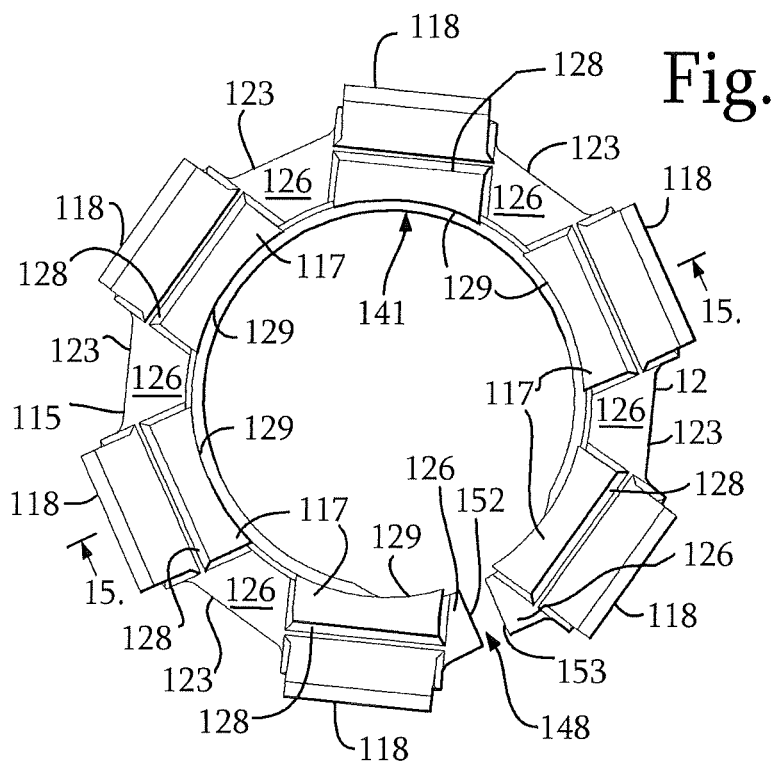
FIG. 13 is a top plan view of the retainer of FIG. 11.
Figure 14:
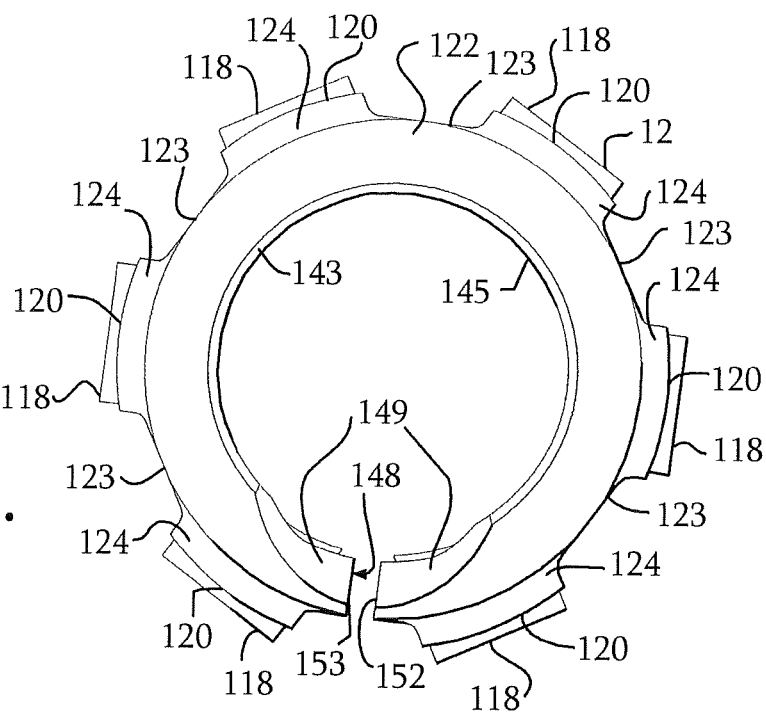
FIG. 14 is a bottom plan view of the retainer of FIG. 11.
Figure 17:
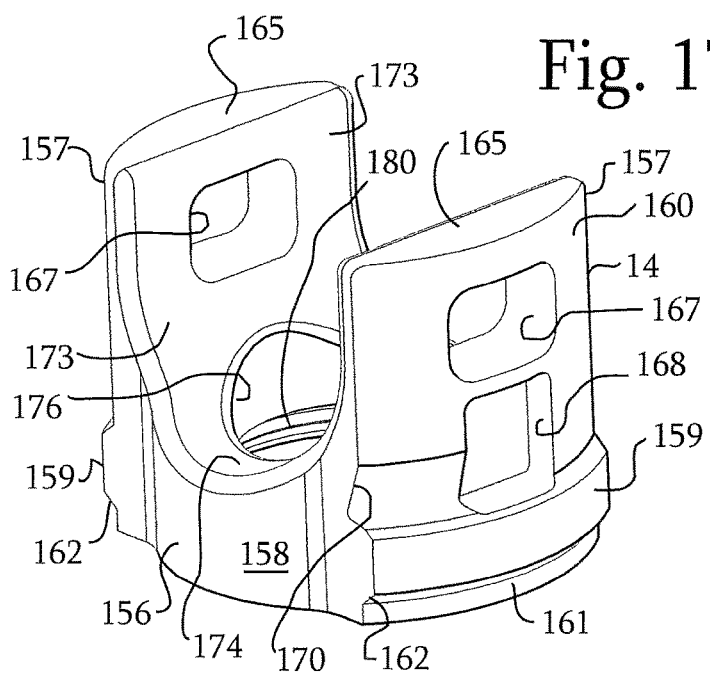
FIG. 17 is an enlarged perspective view of the insert of FIG. 1.
Figure 18:
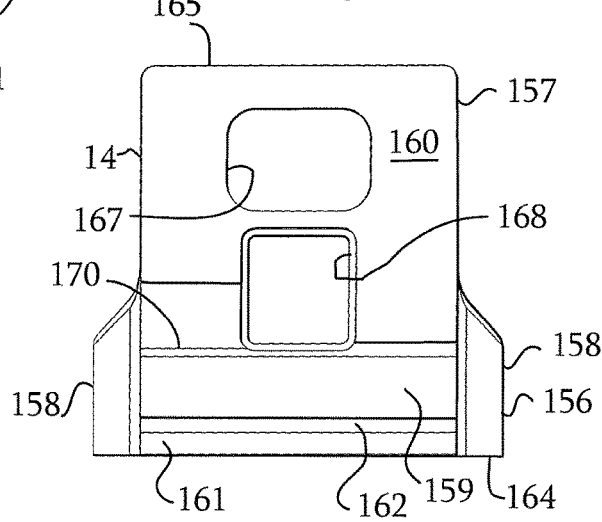
FIG. 18 is a side elevational view of the insert of FIG. 17.
Figure 19:
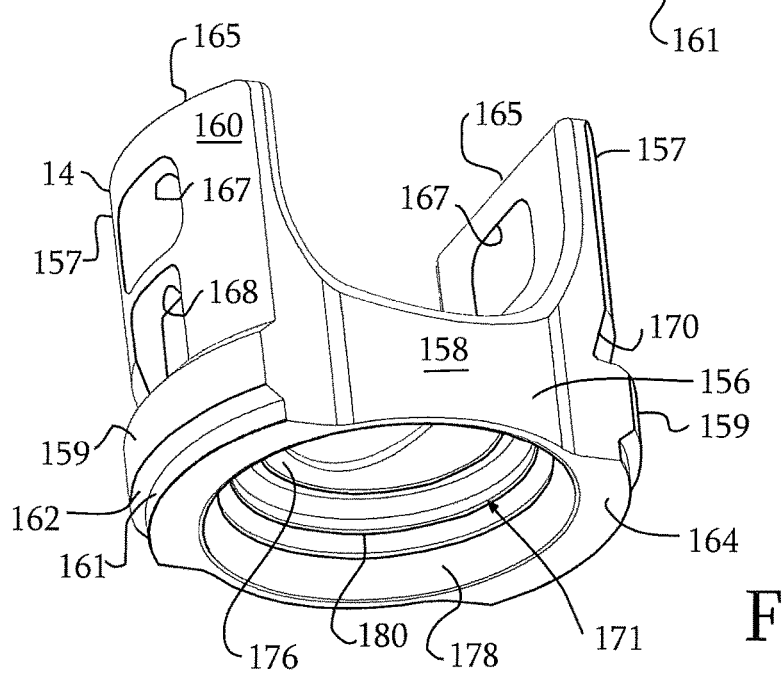
FIG. 19 is another perspective view of the insert of FIG. 17.
Figure 20:
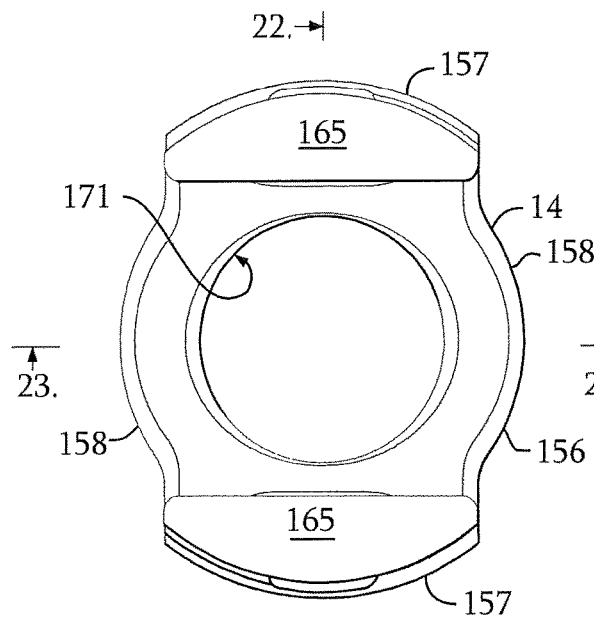
FIG. 20 is a top plan view of the insert of FIG. 17.
Figure 21:
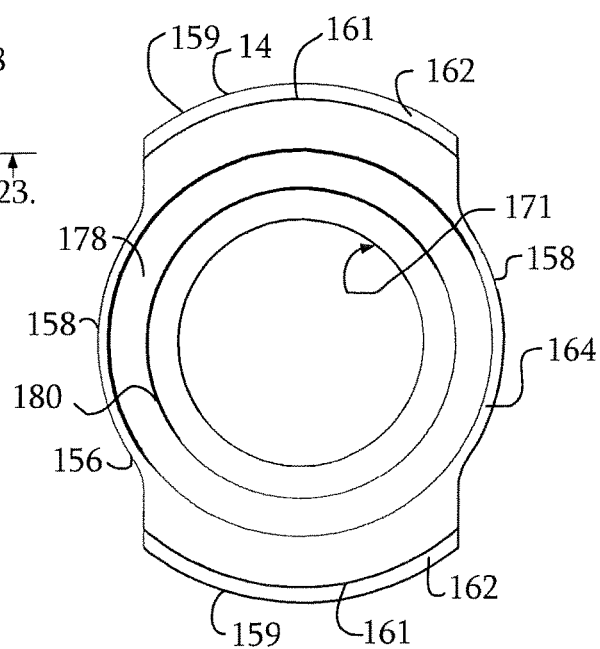
FIG. 21 is a bottom plan view of the insert of FIG. 17.
Figure 22:
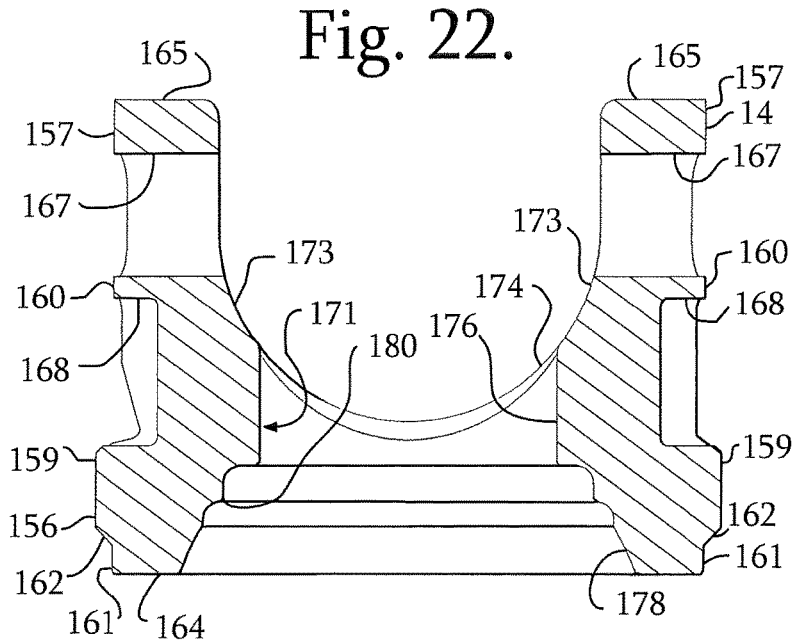
FIG. 22 is an enlarged cross-sectional view taken along the line 22-22 of FIG. 20.
Figure 23:
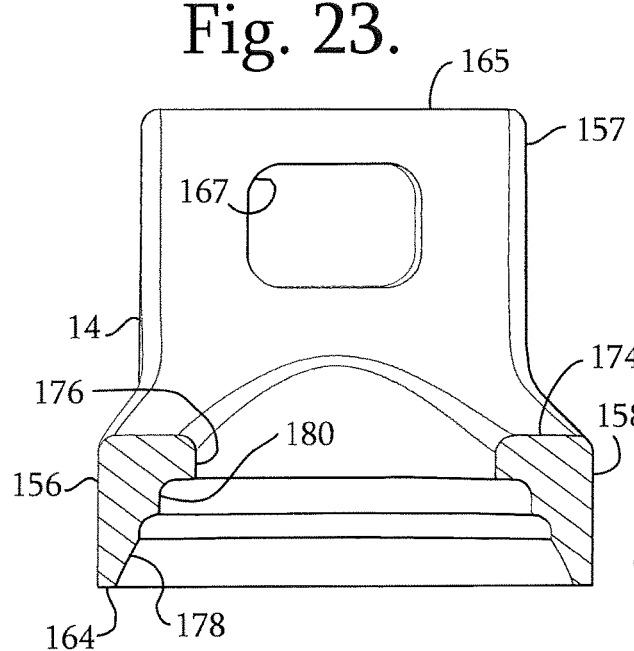
FIG. 23 is an enlarged cross-sectional view taken along the line 23-23 of FIG. 20.

The inner panels 117 each include a substantially planar outer surface 128 and a concave inner surface 129, the surfaces 129 each being partially radiused and partially cylindrical, making up a discontinuous curved surface sized and shaped for friction fit engagement with the shank head 8 as best shown in FIG. 13 and as will be described in greater detail below. However, it is foreseen that the panel inner surfaces 129 may also be planar or include edges or other surfaces features for gripping, but not locking the retainer 12 to the shank head 8 during assembly and manipulation, but prior to locking of the polyaxial mechanism of the bone screw assembly 1. The panels 117 generally slant inwardly towards the central axis of the retainer 12 and thus ultimately inwardly toward the shank head 8. Each panel 117 includes a top surface 130 that is substantially planar and runs substantially parallel to the bottom surface 122 when the retainer is in a neutral position such as that shown in FIG. 15.

The outer panels 118 each have a planar outer surface 132, a planar inner surface 133 and a planar top surface 134 that slopes at an oblique angle with respect to the retainer bottom surface 122. The surfaces 134 are perpendicular to adjacent surfaces 132. The panels 118 generally extend outwardly away from the panels 117 as well as outwardly and upwardly from the central axis of the retainer body 115. Each surface 133 faces an outer surface 128 of one of the panels 117. The body top surface 126 is reduced to a narrow strip between each pair of panels 117 and 118. The panels 117 and 118 are resilient, the panels being expandable about the shank head 8 and the panels 118 being compressible inwardly and resiliently holding against the receiver inner surfaces during shipping and certain assembly steps. The panels 118 then return to an original shape within the receiver cavity 61, capturing the retainer 12 within the receiver 10, but still allowing for rotation of the retainer 12 with respect to the receiver 10 about the receiver central axis B.

The retainer ring 12 is made from a resilient material, such as a stainless steel or titanium alloy, so that the retainer 12 body 115 may be expanded and the tabs or panels 117 and 118 of the retainer may be manipulated during various steps of assembly as will be described in greater detail below. The retainer 12 has a central channel or hollow through bore, generally 141, that passes entirely through the retainer 12 from the inner panel top surfaces 130 to the bottom surface 122 of the retainer body 115. Surfaces that define the channel or bore 141 at the body 115 include a discontinuous inner lower frusto-conical surface 143 adjacent to the retainer body bottom surface 122, a discontinuous, narrow substantially cylindrical surface 145 adjacent the frusto-conical surface 143 and a discontinuous annular step 146 located adjacent the cylindrical surface 145, the surface 146 being substantially parallel to the bottom surface 122 and extending between the surface 145 and a lower cylindrical portion 129' of the inner surface 129 that partially forms the inner panels 117. The surfaces 145 and 146 terminate at an edge 147 that is positioned and configured to engage the shank surface 34 as will be described in greater detail below. The inner cylindrical surface 129' adjacent the step 146 forms a continuous inner cylindrical wall except at a slit, generally 148 that runs through the body 115. The slit 148 creates a split or open ring retainer 12, the slit cutting entirely through the retainer body 115. In some embodiments, such a slit may run obtuse to the bottom surface 122. In the illustrated embodiment, the slit 148 runs substantially perpendicular to the surfaces 122. The slit 148 is primarily for expansion of the retainer 12 during pop-on or snap-on assembly with the shank head 8. However, the slit 148 also compresses during assembly with the receiver 10 as will be described in greater detail below. The slit 148 extends between the body top surface 126 and the bottom surface 122 and is located substantially centrally between two pairs of panels 117 and 118. Furthermore, at the location of the slit 148, a curved concave, cut-out surface 149 is formed in the bottom surface 122 and the frusto-conical surface 143. The cut-out surface 149 also extends into the cylindrical surface 145 and removes a portion of the step 146 at either side of the slit 148. The surface 149 is radiused or otherwise curved for engagement with the shank head 8 at the surface 34 as will be described in greater detail below. In the illustrated embodiment, the cut-out surface 149 is located substantially equally on either side of the slit 148 to provide for a desirable increased angle of orientation between the shank 8 and the retainer 12 and thus a desirable increased angle of articulation between the shank 8 and the receiver 10. The rotatability of the semi-constrained retainer 12 with respect to the receiver 10 allows for manipulation and placement of such an increased angle of articulation to a location desired by a surgeon. The through slit 148 of the resilient retainer 12 is defined by first and second end surfaces, 152 and 153 disposed in substantially parallel spaced relation to one another when the retainer is in a neutral or nominal state. Both end surfaces 152 and 153 are disposed perpendicular to the bottom surface 122, but in some embodiments may be disposed at an obtuse angle thereto. A width between the surfaces 152 and 153 is narrow to provide stability to the retainer 12 during operation, but wide enough to allow for some compression of the retainer during assembly as will be described in greater detail below. Because the retainer 12 is top loadable in a substantially neutral state and ultimately expands during locking of the polyaxial mechanism, the width of the slit 148 may be much smaller than might be required for a bottom loaded compressible retainer ring. It has been found that once the retainer 12 is expanded about the shank head 8, the retainer 12 may return to a new nominal or neutral orientation in which a gap between the surfaces 152 and 153 is slightly greater than the gap shown in the nominal state of FIG. 12, for example. As will be described in greater detail below, the assembly 1 advantageously provides for access to the insert 14 and the retainer 12 to allow for pressing of the retainer 12 down onto the receiver seat portions and reducing the retainer 12 into the receiver 10 inner cylindrical surfaces as desired, prior to locking of the assembly 1 with a rod and closure top.

With particular reference to FIGS. 1 and 17-23, the locking compression insert 14 is illustrated that is sized and shaped to be received by and down-loaded into the receiver 10 at the upper opening 66. The compression insert 14 has an operational central axis that is the same as the central axis B of the receiver 10. In operation, the insert advantageously frictionally engages the bone screw shank upper portion 8 as well as engaging the receiver 10 in an interference fit engagement, locking the shank 4 in a desired angular position with respect to the receiver 10 that remains in such locked position even if, for example, a rod and closure top are later removed and the rod is replaced with another rod or other longitudinal connecting member or member component, such as one of the sleeves shown in FIGS. 52-72. Such locked position may also be released by the surgeon if desired with insert engaging tools (not shown). As will be described in greater detail below with respect to the alternative insert 214 shown in FIGS. 47-51, in some embodiments of the invention, the insert does not have the receiver interference fit feature. The locking insert 14 as well as the non-locking insert 214 are preferably made from a solid resilient material, such as a stainless steel or titanium alloy, so that portions of the insert may be grasped, pinched or pressed, if necessary, and un-wedged from the receiver 10 with a release tool (not shown).

The locking compression insert 14 includes a body 156 with cylindrical surfaces of a variety of diameters, the body 156 being integral with a pair of upstanding arms 157. Located between the arms 157, the body 156 has an outer substantially cylindrical surface 158. Located beneath each upstanding arm 157 is a discontinuous, cylindrical, interference fit surface 159 that extends outwardly from an arm and body outer substantially cylindrical surface 160, a diameter of the surface 159 being larger than a diameter of the surface 160. Beneath each surface 159 is a discontinuous cylindrical surface 161 having a diameter the same or similar to the surface 160. A frusto-conical or curved transition surface or ledge 162 spans between each surface 159 and the corresponding lower cylindrical surface 161. The lower surface 161 is also adjacent a substantially planar and annular bottom surface 164. The insert 14 further includes substantially planar arm top surfaces 165 located opposite the bottom surface 164. A rectangularly shaped, substantially centrally located tool receiving aperture 167 is formed in each arm surface 160 near each top surface 165, the aperture 167 extending completely through the respective arm 157. The through apertures 167 located directly across from one another advantageously allow for grasping the insert 14 with a tool either at the outside surfaces 160 or the inside surfaces of the arms 157. Located directly below each aperture 167 is a shallow aperture 168, also located centrally on the arm surface 160, the aperture 168 also being adjacent the interference fit surface 159. The apertures 168 are substantially square in profile and do not extend entirely through the arm surface 160. Running from each aperture 168 is a groove 170, sized and shaped to receive and slidingly engage a receiver holding tab 78 during assembly of the insert 14 with the receiver 10 when the insert 14 is rotated into place, as shown, for example, in FIGS. 29 and 30, the aperture 168 ultimately capturing a respective tab 78 as will be described in greater detail below.

Turning to the inner surfaces of the insert 15, a through bore, generally 171, is disposed primarily within and through the body 156 and communicates with a generally U-shaped through channel formed by a saddle surface 173 that is substantially defined by the upstanding arms 157. Near the top surfaces 165, the saddle surface 173 is substantially planar, with the through apertures 167 extending therethrough. The saddle 173 has a lower seat 174 sized and shaped to closely, snugly engage the rod 21 or other longitudinal connecting member. It is foreseen that an alternative embodiment may be configured to include planar holding surfaces that closely hold a square or rectangular bar as well as hold a cylindrical rod-shaped, cord, or sleeved cord longitudinal connecting member. The arms 157 disposed on either side of the channel extend upwardly and outwardly from the body 156 and terminate at the top surfaces 165. The arms 157 are sized and configured for ultimate placement beneath the receive guide and advancement structure 72. It is foreseen that in some embodiments of the invention, the arms may be extended upwardly and the closure top configured such that the arms and, more specifically, the surfaces 165 ultimately directly engage the closure top 18 for locking of the polyaxial mechanism, for example, when the rod 21 is made from a deformable material. In such embodiments, the insert 14 may include an additional rotation blocking structure or feature that abuts against cooperating structure located on an inner wall of the receiver 10, preventing rotation of the insert with respect to the receiver when the closure top is rotated into engagement with the insert. In the illustrated embodiment, the surfaces 165 are ultimately positioned in spaced relation with the closure top 18, so that the closure top 18 frictionally engages the rod 21 only, pressing the rod 21 downwardly against the seating surface 174, the insert 14 in turn pressing against the shank 4 upper portion 8 that presses against the retainer 12 to lock the polyaxial mechanism of the bone screw assembly 1 at a desired angle.

The bore, generally 171, is substantially defined at the body 156 by an inner cylindrical surface 176 that communicates with the seat 174 and a lower concave substantially radiused or partially spherical surface 178 having a radius the same or substantially similar to a radius of the surface 34 of the shank upper portion 8. The surface 178 terminates at the base surface 164. Located between the cylindrical surface 176 and the radiused surface 178 or located along the radiused surface 178 is a shank gripping surface portion, generally 180. The gripping surface portion 180 includes one or more stepped surfaces or ridges sized and shaped to grip and penetrate into the shank head 8 when the insert 14 is locked against the head surface 34. It is foreseen that the stepped surface portion 180 may include greater or fewer number of stepped surfaces. It is foreseen that the shank gripping surface portion 180 and also the spherical surface 178 may additionally or alternatively include a roughened or textured surface or surface finish, or may be scored, knurled, or the like, for enhancing frictional engagement with the shank upper portion 8.

The compression insert 14 through bore 171 is sized and shaped to receive a driving tool (not shown) therethrough that engages the shank drive feature 46 when the shank body 6 is driven into bone with the receiver 10 attached. Also, in some locking embodiments of the invention, the bore receives a manipulation tool (not shown) used for releasing the insert from a locked position with the receiver, the tool pressing down on the shank and also gripping the insert at the through bores 167 located in the arms or with other tool engaging features. For example, a manipulation tool for releasing the insert from the receiver 10 may also access such bores 167 from the receiver through the apertures 77 in the receiver. Thereby, tools can be configured to release a locking insert from the inside and outside of the receiver 10. Each of the arms 157 and the insert body 156 may include more surface features, such as cut-outs notches, bevels, etc. to provide adequate clearance for inserting the insert 14 into the receiver and cooperating with the retainer 12 during the different assembly steps as will be described in greater detail below.

The insert body 156 cylindrical surface 158 has a diameter slightly smaller than a diameter between crests of the guide and advancement structure 72 of the receiver 10, allowing for top loading of the compression insert 14 into the receiver opening 66, with the arms 157 of the insert 14 being located between the receiver arms 62 during insertion of the insert 14 into the receiver 10. Once the arms 157 of the insert 14 are generally located beneath the guide and advancement structure 72, the insert 14 is rotated in a clockwise direction into place about the receiver axis B until the receiver holding tabs 78 are located in the apertures 168 as will be described in greater detail below.

With reference to FIGS. 1 and 36-37, the illustrated elongate rod or longitudinal connecting member 21 (of which only a portion has been shown) can be any of a variety of implants utilized in reconstructive spinal surgery, but is typically a cylindrical, elongate structure having the outer substantially smooth, cylindrical surface 22 of uniform diameter. The rod 21 may be made from a variety of metals, metal alloys, non-metals and deformable and less compressible plastics, including, but not limited to rods made of elastomeric, polyetheretherketone (PEEK) and other types of materials, such as polycarbonate urethanes (PCU) and polyethelenes.

Longitudinal connecting members for use with the assembly 1 may take a variety of shapes, including but not limited to rods or bars of oval, rectangular or other curved or polygonal cross-section. The shape of the insert 14 may be modified so as to closely hold the particular longitudinal connecting member used in the assembly 1. Some embodiments of the assembly 1 may also be used with a tensioned cord as will be described in greater detail with reference to FIGS. 52-74. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the compression insert 14 of the receiver having a U-shaped, rectangular- or other-shaped channel, for closely receiving the longitudinal connecting member. The longitudinal connecting member may be integral or otherwise fixed to a bendable or damping component that is sized and shaped to be located between adjacent pairs of bone screw assemblies 1, for example. A damping component or bumper may be attached to the longitudinal connecting member at one or both sides of the bone screw assembly 1. A rod or bar (or rod or bar component) of a longitudinal connecting member may be made of a variety of materials ranging from deformable plastics to hard metals, depending upon the desired application. Thus, bars and rods of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 1 and 36-37, the closure structure or closure top 18 shown with the assembly 1 is rotatably received between the spaced arms 62 of the receiver 10. It is noted that the closure 18 top could be a twist-in or slide-in closure structure. The illustrated closure structure 18 is substantially cylindrical and includes a an outer helically wound guide and advancement structure 182 in the form of a flange that operably joins with the guide and advancement structure 72 disposed on the arms 62 of the receiver 10. The flange form utilized in accordance with the present invention may take a variety of forms, including those described in Applicant's U.S. Pat. No. 6,726,689, which is incorporated herein by reference. Although it is foreseen that the closure structure guide and advancement structure could alternatively be a buttress thread, a square thread, a reverse angle thread or other thread like or non-thread like helically wound advancement structure, for operably guiding under rotation and advancing the closure structure 18 downward between the arms 62 and having such a nature as to resist splaying of the arms 62 when the closure structure 18 is advanced into the channel 64, the flange form illustrated herein as described more fully in Applicant's U.S. Pat. No. 6,726,689 is preferred as the added strength provided by such flange form beneficially cooperates with and counters any reduction in strength caused by the any reduced profile of the receiver 10 that may more advantageously engage longitudinal connecting member components. The illustrated closure structure 18 also includes a top surface 184 with an internal drive 186 in the form of an aperture that is illustrated as a hex drive, or may be, for example, a star-shaped internal drive such as that sold under the trademark TORX or other internal drives such as slotted, tri-wing, spanner, two or more apertures of various shapes, and the like. A driving tool (not shown) sized and shaped for engagement with the internal drive 186 is used for both rotatable engagement and, if needed, disengagement of the closure 18 from the receiver arms 62. It is also foreseen that the closure structure 18 may alternatively include a break-off head designed to allow such a head to break from a base of the closure at a preselected torque, for example, 70 to 140 inch pounds. Such a closure structure would also include a base having an internal drive to be used for closure removal. A base or bottom surface 188 of the closure is planar and further includes a point 189 and a rim 190 for engagement and penetration into the surface 22 of the rod 21 in certain embodiments of the invention. It is noted that in some embodiments, the closure top bottom surface 188 does not include the point and/or the rim. The closure top 18 may further include a cannulation through bore (not shown) extending along a central axis thereof and through the top and bottom surfaces thereof. Such a through bore provides a passage through the closure 18 interior for a length of wire (not shown) inserted therein to provide a guide for insertion of the closure top into the receiver arms 62. An alternative closure top, such as the top 18' shown in FIGS. 39 and 40 for use with a deformable rod, such as a PEEK rod 21', for example, includes a bottom surface 188' that has domed portion 190' with a central nub 189' in lieu of the point and rim surface of the closure top 18. Otherwise, the closure top 18' includes a guide and advancement structure 182', a top surface 184' and an internal drive feature 186' the same or substantially similar to the respective guide and advancement structure 182, top surface 184 and internal drive feature 186 of the closure top 18.

The assembly 1 receiver 10, retainer 12 and compression insert 14 are typically assembled at a factory setting that includes tooling for holding and alignment of the component pieces and manipulating the retainer 12 and the insert 14 with respect to the receiver 10. In some circumstances, the shank 4 is also assembled with the receiver 10, the retainer 12 and the compression insert 14 at the factory. In other instances, it is desirable to first implant the shank 4, followed by addition of the pre-assembled receiver, retainer and compression insert at the insertion point. In this way, the surgeon may advantageously and more easily implant and manipulate the shanks 4, distract or compress the vertebrae with the shanks and work around the shank upper portions or heads without the cooperating receivers being in the way. In other instances, it is desirable for the surgical staff to pre-assemble a shank of a desired size and/or variety (e.g., surface treatment of roughening the upper portion 8 and/or hydroxyapatite on the shank 6), with the receiver, retainer and compression insert. Allowing the surgeon to choose the appropriately sized or treated shank 4 advantageously reduces inventory requirements, thus reducing overall cost and improving logistics and distribution.

Figure 24:
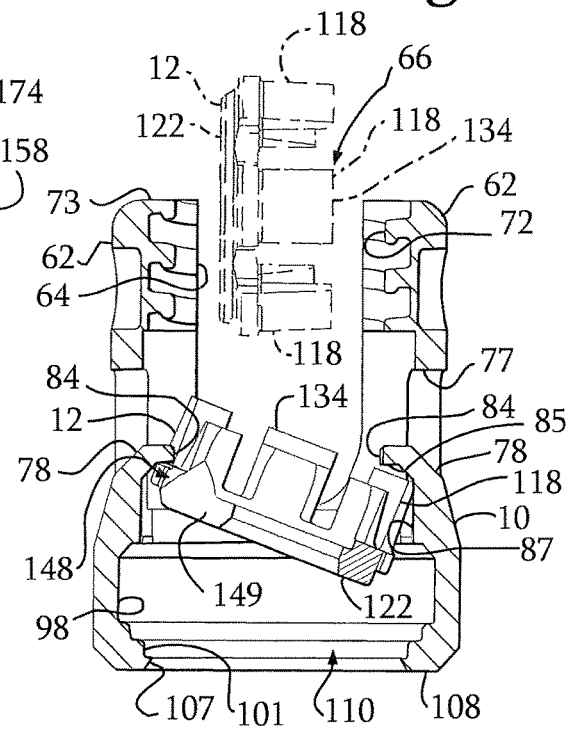
FIG. 24 is an enlarged front elevational view of the retainer and receiver of FIG. 1 with portions of the receiver broken away to show the detail thereof, the retainer being shown downloaded into the receiver (in phantom) to a partially inserted stage of assembly.
Figure 25:
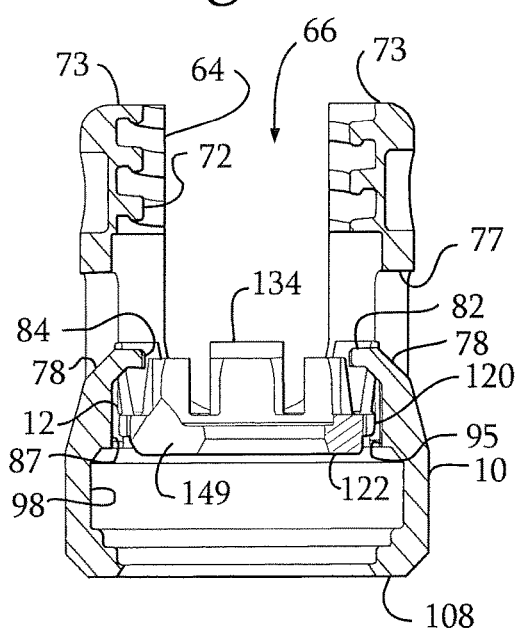
FIG. 25 is a front elevational view of the retainer and receiver with portions broken away, similar to what is shown in FIG. 24, showing the retainer in a subsequent stage of assembly and in a maximum state of compression.
Figure 26:
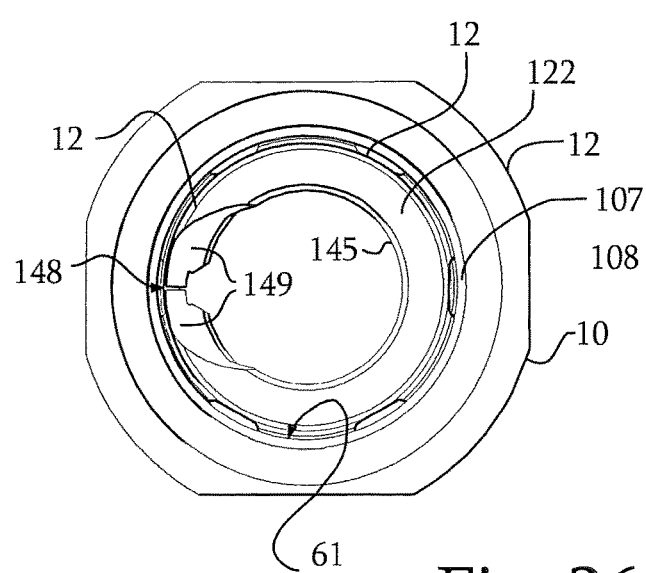
FIG. 26 is a bottom plan view of the receiver and retainer of FIG. 25.

Pre-assembly of the receiver 10, retainer 12 and compression insert 14 is shown in FIGS. 24-30. With particular reference to FIG. 24, first the retainer 12 is inserted into the upper receiver opening 66, leading with the outer panels 118 with the panel 118 top surfaces 134 facing one arm 62 and the retainer bottom surface 122 facing the opposing arm 62 (shown in phantom). The retainer 12 is then lowered in such sideways manner into the channel 64 and partially into the receiver cavity 61, followed by tilting the retainer 12 such that at least one panel top surface 134 is located beneath the surface 85 of one of the receiver holding tabs 78 and the opposed holding tab 78 is located generally between a pair of panels 118, for example, at or near the retainer slit 148 as shown in solid lines in FIG. 24. Then, with reference to FIG. 25, the retainer 12 is tilted into a position wherein the central axis of the retainer 12 is generally aligned with the receiver central axis B and the receiver holding tabs 78 are each located between pairs of adjacent panels 118 and extend over retainer body top surfaces 126 located opposite one another, with each tab surface 85 being located directly above a top surface 126 or the slit 148. FIG. 26 shows a bottom plan view of the receiver and retainer at the intermediate stage of assembly shown in FIG. 25, illustrating how the cut-out portion 149 of the retainer 12 is located generally inward of the inner surfaces making up the receiver cavity 61. FIGS. 25 and 26 also illustrate the retainer 12 at a compressed state with the slit surfaces 152 and 153 being at a near touching state so that the cylindrical surfaces 120 slide past the receiver inner surface 95.

Figure 27:
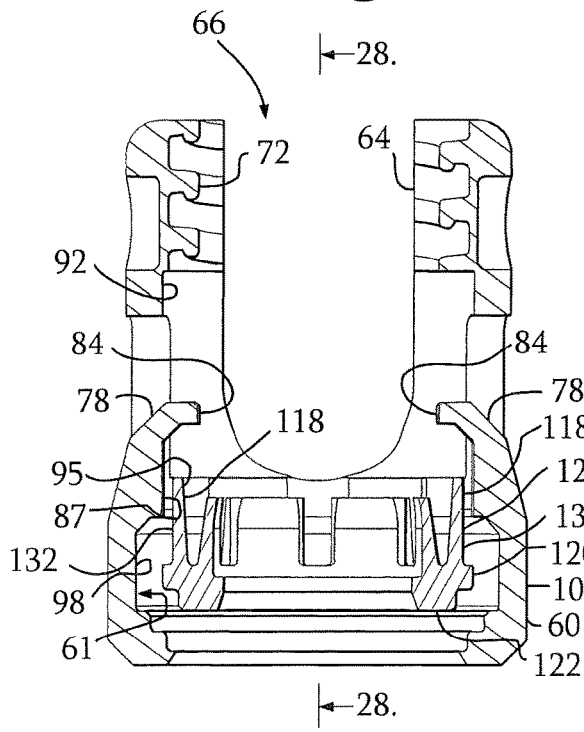
FIG. 27 is an enlarged front elevational view of the retainer and receiver with portions broken away, similar to what is shown in FIG. 25, showing the retainer positioned below the receiver spring tabs and also rotated about a central axis thereof, such rotation not necessary for assembly but provided herein to aid in viewing the drawings.
Figure 28:
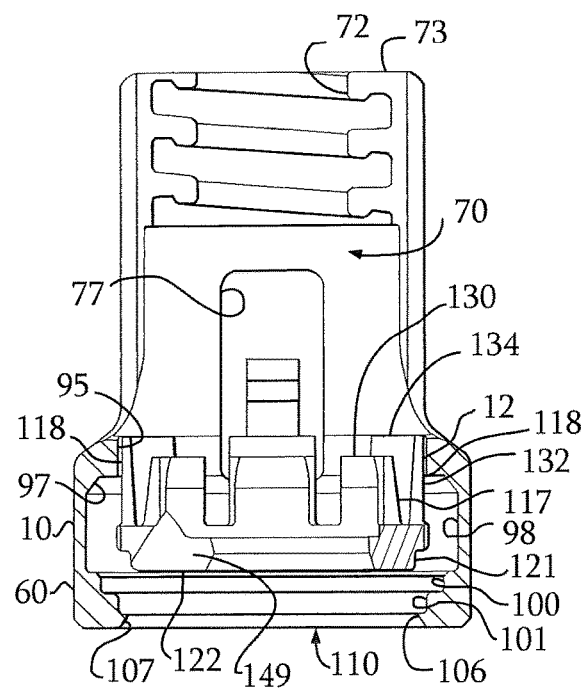
FIG. 28 is a cross-sectional view taken along the line 28-28 of FIG. 27.

With reference to FIGS. 27 and 28, after the panels 118 are located between holding tabs 78, the retainer 12 is lowered into the receiver cavity 61 with the resilient panels 118 being pressed inwardly, using tooling, or by the use of a downward force that results in compression of the panels 118 toward the axis B due to engagement with the receiver surfaces 95. It is noted that the retainer 12 shown in FIG. 27, has been rotated about the receiver axis B from the position shown in FIG. 25. Such rotation is not required prior to downloading the retainer into the receiver cavity 61, but has been illustrated here to provide the reader with a cross-sectional view of the retainer 12 that more clearly shows the position and orientation of the retainer panels 117 and 118 with respect to the receiver cavity surfaces. With further reference to FIG. 28, the retainer 12 is pressed downwardly until the retainer is in a desired temporary position within the receiver 10 with panel 118 outer surfaces 132 engaging the receiver inner surfaces 95, thereby holding the retainer 12 within the receiver at such location during loading and initial assembly of the insert 14 into the receiver 10. At this time, the retainer 12 is not yet fully captured within the receiver base cavity 61, but cannot be readily removed unless the panels 118 are squeezed toward one another using a tool or tools.

Figure 29:
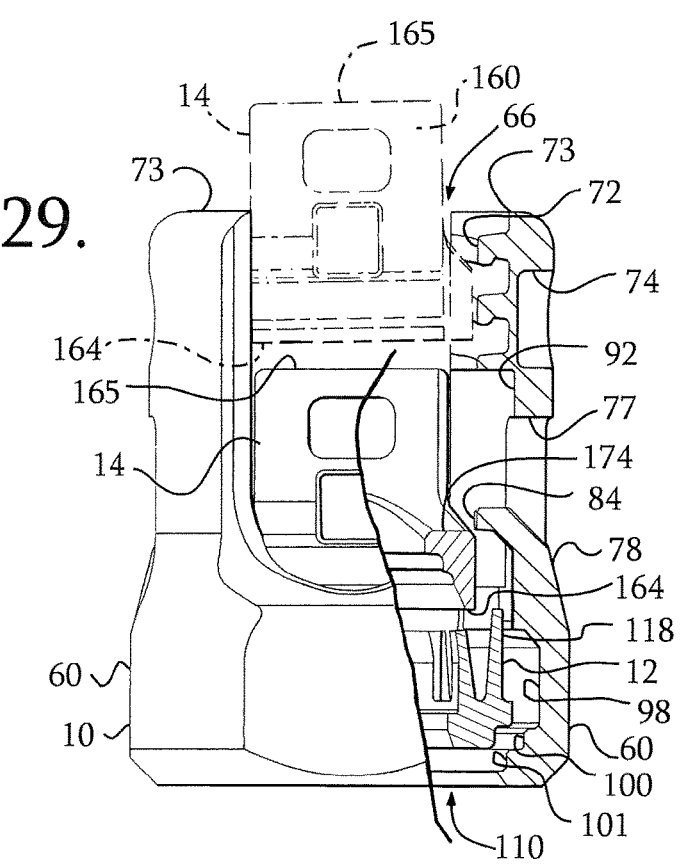
FIG. 29 is an enlarged front elevational view of the retainer and receiver with portions broken away, similar to what is shown in FIG. 27, showing the retainer in a slightly lower position within the receiver and further including the insert in side elevation, in phantom, being downloaded into the receiver and the insert shown in solid lines with portions broken away when at a location suitable for rotation within the receiver.
Figure 30:
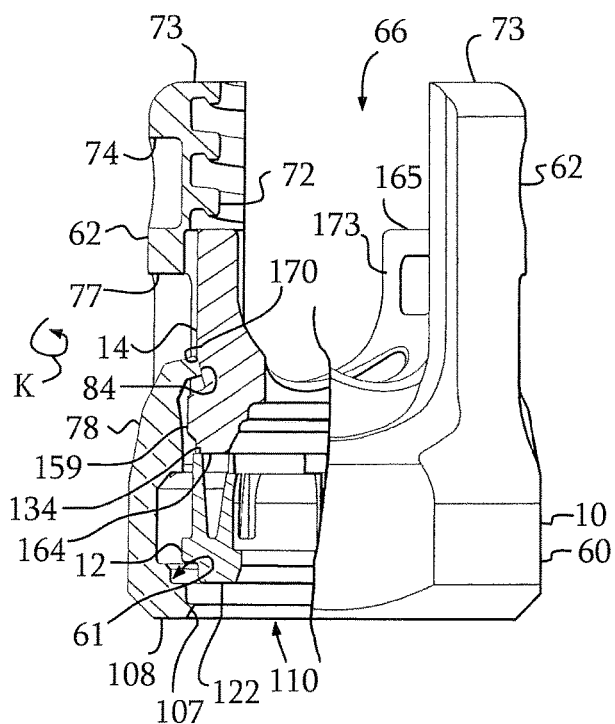
FIG. 30 is a front elevational view of the retainer and receiver with portions broken away, similar to what is shown in FIG. 29, further showing the insert being partially rotated within the receiver with receiver spring tabs being pushed outwardly during such rotation.

With reference to FIGS. 29-31, the compression insert 14 is then downloaded into the receiver 10 through the upper opening 66 with the bottom surface 164 facing the receiver arm top surfaces 73 and the insert arm outer surfaces 160 located between the opposed receiver arms 62. The insert 14 is then lowered toward the receiver base 60 until the insert 14 arm upper surfaces 165 are adjacent the run-out area below the guide and advancement structure 72 defined in part by the cylindrical surface 92. Thereafter, the insert 14 is rotated (see the arrow K in FIG. 30) about the receiver axis B until the upper arm surfaces 165 are directly below the guide and advancement structure 72 with the U-shaped channel 173 of the insert 14 aligned with the U-shaped channel 64 of the receiver 10. In some embodiments, the insert arms may need to be compressed slightly during rotation to clear some of the inner surfaces 70 of the receiver arms 62. With particular reference to FIGS. 30 and 31, as the insert 14 is rotated about the axis B, the receiver holding tab surfaces 84 slide along the insert groove surfaces 170 and then are captured with the insert apertures 168. The insert apertures 168 help retain the desired alignment between the insert 14 and the receiver 10 and prohibit relative rotation between the two parts. However, relative vertical movement between the insert 14 and the receiver 10 is possible as the apertures 168 do not vertically fix the insert with respect to the receiver. At this time also, the insert bottom surface 164 is resting on the top surfaces 134 of the panels 118. However, the frictional engagement between the panels 118 and the receiver inner surfaces 95 prohibit the retainer 12 and thus also the insert 14 from dropping further down into the receiver 10 cavity 61. The retainer 12 and the insert 14 are now in a desired position for shipping as an assembly along with the separate shank 4. The insert 14 is also fully captured within the receiver 10 by the guide and advancement structure 72 prohibiting movement of the insert 14 up and out through the receiver opening 66 as well as by retainer 12 located below the insert.

Typically, the receiver and retainer combination are shipped or otherwise provided to the end user with the spring-like panels 118 wedged against the receiver as shown in FIG. 31. The receiver 10, retainer 12 and insert 14 combination is now pre-assembled and ready for assembly with the shank 4 either at the factory, by surgery staff prior to implantation, or directly upon an implanted shank 4 as will be described herein.

As illustrated in FIG. 31, the bone screw shank 4 or an entire assembly 1 made up of the assembled shank 4, receiver 10, retainer 12 and compression insert 14, is screwed into a bone, such as the vertebra 17 (shown in phantom), by rotation of the shank 4 using a suitable driving tool (not shown) that operably drives and rotates the shank body 6 by engagement thereof at the internal drive 46. Specifically, the vertebra 17 may be pre-drilled to minimize stressing the bone and have a guide wire (not shown) inserted therein to provide a guide for the placement and angle of the shank 4 with respect to the vertebra. A further tap hole may be made using a tap with the guide wire as a guide. Then, the bone screw shank 4 or the entire assembly 1 is threaded onto the guide wire utilizing the cannulation bore 50 by first threading the wire into the opening at the bottom 28 and then out of the top opening at the drive feature 46. The shank 4 is then driven into the vertebra using the wire as a placement guide. It is foreseen that the shank and other bone screw assembly parts, the rod 21 (also having a central lumen in some embodiments) and the closure top 18 (also with a central bore) can be inserted in a percutaneous or minimally invasive surgical manner, utilizing guide wires and attachable tower tools mating with the receiver. When the shank 4 is driven into the vertebra 17 without the remainder of the assembly 1, the shank 4 may either be driven to a desired final location or may be driven to a location slightly above or proud to provide for ease in assembly with the pre-assembled receiver, compression insert and retainer.

Figure 32:
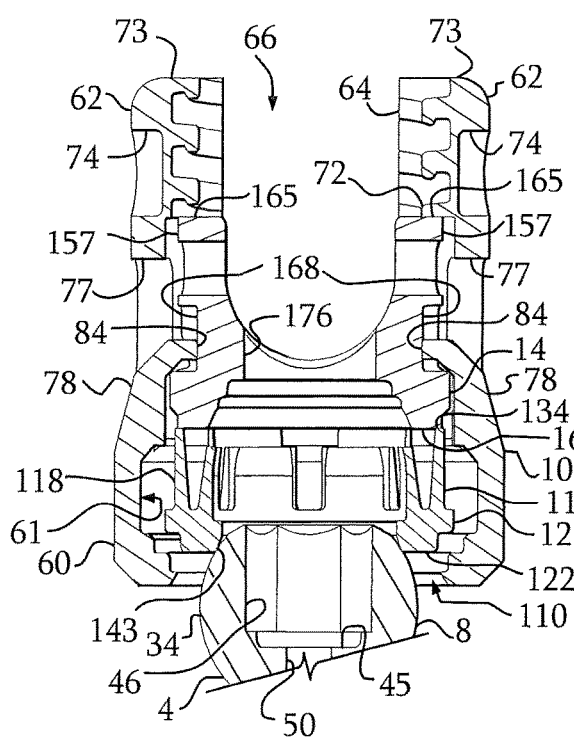
FIG. 32 is an enlarged and partial front elevational view with portions broken away, similar to FIG. 31, and further showing the shank in a first stage of assembly with the receiver and retainer.
Figure 33:
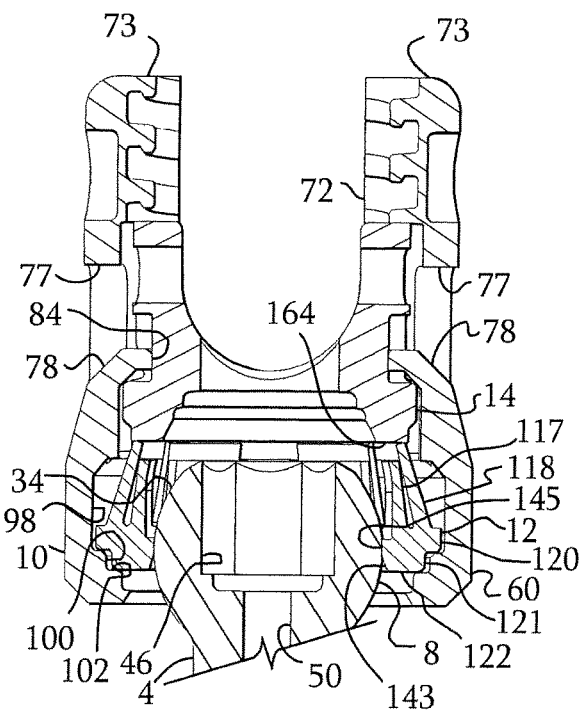
FIG. 33 is an enlarged and partial front elevational view with portions broken away, similar to FIG. 32, showing the retainer lower portion in an expanded state about a midportion of the shank head.

With reference to FIG. 32, the pre-assembled receiver, insert and retainer are placed above the shank upper portion 8 until the shank upper portion is received within the opening 110. With particular reference to FIGS. 32-35, as the shank upper portion 8 is moved into the interior 61 of the receiver base, the shank upper portion 8 presses upwardly against the retainer 12 in the receiver recess partially defined by the cylindrical surface 98. As the shank head 8 continues to move upwardly toward the channel 64, the shank head surface 34 forces the retainer 12 against the insert 14. However, the insert 14 is prohibited from moving upward by the receiver guide and advancement structure 72. Therefore, the upwardly moving shank head 8 forces a widening of the retainer slit 148 and corresponding outward movement of the body 115 of the retainer 12 towards the receiver cylindrical surfaces 98 and 100 defining the receiver expansion recess or chamber as best shown in FIG. 33, while the retainer panels 118 near the top surfaces 134 thereof are generally maintained in a location directly below the insert 14 bottom surface 164. At this time, the spherical surface 34 of the head 8 comes into contact with the retainer inner cylindrical body 145 and the edge 147. With reference to FIG. 34. With reference to FIG. 34, the retainer 12 begins to return towards a neutral or nominal state as the center of the sphere of the shank head 8 passes beyond the retainer surface 147. By the time the hemisphere of the spherical surface 34 extends into a desired captured location within the retainer central channel 141, the shank surface 34 is in contact with the edge 147 as well as with the inner panels 117 at surfaces 129. The combination of the rim or edge 147 surface contact and the panel 117 surfaces 129 contact resiliently pressing against the radiused surface 34, provides a fairly tight friction fit between the head 8 and the retainer 12, the surface 34 being pivotable with respect to the retainer 12 with some force. Thus, a tight, non-floppy ball and socket joint is now created between the retainer 12 and the shank upper portion 8.

With reference to FIG. 35, the receiver is then pulled upwardly or the shank 4 and attached retainer 12 are then moved manually downwardly into a position wherein the retainer panels 118 are disengaged from the receiver surfaces 95, allowing the panels 118 to resiliently release and extend outwardly into a neutral or near-neutral position at a location below the receiver annular surface 96 that defines the ceiling of the receiver inner chamber 61. The panels 118 are now captured within the receiver and the retainer with any upward movement resulting in the panel top surfaces 134 abutting against the receiver surfaces 96 and/or 97. However, although fully capture, the retainer/shank combination is advantageously only partially restrained with respect to the receiver, as a user is able to rotate the retainer about the receiver axis B prior to locking of the shank with respect to the receiver. At this time also, the retainer surface 121 and bottom surface 122 that forms a lower skirt beneath the retainer body surfaces 120 and 124 are all seated within the stepped surfaces of the receiver. Specifically, the retainer lower surfaces 124 are seated on the receiver annular surface 102 and the bottom surface 122 is seated on the annular surface 103. Downward pressure of the shank head 8 on the retainer edge 147 further expands the retainer body 115 outwardly, with the outer surfaces 120 pressing against the receiver inner cylindrical surface 100 and the lower skirt surface 121 pressing against the receiver inner cylindrical surface 101. The retainer body formed in part by the lower skirt surface 121 advantageously allows for the head 8 to seat lower within the receiver than in other known polyaxial bone anchors. As will be described in greater detail below, the skirt feature that allows for a more stable lower seating surface in combination with the retainer cupped surface 149 that allows for increased angular orientation of the shank with respect to the retainer, and thus with respect to the entire bone screw assembly, allows for such an angular increase without the need to provide a cut-out or cupped surface at and near the receiver bottom 108. Also advantageous is the fact that the partially constrained retainer 12 may be rotated with respect to the receiver 10 about the axis B, allowing for the user to choose the location of the increased angle of orientation between the receiver 10 and the shank 4.

With further reference to FIG. 35, after the retainer 12 is moved downwardly into the receiver 10 and seated on the surfaces 102 and 103, the insert 14 remains located spaced above the shank head 8 as the receiver spring tabs 78 and/or the receiver stepped surface 94 prohibits downward movement of the insert 14 unless a downward force is applied on the insert either by a tool or the rod 21 and closure top 18 shown in FIG. 36, for example. In some embodiments, when the receiver 10 is pre-assembled with the shank 4, the entire assembly 1 may be implanted at this time by inserting the driving tool (not shown) into the receiver and the shank drive 46 and rotating and driving the shank 4 into a desired location of the vertebra 17. At this time, prior to locking with a closure top, the receiver 10 may be articulated to a desired angular position with respect to the shank 4 (such as the angular orientations shown in FIGS. 41 and 43, for example), that will be held, but not locked, by the frictional engagement between the retainer 12 inner panels 117 and the shank upper portion 8. In some cases it may be desirable to lock the insert 14 into the receiver 10 at this time, the insert 14 being pressed downwardly into locking engagement with the shank head 8 by a tool pressing downwardly on the insert, the tool entering through the receiver opening 66 and pressing downwardly on the insert saddle 153. Such a tool may also include (or alternatively be) a structure for gripping the receiver, for example, a pronged tool or tool portion extending into the receiver apertures 77. Or, as explained above, the insert 14 may remain spaced above the shank head 8 until locked into place by the rod 21 and the closure top 18 pressing down upon the insert 14. As explained above and as best shown in FIGS. 37 and 38, the diameter of the insert outer surface 159 is sized large enough to require that the surface 159 must be forced into the cylindrical surface 95 of the receiver by a tool or tools or by the closure top 18 forcing the rod 21 downwardly against the insert 14 with sufficient force to interferingly frictionally lock or wedge the insert 14 into the receiver 10 at the surface 159. This independent lock-and-release feature gives the surgeon flexibility to loosen the closure top and even remove the closure top and rod without affecting the locking of the polyaxial mechanism of the assembly 1, the anchor assembly functioning like a fixed monoaxial screw with the shank 4 in fixed relation with the receiver 10, but with the shank remaining in a desired angle with respect to the receiver. For example, with reference to FIGS. 39 and 40, once the insert 214 is locked against the receiver as shown in FIG. 38, if a rod and closure top have been assembled with the receiver 10, the closure top 18 may be loosened or removed and/or the rod 21 may be adjusted and/or removed and the frictional engagement between the insert 14 and the receiver 10 at the receiver surface 95 will remain locked in place, advantageously maintaining a locked angular position of the shank 4 with respect to the receiver 10. At such time, another rod, such as a deformable rod 21' and cooperating alternative closure top 18' may be loaded onto the already locked-up assembly to result in an alternative assembly. The illustrated rod 21' has the same dimensions as the rod 21, with a cylindrical surface 22', but is made from a material, such as PEEK, that deforms in response to pressure from the closure top, thus making the closure top 18' having the domed surface 190' and central nub 189' a more desirable locking mechanism for keeping the deformable rod 18' in place within the receiver 10. Because the locking of the polyaxial mechanism of the assembly is not dependent on the force of the rod 21' and closure top 18' on the insert 14, any further deformation or eventual loosening of the rod with respect to the closure top 18' or the insert 14 does not affect the secure locking between the insert 14 and the receiver 10 and thus the shank 4 stays frictionally locked against both the insert 14 and the retainer 12, locking the shank 4 in a desired angular position with respect to the receiver 10.

If unlocking of the insert 14 with respect to the receiver 10 is desired, a tool (not shown) may be inserted into the through apertures 77 of the receiver 10 and the through apertures 167 of the insert 14 and the insert 14 may be pulled away from the receiver 10. Such a tool may include a piston-like portion for pushing directly on the shank while the insert 14 is pulled away from the receiver. At such time, the shank 4 may be articulated with respect to the receiver 10, and the desired friction fit returns between the retainer 12 and the shank surface 34, so that an adjustable, but non-floppy relationship still exists between the shank 4 and the receiver 10. If further disassembly if the assembly is desired, such is accomplished in reverse order to the procedure described previously herein for the assembly 1.

Returning to FIGS. 36-38, the rod 21 is positioned in an open or percutaneous manner in cooperation with the at least two bone screw assemblies 1. The closure structure 18 is then advanced between the arms 62 of each of the receivers 10. The closure structure 18 is rotated, using a tool engaged with the inner drive 186 until a selected pressure is reached at which point the rod 21 engages the U-shaped saddle 173 of the compression insert 14, further pressing the insert spherical surface 178 and stepped shank gripping surfaces 180 against the shank spherical surface 34, the edges of the stepped surfaces 180 penetrating into the spherical surface 34, pressing the shank upper portion 8 into locked frictional engagement with the retainer 12. Specifically, as the closure structure 18 rotates and moves downwardly into the respective receiver 10, the point 189 and rim 190 engage and penetrate the rod surface 22, the closure structure 18 pressing downwardly against and biasing the rod 21 into compressive engagement with the insert 14 that urges the shank upper portion 8 toward the retainer 12 and into locking engagement therewith at the retainer edge surface 147, the retainer 12 frictionally abutting the receiver surfaces 102 and 103 and pressing outwardly against the receiver cylindrical surfaces 100 and 101. For example, about 80 to about 120 inch pounds of torque on the closure top may be applied for fixing the bone screw shank 6 with respect to the receiver 10. At this time, the retainer inner edge 147 engages and digs into the shank head 8. At this time, the inner panels 117 may be slightly spaced from the shank head 8 or may be still touching the shank spherical surface 34, but are no longer in tight or close frictional engagement with the surface 34 and thus are not participating in the final locking engagement between the shank 4 and the retainer 12. As best shown in FIG. 38, due to the position and geometry of the lower skirt surfaces 121 and 122 with respect to the receiver 10 and also due to the location of the inner edge 147, the shank head 8 sits low in the receiver cavity 61, allowing for desirable increased articulation of the shank 4 with respect to the retainer 12 and thus with respect to the receiver 10 as compared to a retainer that does not include such a lower skirt, for example. If disassembly if the assembly 1 is desired, such is accomplished in reverse order to the procedure described previously herein for assembly.

Figure 41:
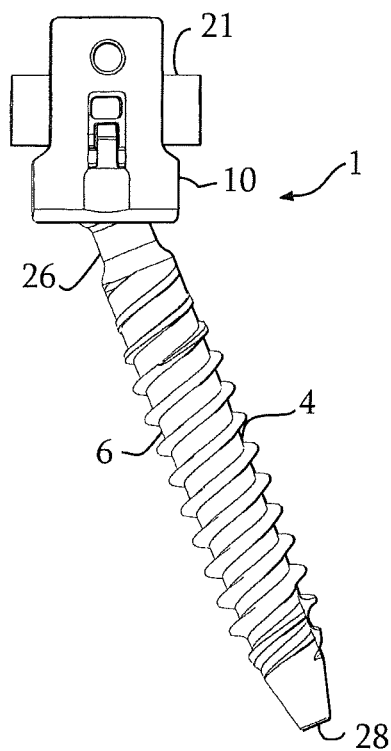
FIG. 41 is a reduced side elevational view of the assembly of FIG. 1, shown fully assembled with the shank disposed at a twenty-two degree (cephalad) angle with respect to the receiver.
Figure 42:
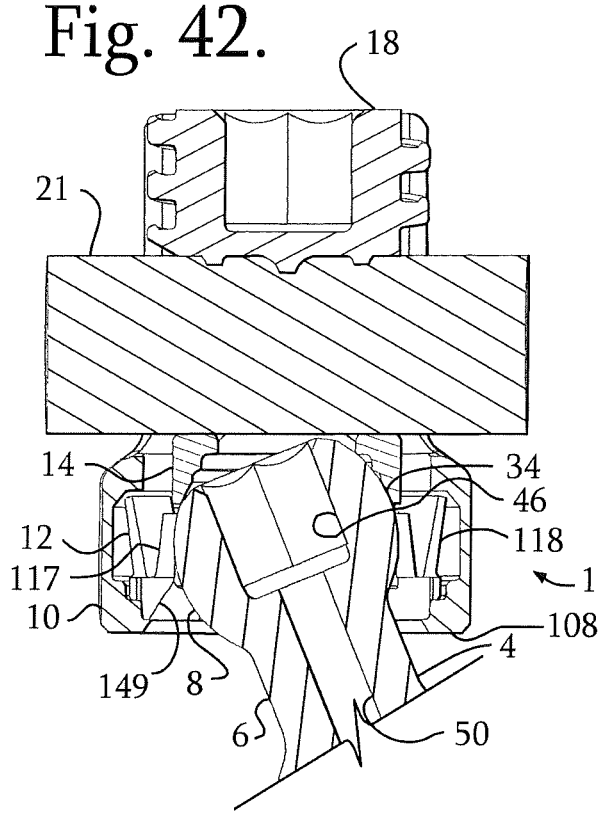
FIG. 42 is an enlarged and partial side elevational view of the assembly of FIG. 41 with portions broken away to show the detail thereof.
Figure 43:
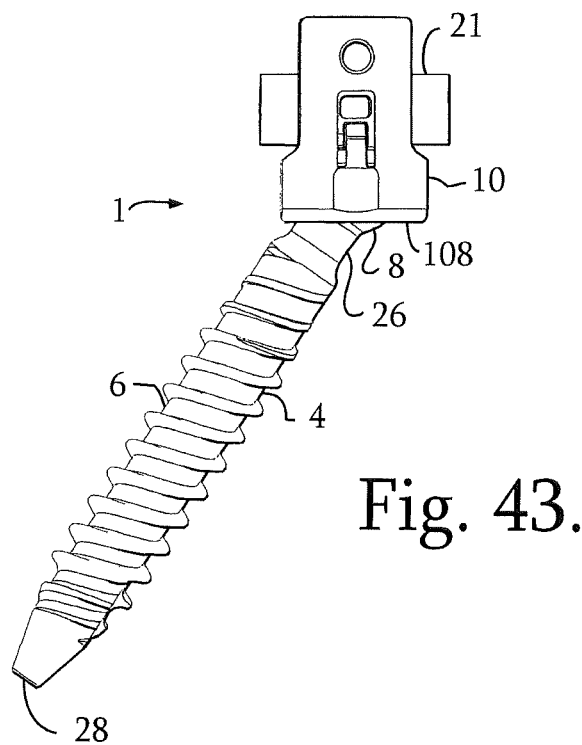
FIG. 43 is a reduced side elevational view of the assembly of FIG. 1, shown fully assembled with the shank disposed at a thirty-three degree (caudad) angle with respect to the receiver.
Figure 44:
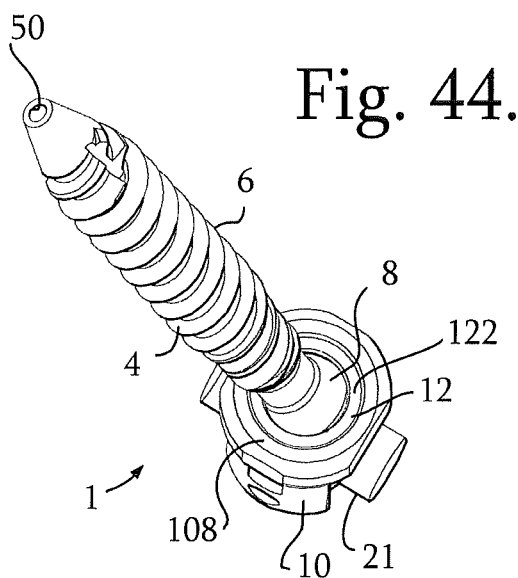
FIG. 44 is a perspective view of the assembly of FIG. 43.
Figure 45:
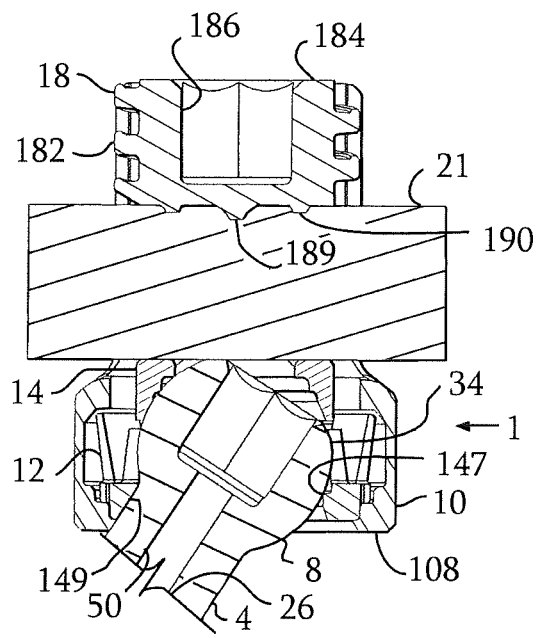
FIG. 45 is an enlarged and partial side elevational view of the assembly of FIG. 43 with portions broken away to show the detail thereof.

With reference to FIGS. 41-46, different angular or articulated positions of the shank 4 with respect to the receiver 10 are shown, some making full use of the slit 148 and adjacent cut-out or cupped surfaces 149 of the retainer 12. For example, compare FIGS. 43-45 wherein the shank 8 is pivoted toward and into engagement with the cupped surfaces 149 as compared to the arrangement shown in FIGS. 41 and 42, wherein the shank 4 is pivoted in a direction opposite to the retainer slit 148. In FIGS. 41 and 42 wherein the shank is pivoted in a direction away from the slit 148 and cupped surfaces 149, a resulting shank to receiver articulation is about twenty-two degrees (cephalad, for example), which is a desirable degree of articulation in some instances. FIGS. 43-46 show a thirty-three (caudad) or slightly further articulation, possible when the shank head 8 abuts against both surfaces 149 as well as moving slightly into the gap formed by the slit 148.

Figure 46:
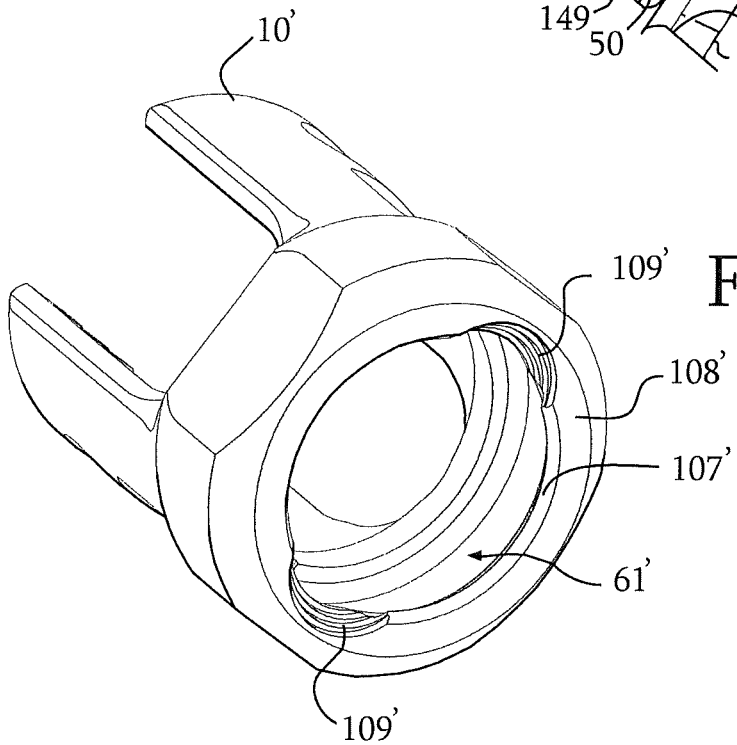
FIG. 46 is an enlarged perspective view of an alternative favored angle receiver according to the invention having opposed lower concave stepped surfaces for cooperating with the retainer of FIG. 1 to allow for up to a forty degree angle of the shank of FIG. 1 with respect to the alternative receiver.
Figure 51:
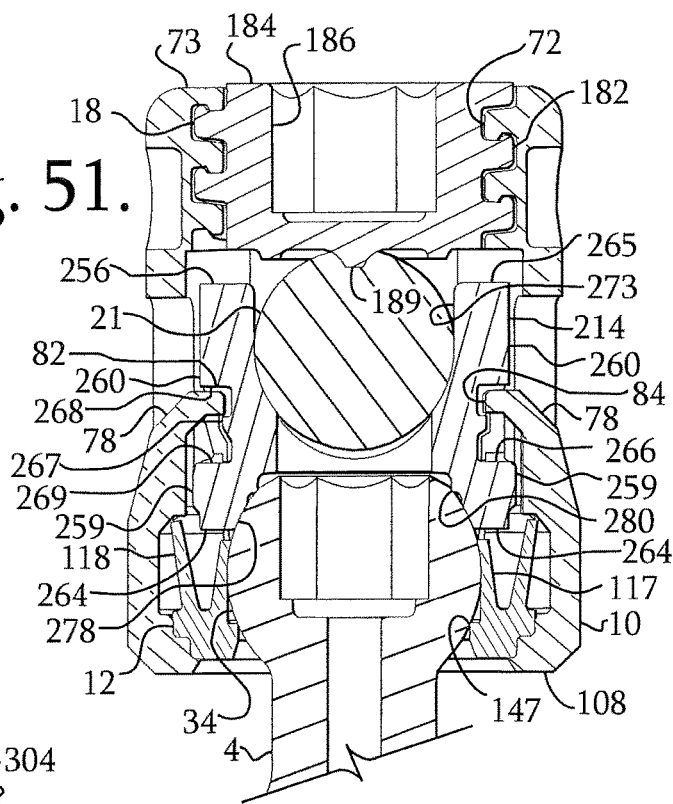
FIG. 51 is an enlarged and partial front elevational view of the receiver, retainer, rod and closure top of FIG. 1 shown fully assembled with the alternative insert of FIG. 47, also in front elevation, with portions broken away to show the detail thereof.

FIG. 46 illustrates an alternative receiver 10' that includes a bottom surface 108' further defined by a pair of opposed, stepped and concave curved bottom surfaces 109'. Otherwise, the receiver 10' is identical to the receiver 10 described above and thus fully cooperates with the retainer 12, insert 14, shank 4, rod 21 and closure top 18 in a manner substantially identical to what has been described above with respect to the assembly 1. Just like the receiver 10, when the retainer 12 is fully assembled with the receiver 10', the retainer 12 is captured within the receiver inner cavity 61', but is only partially constrained therein, the retainer being rotatable about the central axis of the receiver 10'. Thus, the retainer 12 slit 148 and surfaces 149 can be aligned with either of the receiver stepped surfaces 109'. When the retainer surfaces 149 are aligned one of the surfaces 109', at least a forty degree angle of articulation between the shank 4 and the receiver 10' is possible.

With reference to FIGS. 47-51, an alternative non locking compression insert 214 is illustrated for use with the shank 4, receiver 10, retainer 12, closure top 18 and rod 21 previously described herein. The insert 214 is substantially similar to the insert 14 previously described herein, having all the features of the insert 14 with the exception of the through apertures 167 and the enlarged interference fit surface 159. Instead, the insert includes a pair of opposed alternative apertures 166 formed into arm surfaces that do not extend all the way through the insert arms and a cylindrical surface 259 that is similar to the surface 159 of the insert 14, except that a diameter of the surface 259 is sized to easily slidingly fit within the receiver surface 95 rather than interferingly fit with such surface. Thus, the insert 214 includes an insert body 256, a pair of upstanding arms 257, a cylindrical body surface 258, arm outer surfaces 260, a lower cylindrical surface 261 a sloping ledge 262, a planar bottom 264, arm tops 267, grooves 270, a central through bore 271, a saddle surface 273, a saddle seat 274, an inner cylindrical surface 276, a lower radiused surface 278 and a shank gripping portion 280, as well as other features that are the same as, or substantially similar to, the respective insert body 156, pair of upstanding arms 157, cylindrical body surface 158, arm outer surfaces 160, lower cylindrical surface 161 sloping ledge 162, planar bottom 164, arm tops 167, grooves 170, central through bore 171, saddle surface 173, saddle seat 174, inner cylindrical surface 176, lower radiused surface 178 and shank gripping portion 180 of the insert 14 previously described herein.

Each insert aperture 266 is a depression formed in the surface 260 having a substantially rectangular profile similar to the aperture 168 of the insert 14. Also, each aperture 266 opens toward and communicates with the respective adjacent groove 270 for assembly with the receiver holding tab 78 in a manner similar to the cooperation previously described herein between the aperture 168 and the groove 170 of the insert 14. However, unlike the smooth substantially planar surface defining each aperture 168, each aperture 266 further includes a horizontal bar or bridge portion 267 substantially parallel to the top surface 265 that separates the aperture 266 into two portions; an upper portion 268 and a lower portion 269, each having a substantially planar surface for sliding cooperation with a holding tab surface 84. During assembly with the receiver, the insert 214 is rotated and the receiver holding tab surfaces 84 slide along the grooves 270 until they spring into the apertures 266 at the lower portions 269 thereof, each bar 267 abutting against each tab 78 at the top surface 82, prohibiting the insert 214 from moving further downwardly into the receiver cavity 61. Thus, unlike the insert 14 that cannot move further into the cavity because of the interference fit surface 159, the insert bars 267 capture the tabs 78 in the lower portion 269 of each aperture 266 during assembly, and shipping, if desired, keeping the insert 214 in a desirable position until the insert 214 is pressed, with some force, either by a tool or by the rod 21 and closure top 18 in a downward direction, the tabs 78 resiliently sliding along lower sloping surfaces of the bars 267 until the tabs 78 slide past the bars 267 and the tab surfaces 84 spring into the upper aperture portions 268, as shown, for example, in FIG. 51.

The insert is otherwise assembled with the receiver 10, retainer 12, shank 4, rod 21 and closure top 18 in a manner the same as previously described above with respect to the assembly 1, with the exception that the insert 214 need not be forced downwardly into a locking interference fit with the receiver 10 when the shank 4 is locked in place. If the closure top 18 is loosened or if the closure top 18 and the rod 21 are removed from the assembly 1, the insert 214 will also shift upwardly in the receiver 10 and the shank 4 will not remain locked with respect to the retainer 12 and the receiver 10.

With reference to FIGS. 52-74, polyaxial bone screw assemblies 1 (as well as alternative bone screw assemblies 1001 and 2001 described below) according to the invention may be used with longitudinal connecting member assemblies that are sometimes called "soft" or "dynamic" connectors that may include one or more sleeves with cooperating, spacers, bumpers, an inner tensioned cord, and may include one or two end blockers or fixers for fixing the cord to the connector assembly. A variety of such connector components are described in Applicant's U.S. patent application Ser. No. 12/802,849 filed Jun. 15, 2010 (U.S. Publication No. 2010/0331887) and incorporated by reference herein. With reference to FIG. 57, the bone screw 1 is illustrated assembled with a hard, inelastic, flanged sleeve 304, through which a tensioned cord 306 extends, sleeve and cord may be a part of such a longitudinal connector assembly or system as described in U.S. patent application Ser. No. 12/802,849. The sleeve 304 is also illustrated in greater detail in FIGS. 52-56, for example. Another alternative sleeve 305 is shown assembled with the bone screw assembly 1 in FIG. 64. The sleeve 305 is shown in greater detail in FIGS. 66-70. The cord 306, is shown, for example, in FIGS. 57-59 and 61-63.

With particular reference to the sleeve 304 shown in FIGS. 52-63, there is further illustrated at FIGS. 62 and 63 a cooperating end cord blocker or fixer 310 with a cord fixing set screw 312, an elastic end bumper 314 and a substantially cylindrical spacer 316 that may be elastic or inelastic. The cylindrical, tubular spacer 316 includes an outer annular groove near an end thereof, aiding in elastic compression. However, in other embodiments, the spacers may not have grooves. Spacers may be cut to a desired length on the end opposite the groove. The cord blocker 310, the bumper 314 and spacer 316 are each located about the cord 306, typically with spacers 316 being disposed between each pair of bone anchors 1 of an overall assembly (not shown) that includes at least two bone anchors 1, but may include any number of bone anchors with the cord 306 at least fixed at either end, either at a terminal or end bone anchor 1 or at an end blocker 310 or other fixing member that may be, for example, a cord to hard rod coupler. The tubular bumper 314 and tubular spacers 316 shown in the figures are transparent, allowing for viewing of the sleeve 304 and the tensioned cord 306. However, it is foreseen that in other embodiments, the bumper and spacers may be made of materials that may not be transparent or translucent. Also as shown in FIGS. 60 and 61, two types of bone screw closures are utilized, either a slide or slipping closure top 18 previously described herein with respect to the assembly 1 or a cord gripping closure top 18". The closure top 18" is also illustrated in FIGS. 65 and 66 and only differs from the top 18 in that the top 18" does not include a bottom rim or bottom point, but rather a cord fixing or penetrating extension 317 having a bottom surface 318 for gripping the cord 306. With reference to FIG. 58, the slide or slip closure top 18 engages a respective sleeve 304 but not the cord 306, allowing the cord to slip or slide within the polyaxial screw 1. With reference to FIG. 61, the grip closure top 18" extends through the sleeve 304 at the bore 360 and the surface 318 grips and fixes the cord 306 against an inner surface defining the bore 336 of the sleeve 304 and thus fixes the cord 306 in relation to the polyaxial screw 1 that is mated with the closure top 18".

Although not shown, the sleeve 304 and cord blocker 310 may include tubular extensions at either side thereof that may be sized and shaped to extend into the inner lumen or bore of the spacers 316 or the bumper 314. Such spacer overlap with respect to the sleeves is sometimes desired to provide additional anti-shear support for a connecting member. The bumper 314 also extends about the cord 306 and is typically made from an elastomer while the outer spacers 316, although typically elastomeric, may be made from a material with a different durometer, typically (but not always) being tougher and less compressible than the material of the bumper 314. The sleeves 304 and in some embodiments the spacers 316 are typically made from a hard, non-elastic material, such as a metal or metal alloy, like cobalt chromium. Flanged portions of the sleeves 304 are located on either side of the bone screw receivers 10, the flanges abutting directly against the spacers 316 or the bumper 314, the flanges extending radially outwardly to an extent to fully engage ends of adjacent spacers or the bumper, resulting in a stable, secure, substantially full contact between the individual elements of a connector assembly. Furthermore, the flanges allow for assembly and dynamic setting of a longitudinal connector prior to implantation of the connector, if desired, with the cord 306 being placed in tension and at least the bumper 314 being placed in compression. In some embodiments of the invention, tensioning of the cord 316 and compression of the bumper 314 and optionally the spacers 316 may be performed after the longitudinal connector assembly sleeves 304 (or 305) are attached to the bone screws 1.

With particular reference to FIG. 57, the bone screw assembly 1 is illustrated assembled with the sleeve 304. With particular reference to FIGS. 52-56, the sleeve 304 further includes a body portion 334 generally sized and shaped for being received within the polyaxial bone screw 1 receiver 10 and about a cord 306. A through bore 336 extends centrally through the body portion 334, the bore 336 being sized and shaped to slidingly receive the cord 306. At either side of the body portion 334 are a pair of opposed spaced radially extending flanges 338. The body portion 334 includes an annular planar top surface 340, a substantially cylindrical bottom surface 341, opposed planar surfaces 342 adjacent the bottom surface 341 and opposed partially cylindrical or otherwise protruding portions 344 located above each surface 342. The top annular surface 340 partially defines each of the protruding portions 344. The body 334 is sized and shaped to closely fit within inner arm surfaces of the bone screw receiver 10. The portions 344 function to center the sleeve 304 within the bone screw receiver 10 and also advantageously strengthen the sleeve, resulting in better load transfer. It is foreseen that in some embodiments, the flanges 338 may be reduced or eliminated as the centering of the sleeve with respect to the bone screw receiver 10 may be performed by the portion or portions 344.

In the illustrated embodiment, each flange 338 has a substantially cylindrical outer surface 346 adjacent and perpendicular to an outer planar annular surface 348 that is sized and shaped for directly abutting against a bumper or a spacer. The bore 336 extends through each of the planar surfaces 348. The cylindrical surface 346 is truncated at a lower end thereof forming the bottom surface 350 that is also adjacent and substantially perpendicular to the surface 348. Variously curved transition surfaces 351 curve towards a more uniform flange 352 that is located adjacent to the body lower cylindrical surface 341, the surfaces 351 being sized and shaped to clear the receiver inset surfaces 63 located near the receiver U-shaped seat 68 when the sleeve is inserted into the receiver U-shaped channel 64 and seated on the seat 174 of the insert 14. The body lower cylindrical surface 341 is sized and shaped to be closely received by the insert saddle 173 near the receiver seat 68. Adjacent to the transition surfaces 351 and the cylindrical surfaces 346, each flange includes inner opposed facing surfaces 353. Between the surfaces 353 and the sleeve body 334 there are concave cupped surfaces 355 that are sized and shaped to receive and partially wrap about portions of the receiver arm surfaces 71 that transition between inner and outer facing surfaces of the arms. The surfaces 353 also receive and curve about portions of the receiver outer surfaces 76 located adjacent the transition arm surfaces 71, see FIGS. 57 and 62, for example. Near the top body surface 340 and also adjacent to the outer cylindrical surface 346 of the flange, the flanges also include inner cylindrical surfaces 356, sized and shaped to provide clearance for receiving the closure top 18 or 18". It is noted that the body portion 334 as well as the inner surfaces of the flanges 338 may be sized and shaped to be receivable by and frictionally fixed to a variety of monoaxial or polyaxial screw heads or receivers, including, but not limited to, the receiver 10.

Figure 52:
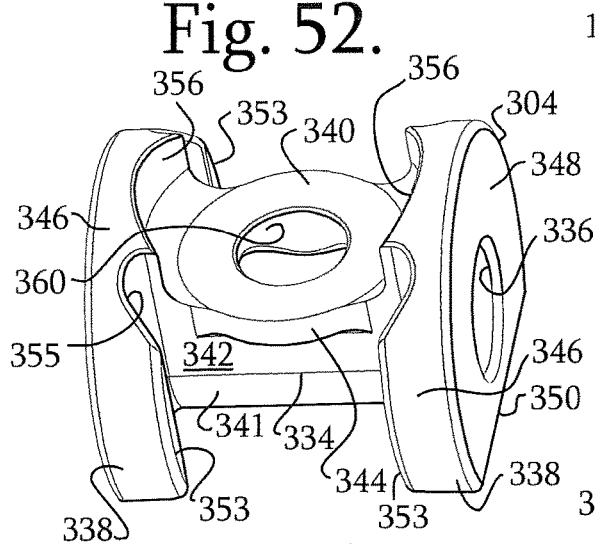
FIG. 52 is a perspective view of a sleeve according to the invention for use with bone screw assemblies of the invention.
Figure 53:
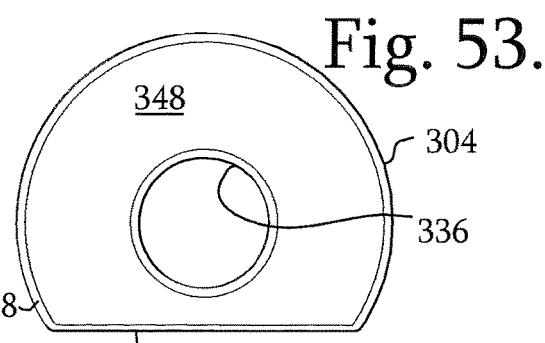
FIG. 53 is a front elevational view of the sleeve of FIG. 52.
Figure 54:
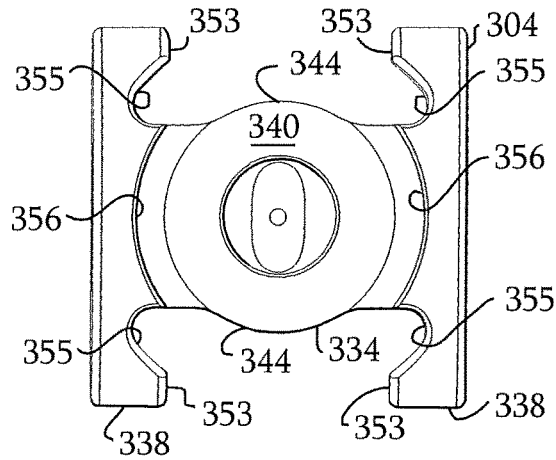
FIG. 54 is a top plan view of the sleeve of FIG. 52.
Figure 55:
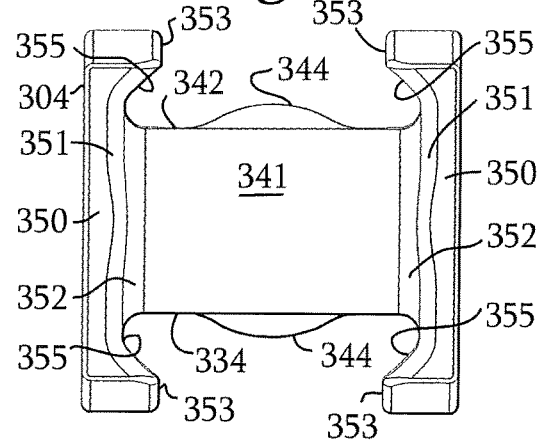
FIG. 55 is a bottom plan view of the sleeve of FIG. 52.

With reference to FIGS. 52, 54 and 56, a bore 360 is formed in the body 334 at the top surface 340 and located centrally between the flanges 338. The bore 360 is transverse to and communicates with the through bore 336. The bore 360 is sized and shaped to receive the cord penetrating extension 317 of the closure top 18" therein as best shown in FIG. 61. The sleeve 304 is shown with the closure top 18 in FIGS. 57-59. The top 18 does not extend down into the through bore 360, allowing for the cord 306 to slide freely there within.

The sleeve 304, as well as the cord blocker 310 with set screw 312 may be made from a variety of inelastic materials, including, but not limited to metals, metal alloys, including cobalt chromium, and inelastic plastics including, but not limited to plastic polymers such as polyetheretherketone (PEEK), ultra-high-molecular weight-polyethylene (UHMWP), polyurethanes and composites, including composites containing carbon fiber and layers of different materials.

With reference to FIG. 57 that shows the sleeve 304 assembled with the bone screw 1 and having a pair of cylindrical and tubular spacers 316 on either side thereof, the sleeve and spacers surrounding a cord 306, and also with respect to FIG. 62, that shows the sleeve 304 cooperating with both a spacer 316 and a blocker 310 and bumper 312, as well as a cord 306, a connecting member assembly utilizing the sleeve 304, cord 306, cord blocker 310, bumper 314 and one or more cylindrical spacers 316 may be assembled as follows:

First, after two or more bone screws 1 are implanted, the distance between the screws is measured. Thereafter, the spacers 316 are cut to a desired length based upon the measurement made between the bone screws. Because the sleeves 304 are made from a hard material, typically a metal or metal alloy, if it is desired to use sleeves with tubular extensions, it is not practical to cut the tubular portions to a desired length during the surgical procedure. Therefore, a variety of sleeves 304 are typically provided to end users having at least three different tube portion lengths. Thereafter, the sleeves 304, spacers 316, bumper 314 and a cord blocker 310, (or two cord blockers on either end, with or without an adjacent bumper) are fed onto a cord 306 in a desired order to result in a desired assembly in a manner described in greater detail in the patent application Ser. No. 12/802,849 incorporated by reference herein. It is noted that the cord 306 is typically much longer than shown in the drawing figures and then cut to length near an end thereof after being fully assembled with the remaining elements of the connector assembly, tensioned and fixed to the blocker 310. In some embodiments of the invention, single blockers, bumper/blocker combinations or rod/cord couplers (or various different combinations thereof) may be placed on either end of the assembly and the cord pre-tensioned before the assembly is implanted in and between the already implanted bone screws 1. In other embodiments, a loosely assembled connector may be placed in contact with and between the implanted bone screws 1, with the set screw 312 engaged with the cord 306 enough to prevent the elements from slipping off one end of the cord 306. However, in such an assembly, the cord 306 would not yet be tensioned and thus the individual elements would be spread apart along the cord and the cord would have to be of a length so that the cord could be grasped and tensioned after the assembly is fixed to the bone screws 1.

A connector member assembly is then implanted by inserting each sleeve 304 into to one of the bone screws 1. The sleeve 304 is top loaded through the receiver opening 66 with the inner curved surfaces 355 aligned with and sliding along the arm edge surfaces 71 until the sleeve 304 is seated on the insert 14 with the sleeve protrusions 344 engaging the insert arm top surfaces 165. Closure tops 18 or 18" are then inserted into and advanced between the arms of the bone screw receiver 10 so as to bias or push against the respective sleeves 304. A driving tool (not shown) is inserted into each closure drive to rotate and drive the respective closure top 18 or 18" into the respective receiver 10, the lower surface of the closure top engaging and pressing downwardly upon the top body surface 340 of the sleeve 304. As shown in FIG. 58, when the closure top 18 is used, the bottom rim 190 digs into the top body surface 340 but the closure does not engage the cord 306 located within the sleeve bore 336. As shown in FIGS. 58 and 61, downward movement of the closure top 18 or 18" onto the sleeve 304 in turn presses the sleeve 304 into engagement with the insert 14 that in turn presses downwardly on the shank head 8, locking the head 8 between the insert 14 and the retainer 12, the retainer 12 pressing outwardly against the receiver 10. Because the insert 14 is a lock and release insert, the insert 14 is now wedged against the receiver at the surface 95 and the polyaxial mechanism of the bone screw assembly 1 is now locked, even if the closure top 18 or 18" is loosened and rotated away from the sleeve surface 340.

A tensioning tool (not shown) known in the art may then be used to pull upon and put tension on the cord 306. It is noted that if more than one gripping closure tops 18" are used at either end of a connector, one top would be locked initially and then the other or others would be locked after tensioning, or alternatively perform more than one tensioning step. Preferably a bumper 314 and end blocker 310 are used at at least one end and the cord 306 is preferably tensioned until the bumper 314 compresses and then the set screw 312 is rotated and driven into the blocker 310 and up against the cord 306 using a driving tool (not shown) engaged with an inner drive of the screw 312. The blocker 310 advantageously includes opposed grooves 311 (or planar sides in some embodiments) allowing for the placement of a counter-torque tool for holding the blocker during tensioning and fixing of the cord 306 within the blocker. As explained in U.S. patent application Ser. No. 12/802,849, the set screw 312 and blocker 310 combination preferably includes a limited travel feature such that the set screw is locked into place at a location that firmly holds but does not damage the cord 306. The cord 306 is ultimately trimmed to a desired length close to each end of the connector.

The connector assembly is thus substantially dynamically loaded and oriented relative to the cooperating vertebra, providing relief (e.g., shock absorption) and protected movement with respect to flexion, extension, distraction and compressive forces placed on the assembly and the connected bone screws 1. In some embodiments of a connecting member according to the invention, a sleeve and rod combination may be used at one end (or both ends) of the assembly to provide a hard, non-elastic elongate portion for attachment to an additional bone screw or screws, if needed, to provide a connecting member with both dynamic, elastic segments as well as a longer rigid inelastic segment.

Eventually, if the spine requires more rigid support, such a connecting member assembly may be removed and replaced with another longitudinal connecting member, such as a solid rod or bar, having the same width or diameter as body portions of the sleeves 304, utilizing the same receivers 10 and the same or similar closure structures 18. Alternatively, if less support is eventually required, a less rigid, more flexible assembly, for example, an assembly having spacers 316 and a bumper or bumpers 314 made of a softer more compressible material than the spacer and bumper being replaced thereby, also utilizing the same bone screws 1 and the closures 18" as well as the closure 18.

With reference to FIGS. 63-74, the alternative sleeve 305 is illustrated with the bone screw assembly 1, both the slip 18 and grip 18" closure tops, and also with alternative spacers 316'. The sleeve 305 is substantially similar to the sleeve 304 with the exception that instead of having flanges with a partially circular profile defined by the partially cylindrical surfaces 346 and the planar surfaces 348, the sleeve 305 has opposed flanges 438 that are substantially rectangular in profile. Specifically, the sleeve flanges 438 have top planar surfaces 446, opposed planar front and back surfaces 447 and outer planar end surfaces 448 for abutting against the spacers 316 or 316' and the bumper 314. Otherwise, the sleeve 305 includes a body 434, a through bore 436, a body top 440, a body cylindrical bottom surface 441, body lower planar surfaces 442, protruding portions 444, flange bottom surfaces 450, curved transition surfaces 451, a transition flanged surface 452, inner opposed facing surfaces 453, concave or cupped surfaces 455 upper inner cylindrical surfaces 456 and a transverse bore 460 that are the same or similar in form and function to the respective body 334, through bore 336, body top 340, body cylindrical bottom surface 341, body lower planar surfaces 342, protruding portions 344, flange bottom surfaces 350, curved transition surfaces 351, transition flanged surface 352, inner opposed facing surfaces 353, concave or cupped surfaces 355 upper inner cylindrical surfaces 356 and the transverse bore 360 of the insert 304 as previously described herein. The substantially rectangular flanges 438 provide for a low profile sleeve having the top surface 446 conveniently located for cooperation with certain spacers to provide torsion control, such as the spacer 316' shown in FIGS. 71-74. The spacer 316' is elliptical or oval in profile, having a curved outer surface 490 having compression grooves 491 formed therein, a central bore 492, opposed planar end surfaces 494 and an upper overhanging portion or lip, generally 496 located at a narrowing of the ellipse, the lip 496 further having a planar end surface 497 and a planar bottom surface or ledge 498. As shown in FIGS. 71 and 72, the ledge surface 498 is sized and shaped to engage the top surface 446 of the sleeve flange 438 with the lip end surface 497 adjacent to the receiver 10 arm surfaces, providing some torsion control to the overall assembly. The narrow profile of the spacer 316' improves the low profile nature of the resulting assembly and also provides improved stability in flexion and extension. It is noted that during a surgical procedure, the spacers 316' must be cut to a desired length by the surgical staff, at a side opposite the compression grooves 491, similar to what is discussed above with respect to the spacers 316. To do this, a special jig (not shown) is used to cut the spacer in such a way as to include an overhanging lip 469 on the freshly cut side thereof.

Figure 75:
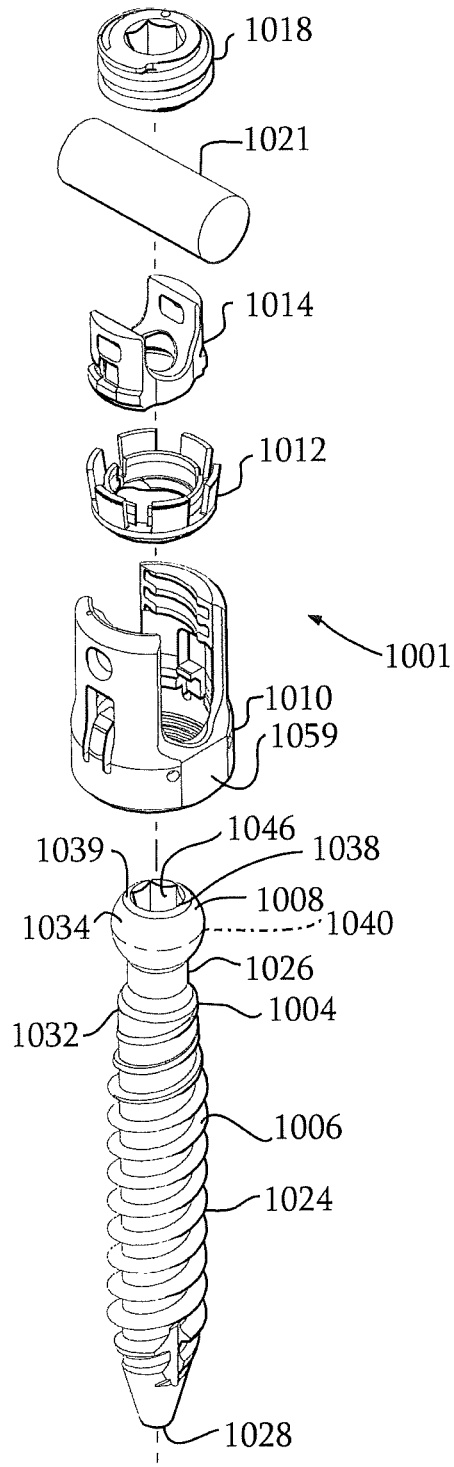
FIG. 75 is an exploded perspective view of an alternative polyaxial bone screw assembly according to the present invention including a shank, a receiver, an open friction fit retainer and a top drop and turn in place lower compression insert, further shown with a portion of a longitudinal connecting member in the form of a rod and a closure top.
Figure 76:
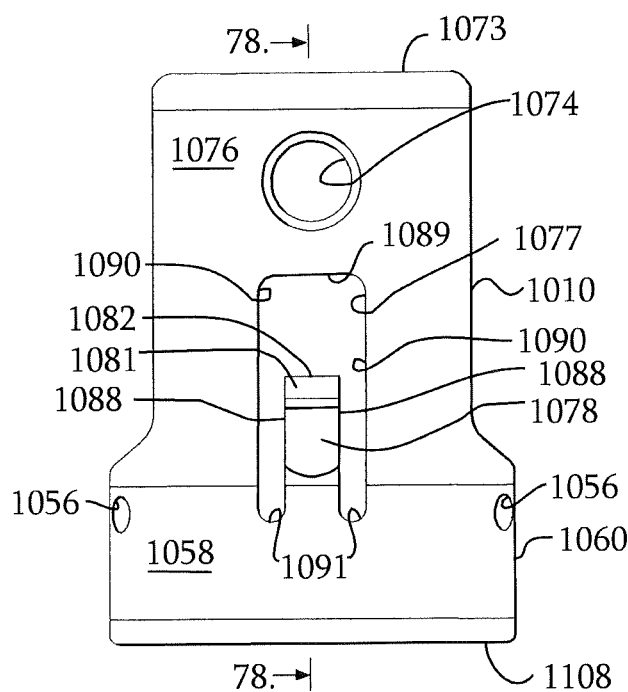
FIG. 76 is an enlarged side elevational view of the receiver of FIG. 75.
Figure 77:
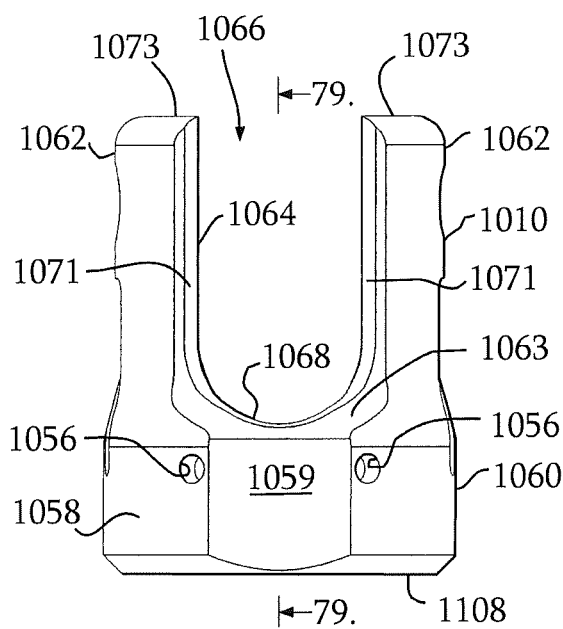
FIG. 77 is a reduced front elevational view of the receiver of FIG. 76.
Figure 78:
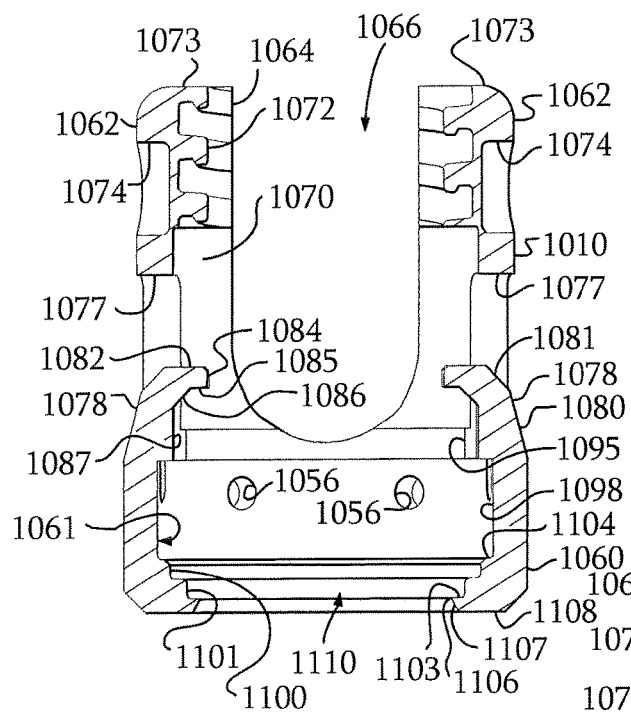
FIG. 78 is a cross-sectional view taken along the line 78-78 of FIG. 76.
Figure 79:
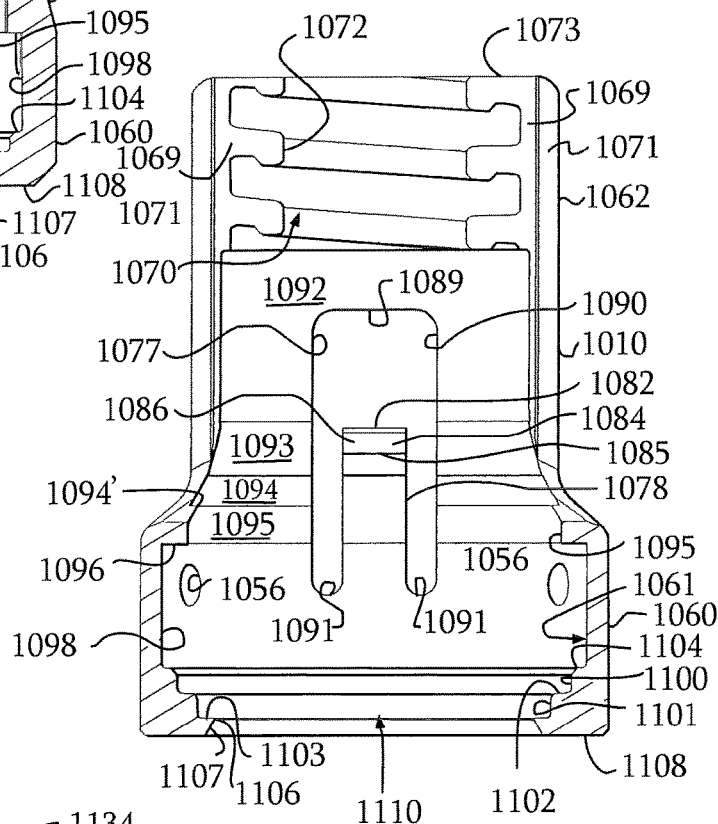
FIG. 79 is an enlarged cross-sectional view taken along the line 79-79 of FIG. 77.
Figure 80:
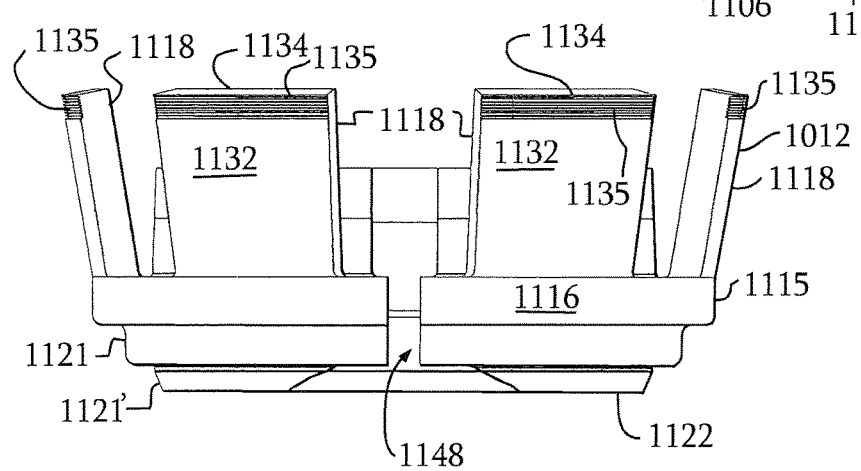
FIG. 80 is an enlarged front elevational view of the retainer of FIG. 75.
Figure 84:
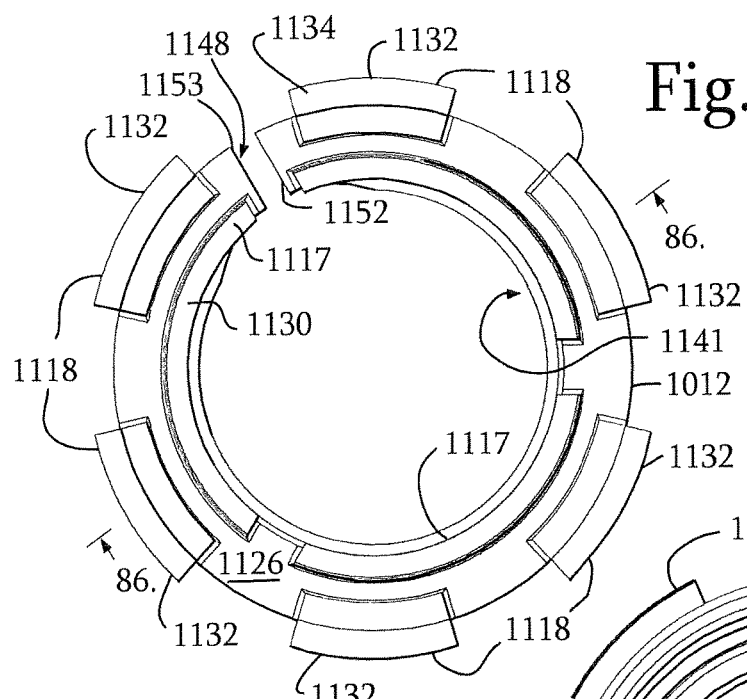
FIG. 84 is a top plan view of the retainer of FIG. 80.
Figure 85:
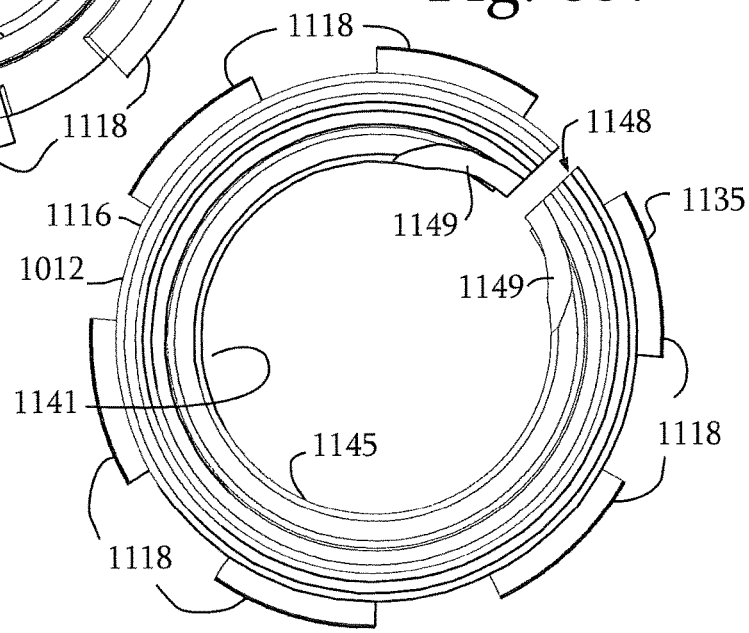
FIG. 85 is a bottom plan view of the retainer of FIG. 80.
Figure 86:
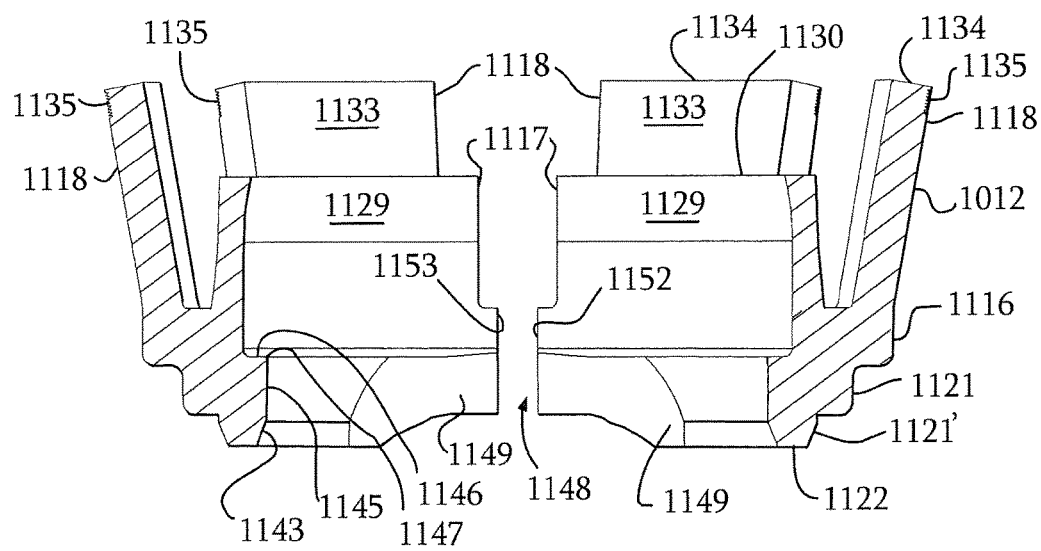
FIG. 86 is an enlarged cross-sectional view taken along the line 86-86 of FIG. 84.
Figure 87:
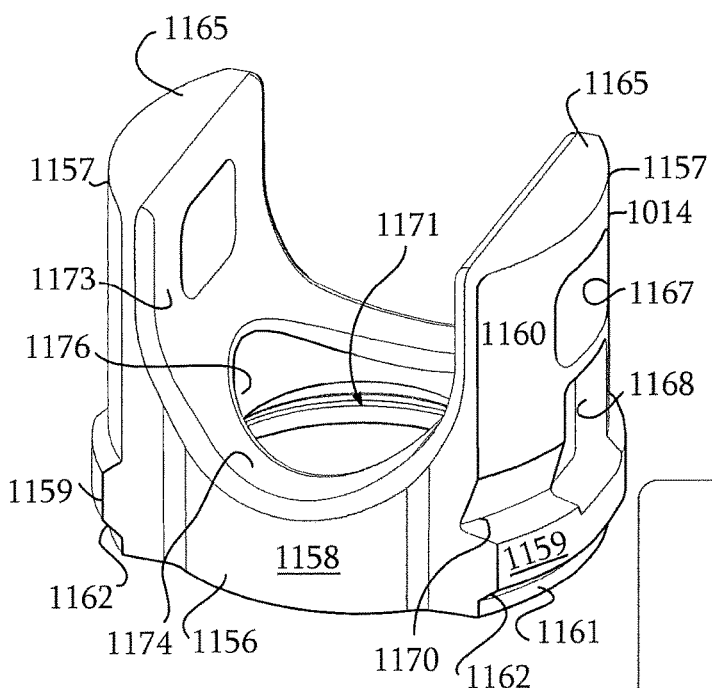
FIG. 87 is an enlarged perspective view of the insert of FIG. 75.
Figure 88:
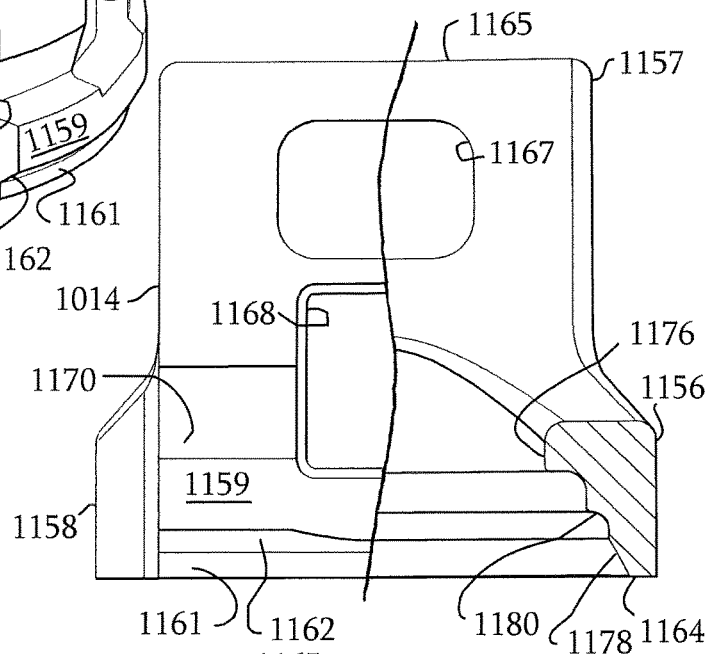
FIG. 88 is a side elevational view of the insert of FIG. 87 with portions broken away to show the detail thereof.
Figure 89:
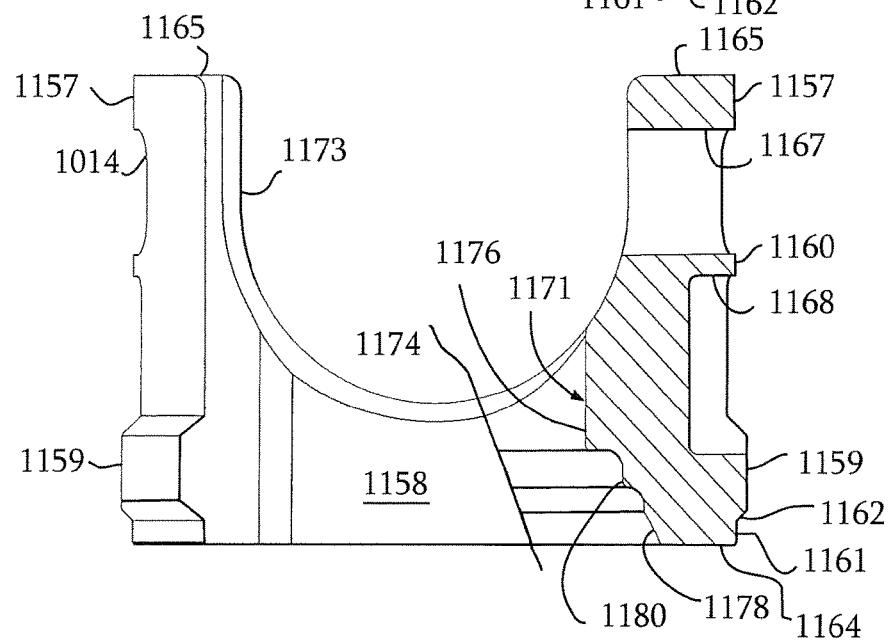
FIG. 89 is a front elevational view of the insert of FIG. 87 with portions broken away to show the detail thereof.

With reference to FIGS. 75-106, the reference number 1001 generally represents an alternative polyaxial bone screw apparatus or assembly according to the present invention. The assembly 1001 includes a shank 1004; a receiver 1010; a friction fit retainer 1012, and a crown-like compression or pressure insert 1014. There are many similarities between the assembly 1001 and the assembly 1. Differences between the embodiments 1 and 1001 mainly concern the retainer 1012 that is made by a turning process, allowing for more radiused surfaces that provide improved friction fit between inner tangs and the shank head 1008, for example. Ridges or other high friction coefficient treatments on the outside tangs provide improved gripping with the receiver during certain stages of assembly. Furthermore, as will be described in greater detail below, the retainer 1012 includes another lower outer tier or skirt cooperating with the receiver that allows for an even lower profile, dropping the retainer (and thus the cooperating shank head) even lower in the receiver than what is shown in FIG. 1 for the assembly 1. As with the assembly 1, the receiver 1010, retainer 1012 and compression insert 1014 are initially assembled and may be further assembled with the shank 1004 either prior or subsequent to implantation of the shank body 1006 into a vertebra 17, similar to the assembly 1 previously described herein and also as will be described in greater detail below. FIGS. 75 and 99, for example, further show a closure structure 1018 for capturing a longitudinal connecting member, for example, a rod 1021 which in turn engages the compression insert 1014 that presses against the shank head 1008 into fixed frictional contact with the retainer 1012, so as to capture, and fix the longitudinal connecting member 1021 within the receiver 1010 and thus fix the member 1021 relative to the vertebra 17. Substantially similar to the assembly 1 previously described herein, the receiver 1010 and the shank 1004 cooperate in such a manner that the receiver 1010 and the shank 1004 can be secured at any of a plurality of angles, articulations or rotational alignments relative to one another and within a selected range of angles both from side to side and from front to rear, to enable flexible or articulated engagement of the receiver 1010 with the shank 1004 until both are locked or fixed relative to each other near the end of an implantation procedure. The illustrated closure top 1018 and the rod 1021 are the same or substantially similar in form and function to the respective closure top 18 and rod 21 previously described herein with respect to the assembly 1, and thus shall not be re-described in this section.

The shank 1004 is also substantially similar in form, function and materials to the shank 4 previously described herein. Thus, the shank 1004 has a body 1006, a head 1008, a shank thread 1024, a neck 1026, a tip 1028, a shank body top 1032 where the thread 1024 terminates, a head spherical surface 1034, a head top edge 1038, a head upper frusto-conical surface 1039, an internal drive 1046 and a cannulation bore 1050 (not shown) the same or substantially similar to the respective shank body 6, head 8, shank thread 24, neck 26, tip 28, shank body top 32, head spherical surface 34, head top edge 38, head upper frusto-conical surface 39, internal drive 46 and bore 50 previously described herein with respect to the shank 4 of the assembly 1. Similar to the head hemisphere 40 of the shank 4, the illustrated shank head 1008 has a hemisphere location illustrated by a dotted line 1040.

With particular reference to FIGS. 75-79, the receiver 1010 is also substantially similar in form, function and materials to the receiver 10 previously described herein. However, there are a few differences between the receiver 10 and the receiver 1010 including spaced apertures 1056 extending through a base 1060 of the receiver 1010 and some geometry changes with respect to other apertures and inner surfaces defining a cavity, generally 1061, of the receiver 1010 which will be described in greater detail below. First, with respect to the similarities between the two receivers, the receiver 1010 includes outer curved surfaces 1058 and outer planar surfaces 1059 of the receiver base 1060, opposed arms 1062, inset surfaces 1063 between the arms 1062, a U-shaped channel 1064 having an upper opening 1066 and a seat 1068, arm inner planar surfaces 1069 on either side of a generally cylindrical inner arm surface, generally 1070, a guide and advancement structure 1072, arm top surfaces 1073, outer circular apertures 1074, outer cylindrical arm surfaces 1076, opposed through apertures 1077, opposed holding tabs 1078, tab sloping outer surfaces 1080 and 1081, tab top surfaces 1082, tab insert engaging surfaces 1084, tab lower surfaces 1085, tab inner lower sloping surfaces 1086, tab inner cylindrical surfaces 1087, tab side surfaces 1088, top surfaces 1089 of the apertures 1077, side surfaces 1090 of the apertures 1077 and U-shaped bottom surfaces 1091 of the apertures 1077, that are the same or substantially similar to respective outer curved surfaces 58 and outer planar surfaces 59 of the receiver base 60, opposed arms 62, inset surfaces 63 between the arms 62, the U-shaped channel 64 having the upper opening 66 and seat 68, arm inner planar surfaces 69, cylindrical inner arm surfaces, generally 70, guide and advancement structure 72, arm top surfaces 73, outer circular apertures 74, outer cylindrical arm surfaces 76, opposed through apertures 77, opposed holding tabs 78, tab sloping outer surfaces 80 and 81, tab top surfaces 82, tab insert engaging surfaces 84, tab lower surfaces 85, tab inner lower sloping surfaces 86, tab inner cylindrical surfaces 87, tab side surfaces 88, top surfaces 89 defining the apertures 77, side surfaces 90 defining the apertures 77 and U-shaped bottom surfaces 91 defining the apertures 1077 previously described herein with respect to the receiver 10. However, the U-shaped bottom surfaces 1091 are disposed lower within the receiver 1010 than the bottom surfaces 91 of the receiver 10. The U-shaped bottom surfaces 1091 are generally aligned with and spaced from the through apertures 1056, each of the curved bottom surfaces 1091 and the lower surfaces defining the apertures 1056 being approximately the same distance from a receiver bottom surface 1108, allowing for receipt therethrough of tooling (not shown) used to evenly and equally press inwardly on outer tangs of the retainer 1012 during assembly of the retainer with the other bone screw components as will be described in greater detail below.

With further reference to the receiver inner cavity 1061 that is substantially similar, but not identical to the cavity 61 of the receiver 10, there are arm inner cylindrical surfaces 1092 located directly under the guide and advancement structure 1072, similar to the surface 92 located under the guide and advancement structure 72 of the receiver 10. The receiver 1010 also has a radially inwardly located inner cylindrical surface 1095 that is similar to the surface 95 of the receiver 10. Like the surface 95, the surface 1095 is sized and shaped for a locking interference fit with the insert 1015. Like the surface 95, the surface 1095 defines an upper portion of the receiver base 1060 and also is adjacent to a chamber ceiling surface 1096. However, the receiver 10 surface 92 is located next to the surface 95, whereas in the receiver 1010, other cylindrical surfaces that vary slightly in diameter from one another are located between the surface 1095 and the surface 1092, namely, they are cylindrical surfaces 1093 and 1094. The stepped surface 1094' is the same or similar to the surface 94 of the receiver 10. Unlike the receiver 10, the upper surface 1096 defining the receiver chamber or cavity extends outwardly radially to a cylindrical surface 1098. The receiver 1010 does not include an equivalent to the receiver surface 97. A remainder of the receiver cavity 1061 is substantially similar to the cavity 61, the receiver cavity 1061 being defined by the expansion chamber surface 1098 and surfaces defining a seat for the retainer 1012, including cylindrical surfaces 1100 and 1101, annular seats 1102 and 1103, a transition stepped surface 1104, a circular rim or edge 1106, a frusto-conical surface 1107, a base bottom surface 1108 and a lower opening 1110, the same or similar in form and function to the respective cylindrical surface 98, surfaces defining the seat for the retainer 12, including cylindrical surfaces 100 and 101, annular seats 102 and 103, transition stepped surface 104, circular rim or edge 106, frusto-conical or flared surface 107, base bottom surface 108 and the lower opening 110 of the receiver 10 previously described herein.

With particular reference to FIGS. 75 and 80-86, the lower open or split friction fit retainer 1012, that operates to capture the shank upper portion 1008 within the receiver 1010 is shown. In certain stages of assembly and operation, the retainer 1012 is partially constrained within the receiver, being captured within the receiver cavity 1061 at a location below the surface 1096, the retainer 1012 being rotatable with respect to the receiver, but not pivotable thereto and not readily removable out of the receiver once deployed downward into the receiver cavity 1061. The retainer 1012 has a central axis that is operationally the same as a central axis associated with the receiver 1010 when the shank upper portion 1008 and the retainer 1012 are installed within the receiver 1010. The retainer 1012 includes a body 1115 having an outer surface 1116, upstanding inner panels or tangs 1117 and upstanding outer panels 1118 that are similar, but not identical in form and function to the respective retainer body 115 with outer surface 116, inner 117 and outer 118 panels previously described herein with respect to the assembly 1. As compared to the retainer 12, the retainer 1012 outer body surface 1116 is an outer cylinder broken only by a retainer slit 1148. Furthermore, the inner and outer retainer tangs are formed in a manner differently from that of the retainer 112 (a machining turning or spun process), providing for more radiused surfaces. There are three inner panels 117 and six outer panels 118. However, it is foreseen that there may be fewer or greater numbers of inner and outer panels.

Like the retainer 12 lower skirt 121, the retainer 1012 includes a lower outer cylindrical skirt or surface 1121 that is located beneath the panels 1118. The retainer 1012 further includes an additional lower or bottom skirt 1121' that is frusto-conical in form and extends downwardly and radially inwardly to a bottom surface 1122. The retainer 1012 also includes inner panel outer surfaces 1128, inner panel radiused surfaces 1129, inner panel top surfaces 1130, outer panel surfaces 1132, outer panel inner surfaces 1133 and outer panel top surfaces 1134 that are substantially similar in form and function to the respective inner panel outer surfaces 128, inner panel radiused surfaces 129, inner panel top surfaces 130, outer panel outer surfaces 132, outer panel inner surfaces 133 and outer panel top surfaces 134 previously described herein with respect to the retainer 12. With particular reference to FIG. 81, the retainer 1012 further includes ridges 1135 located on the panel outer surfaces 1132 for temporary frictional engagement with the receiver surface 1095 during assembly as will be described in greater detail below. It is foreseen that the ridges 1135 may be replaced with other types of surface treatment to provide an increased coefficient of friction between the retainer and the receiver, such as knurling or other roughening surface treatments.

The retainer 1012 has a central channel, generally 1141, an inner frusto-conical surface 1143, an inner cylindrical surface 1145, an inner stepped surface 1146 having an edge 1147, a slit, generally 1148, curvate, cupped surfaces 1149 and first and second surfaces 1152 and 1153 defining the slit 1148 that are the same or similar in form and function to the respective central channel 141, inner frusto-conical surface 143, inner cylindrical surface 145, inner stepped surface 146 having an edge 147, the slit, generally 148, curvate, cupped surfaces 149 and the first and second surfaces 152 and 153 defining the slit 148. Unlike the retainer 12, because of the lower skirt 1121', the shank engagement edge 1147 and the cupped surfaces 1149 are located relatively lower within the inner shank final engagement and locking mechanism of the retainer 1012 than the edge 147 and cupped surfaces 149 of the retainer 12, providing for greater and improved polyaxial motion of the assembly.

Like the retainer 12, the retainer 1012 is made from a resilient material, such as a stainless steel or titanium alloy, so that the retainer body 1115 may be expanded and the tabs or panels 1117 and 1118 of the retainer may be manipulated during various steps of assembly as will be described in greater detail below. The rotatability of the semi-constrained retainer 1012 with respect to the receiver 1010 allows for manipulation and placement of the retainer with respect to the shank to result in an increased angle of articulation at a location desired by a surgeon.

With particular reference to FIGS. 75 and 87-89, the locking compression insert 1014 is illustrated that is sized and shaped to be received by and down-loaded into the receiver 1010 at the upper opening 1066. The compression insert 1014 is so substantially similar to the insert 14 previously described herein that it will not be discussed further, except to identify the reference numerals that point to the various features. Thus, the insert 1014 includes a body 1156, arms 1157, cylindrical body surfaces 1158, interference fit surfaces 1159, arm outer surfaces 1160, a lower cylindrical surface 1161 a sloping ledge transition surface 1162, a planar bottom 1164, arm top surfaces 1165, through apertures 1167, shallow apertures 1168, grooves 1170, a through bore 1171, a U-shaped channel or saddle 1173, a saddle seat 1174, an inner cylindrical surface 1176, a lower radiused surface 1178 and a shank gripping portion 1180 that are the same or substantially similar in form, function and materials to the respective body 156, arms 157, cylindrical body surfaces 158, interference fit surfaces 159, arm outer surfaces 160, lower cylindrical surface 161, sloping ledge transition surface 162, planar bottom 164, arm top surfaces 165, through apertures 167, shallow apertures 168, grooves 170, through bore 171, saddle 173, saddle seat 174, inner cylindrical surface 176, lower radiused surface 178 and shank gripping portion 180 of the insert 14 previously described herein.

Figure 90:
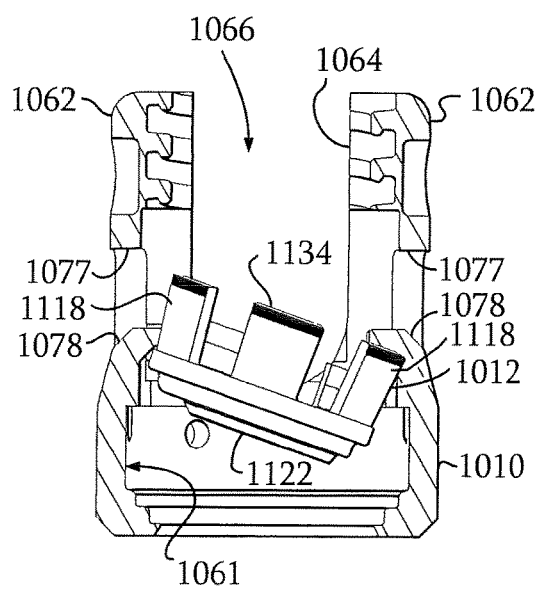
FIG. 90 is an enlarged front elevational view of the retainer and receiver of FIG. 75 with portions of the receiver broken away to show the detail thereof, the retainer being shown downloaded into the receiver to a partially inserted stage of assembly.
Figure 91:
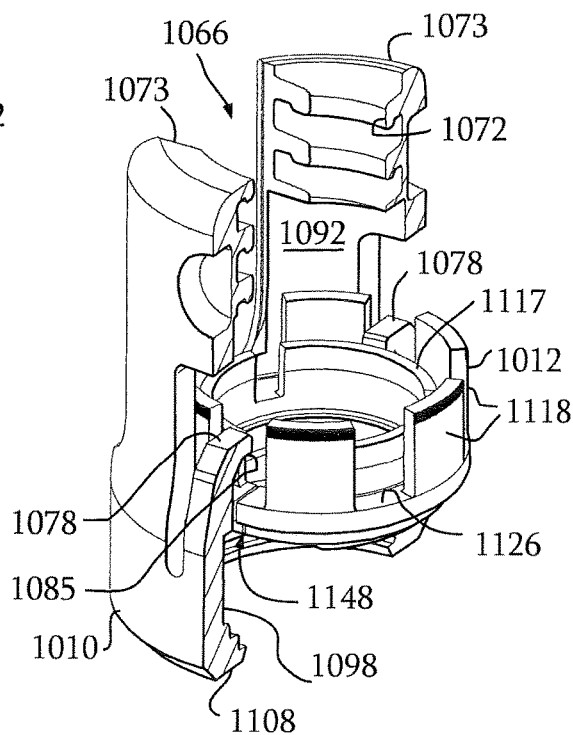
FIG. 91 is a perspective view of the retainer and receiver with portions broken away, similar to what is shown in FIG. 90, showing the retainer in a subsequent stage of assembly and in a maximum state of compression.

Pre-assembly of the receiver 1010, retainer 1012 and compression insert 1014 is shown in FIGS. 90-94. With particular reference to FIG. 90, first the retainer 1012 is inserted into the upper receiver opening 1066, leading with the outer panels 1118 with the panel 1118 top surfaces 1134 facing one arm 1062 and the retainer bottom surface 1122 facing the opposing arm 1062. The retainer 1012 is then lowered in such sideways manner into the channel 1064 and partially into the receiver cavity 1061, followed by tilting the retainer 1012 such that at least one panel top surface 1134 is located beneath the surface 1085 of one of the receiver holding tabs 1078 and the opposed holding tab 1078 is located generally between a pair of panels 1118, for example, at or near the retainer slit 1148 as shown in FIG. 91. Then, with further reference to FIG. 91, the retainer 1012 is tilted into a position wherein the central axis of the retainer 1012 is generally aligned with the receiver central axis and the receiver holding tabs 1078 are each located between pairs of adjacent panels 1118 and extend over retainer body top surfaces 1126 located opposite one another, with each tab surface 1085 being located directly above a top surface 1126 or the slit 1148. FIG. 91 also illustrates the retainer 1012 at a compressed state with the slit surfaces 1152 and 1153 being at a near touching state so that the retainer cylindrical surface slides past the receiver inner surface 1095.

Figure 92:
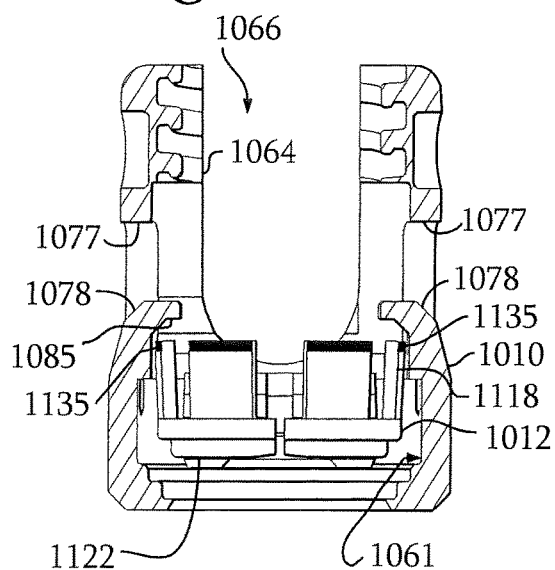
FIG. 92 is a front elevational view of the retainer and receiver with portions broken away, similar to what is shown in FIG. 91, showing the retainer positioned below the receiver spring tabs and also rotated about a central axis thereof, such rotation not necessary for assembly but provided herein to aid in viewing the drawings.
Figure 93:
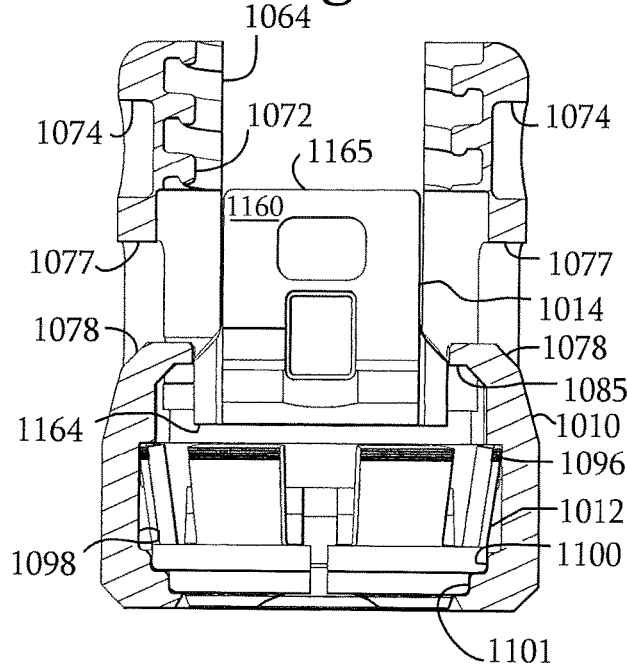
FIG. 93 is an enlarged front elevational view of the retainer and receiver with portions broken away, similar to what is shown in FIG. 27, showing the retainer fully deployed within the receiver cavity and further including the insert in side elevation, being downloaded into the receiver and at a location suitable for rotation within the receiver.

With reference to FIG. 92, after the panels 1118 are located between holding tabs 1078, the retainer 1012 is lowered into the receiver cavity 1061 with the resilient panels 1118 being pressed inwardly, using tooling, or by the use of a downward force that results in compression of the panels 1118 toward the receiver central axis. With reference to FIG. 93, the retainer 1012 is pressed past the receiver surfaces 1095 and allowed to "deploy", the tangs 1118 expanding to a neutral or near neutral state after dropping into the cavity defined primarily by the cylindrical surface 1098, the outer tangs 1118 located beneath the surface 1096, capturing the retainer 1012 within the receiver cavity 1061. With reference to FIGS. 93 and 94, at this time the insert 1014 is dropped into the receiver channel 1064 and then rotated into place in a manner the same as described previously herein with respect to the insert 14 and the receiver 10. Tools (not shown) are then inserted through the receiver apertures 1056 and above the U-shaped surfaces 1091 of the apertures 1077 to press inwardly on the retainer tangs 1118 as shown in FIG. 94 and then the retainer 1012 is moved upwardly within the cavity 1061 as shown in FIG. 95. The tooling is released and the retainer tang outer surfaces having the ridges 1135 abut against the receiver surfaces 1095 and are frictionally engaged therewith. The retainer 1012 is now captured between the surfaces 1095 and located at a desired space in the receiver 1010 for both shipping and for further assembly with the shank 1004. The insert 1014 is also fully captured within the receiver 1010 by the guide and advancement structure 1072 prohibiting movement of the insert 1014 up and out through the receiver opening 1066 as well as by retainer 1012 located below the insert.

With reference to FIG. 95, the pre-assembled receiver, insert and retainer are placed above the shank upper portion 1008 until the shank upper portion is received within the opening 1110. With particular reference to FIGS. 95-98, as the shank upper portion 1008 is moved into the interior 1061 of the receiver base, the shank upper portion 1008 presses upwardly against the retainer 1012 in the receiver recess partially defined by the cylindrical surface 1098. As the shank head 1008 continues to move upwardly toward the channel 1064, the shank head surface 1034 forces the retainer 1012 against the insert 1014. However, the insert 1014 is prohibited from moving upward by the receiver guide and advancement structure 1072. Therefore, the upwardly moving shank head 1008 forces a widening of the retainer slit 1148 and corresponding outward movement of the body 1115 of the retainer 1012 towards the receiver cylindrical surfaces 1098, 1100 and 1101 defining the receiver expansion recess or chamber as best shown in FIG. 96, while the retainer tangs 1118 near the top surfaces 1134 thereof are generally maintained in a location directly below the insert 1014 bottom surface 1164. At this time, the spherical surface 1034 of the head 1008 comes into contact with the retainer inner cylindrical body 1145 and the edge 1147. With reference to FIG. 97, the retainer 1012 begins to return towards a neutral or nominal state as the center of the sphere of the shank head 1008 passes beyond the retainer surface 1147. By the time the hemisphere of the spherical surface 1034 extends into a desired captured location within the retainer central channel 1141, the shank surface 1034 is in contact with the edge 1147 as well as with the inner panels 1117 at surfaces 1129. The combination of the rim or edge 1147 surface contact and the panel 1117 surfaces 1129 contact resiliently pressing against the radiused surface 1034, provides a fairly tight friction fit between the head 1008 and the retainer 1012, the surface 1034 being pivotable with respect to the retainer 1012 with some force. Thus, a tight, non-floppy ball and socket joint is now created between the retainer 1012 and the shank upper portion 1008.

With reference to FIG. 98, the receiver is then pulled upwardly or the shank 1004 and attached retainer 1012 are then moved manually downwardly into a position wherein the retainer panels 1118 are disengaged from the receiver surfaces 1095, allowing the panels 1118 to resiliently release and extend outwardly into a neutral or near-neutral position at a location below the receiver annular surface 1096 that defines the ceiling of the receiver inner chamber 1061. The panels 1118 are now captured within the receiver and the retainer with any upward movement resulting in the panel top surfaces 1134 abutting against the receiver surfaces 1096. However, although fully captured, the retainer/shank combination is advantageously only partially restrained with respect to the receiver, as a user is able to rotate the retainer 1012 about the receiver 1010 central axis prior to locking of the shank 1004 with respect to the receiver 1010. At this time also, the retainer is fully seated on the receiver surfaces 1102 and 1103 and the surfaces 1116 and 1121 are pressed outwardly into abutting relationship with the receiver with the lower skirt 1121' spaced from the receiver flared surface 1107 and the retainer bottom surface 1122 in approximately the same plane as the receiver bottom surface 1108. With reference to FIG. 100, downward pressure of the shank head 1008 on the retainer edge 1147 further expands the retainer body 1115 outwardly, the retainer body formed in part by the lower skirt surfaces 1121 and 1121' advantageously allows for the head 1008 to seat lower within the receiver than in other known polyaxial bone anchors as well as lower than that shown in the assembly 1. The skirt feature thus allows for a more stable lower seating surface in combination with the retainer cupped surface 1149 that allows for increased angular orientation of the shank with respect to the retainer, and thus with respect to the entire bone screw assembly, such an angular increase being possible without the need to provide a cut-out or cupped surface at and near the receiver bottom 1108. Also advantageous is the fact that the partially constrained retainer 1012 may be rotated with respect to the receiver 1010 about the receiver central axis, allowing for the user to choose the location of the increased angle of orientation between the receiver 1010 and the shank 1004.

With reference to FIG. 98, after the retainer 1012 is moved downwardly into the receiver 1010 and seated on the surfaces 1102 and 1103, the insert 1014 remains located spaced above the shank head 1008 as the receiver spring tabs 1078 and/or the receiver stepped surface 1094 prohibits downward movement of the insert 1014 unless a downward force is applied on the insert either by a tool or the rod 1021 and closure top 1018 shown in FIG. 99, for example and discussed previously herein with respect to the almost identical locking insert 1014. At this time, prior to locking with a closure top, the receiver 1010 may be articulated to a desired angular position with respect to the shank 4 (such as the angular orientations shown in FIGS. 101 and 102, for example), that will be held, but not locked, by the frictional engagement between the retainer 1012 inner panels 1117 and the shank upper portion 1008. As discussed above with respect to the assembly 1, at this time, the lock and release insert 1014 may be pressed into interference fit relationship with the receiver surfaces 1095 by a tool or by the closure top 1018 pressing down upon the rod 1021 that in turn presses down upon the insert 1014 as shown in FIGS. 99 and 100. The assembly 1001 may be outfitted with a deformable rod and cooperating closure as previously described herein with respect to the assembly 1. The insert 1014 may also be unlocked as described above with respect to the assembly 1.

Figure 101:
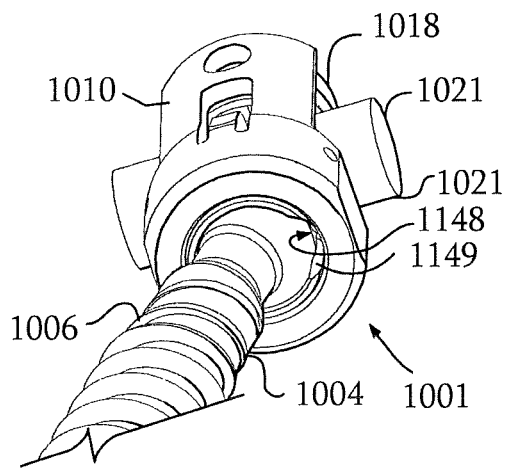
FIG. 101 is an enlarged and partial perspective view of the assembly of FIG. 75, shown fully assembled with the shank disposed at a twenty degree (cephalad) angle with respect to the receiver.
Figure 102:
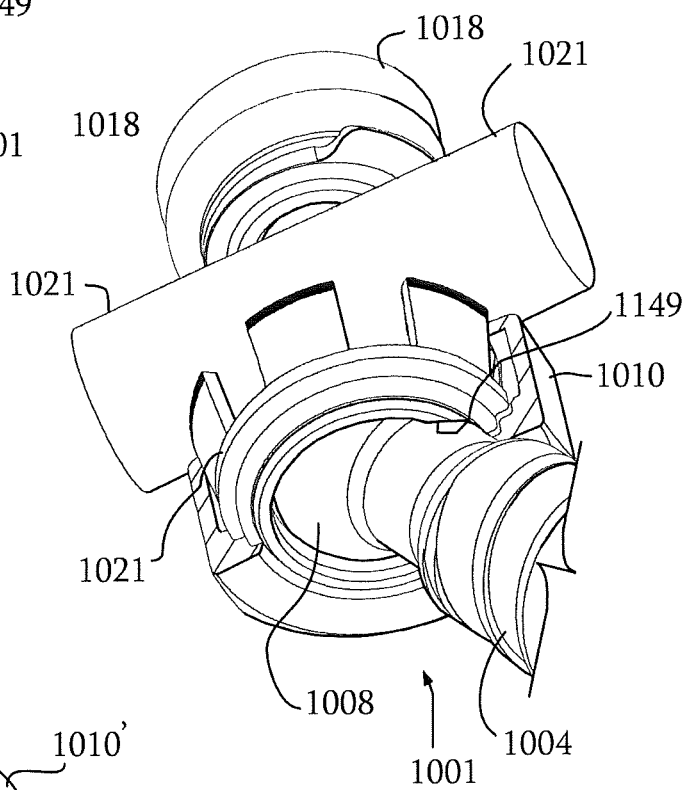
FIG. 102 is an enlarged and partial perspective view of the assembly of FIG. 75, shown fully assembled with the shank disposed at a thirty degree (caudad) angle with respect to the receiver.
Figure 103:
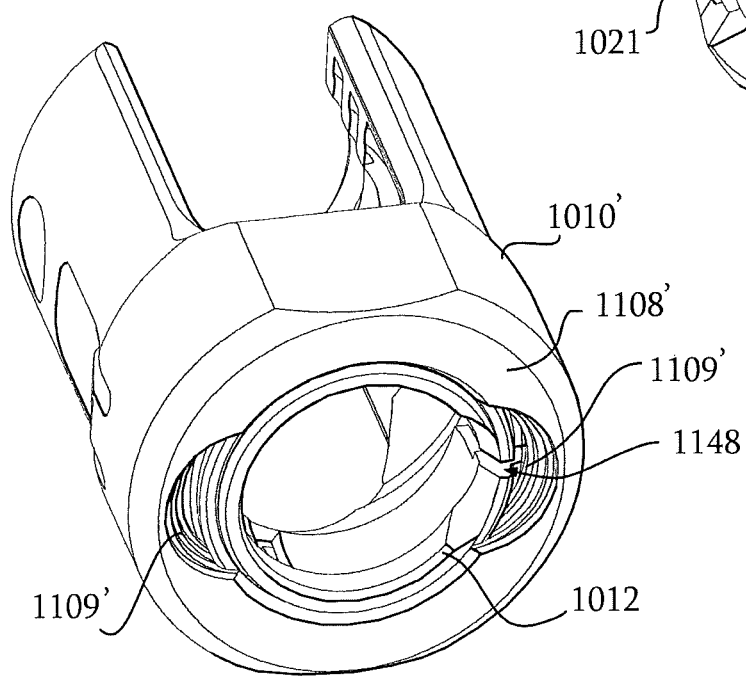
FIG. 103 is an enlarged perspective view of an alternative favored angle receiver according to the invention having opposed lower concave stepped surfaces, shown cooperating with the retainer of FIG. 75.

With reference to FIGS. 101-103, different angular or articulated positions of the shank 1004 with respect to the receiver 1010 are shown, some making full use of the slit 1148 and adjacent cut-out or cupped surfaces 1149 of the retainer 1112. For example, in FIG. 102, the shank 1008 is pivoted toward and into engagement with the cupped surfaces 1149 (about thirty degree articulation) as compared to the arrangement shown in FIG. 101, wherein the shank 1004 is pivoted in a direction opposite to the retainer slit 1148 and the surfaces 1149 (about twenty degree articulation).

FIG. 103 illustrates an alternative receiver 1010' that includes a bottom surface 1108' further defined by a pair of opposed, stepped and concave curved bottom surfaces 1109'. Otherwise, the receiver 1010' is identical to the receiver 1010 described above and thus fully cooperates with the retainer 1012, insert 1014, shank 1004, rod 1021 and closure top 1018 in a manner substantially identical to what has been described above with respect to the assembly 1001. FIG. 103 shows the retainer 1012 mounted in the receiver 1010' with the retainer slit 1148 and surfaces 1149 aligned with one of the stepped surfaces 1109', such alignment providing for at least a forty degree angle of articulation between the shank 1004 and the receiver 1010'.

Figure 105:
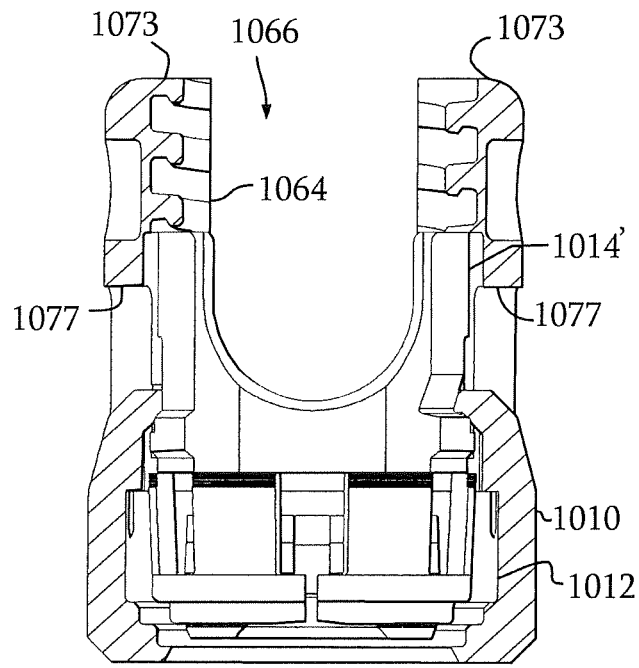
FIG. 105 is an enlarged front elevational view of the alternative insert of FIG. 104 shown in a stage of assembly with the receiver and retainer of FIG. 75, with portions broken away to show the detail thereof.
Figure 106:
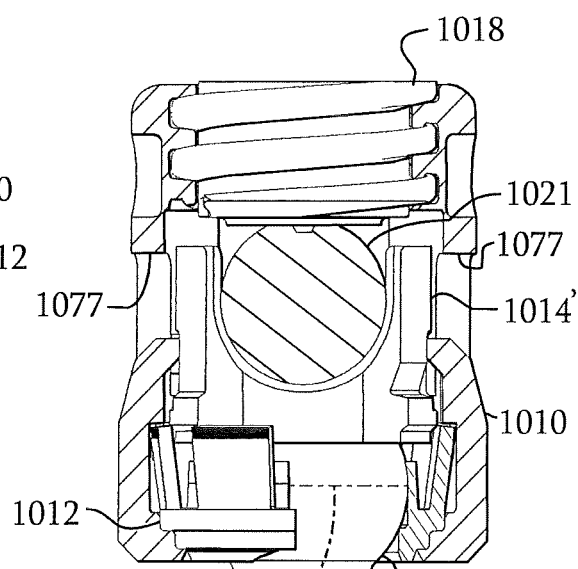
FIG. 106 is an enlarged and partial front elevational view of the receiver, retainer, rod and closure top of FIG. 75 shown fully assembled with the alternative insert of FIG. 104, also in front elevation, with portions broken away to show the detail thereof.
Figure 104:
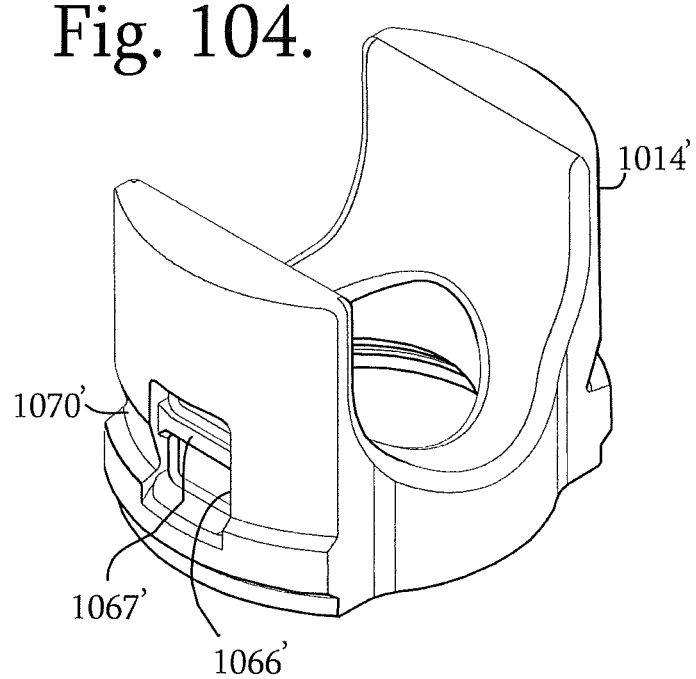
FIG. 104 is an enlarged perspective view of an alternative non-locking insert according to the invention for use in lieu of the locking insert shown in FIG. 75.

With reference to FIGS. 104-106, an alternative non-locking compression insert 1014' is illustrated for use with the shank 1004, receiver 1010, retainer 1012, closure top 1018 and rod 1021 previously described herein. The insert 1014' is substantially similar to the non-locking insert 214 previously described herein. During assembly with the receiver, the insert 1014' is rotated and the receiver holding tab surfaces 1084 slide along grooves 1070' until they spring into the apertures 1066' having bars 1067' that are the same or similar to the apertures and bars 267 previously described herein with respect to the insert 214. The bars 1067' hold the non-locking insert 1014' in place above the retainer 1012 until placed into locking engagement with the shank head 1008 by pressure from the rod 1021 and closure top 1018.

With reference to FIGS. 107-137, the reference number 2001 generally represents another alternative polyaxial bone screw apparatus or assembly according to the present invention. The assembly 2001 includes a shank 2004; a receiver 2010; a friction fit retainer 2012, and a crown-like compression or pressure insert 2014. There are many similarities between the assembly 2001 and the assemblies 1 and 1001. However, the assembly 2001 differs from the assembly 1001 and the assembly 1 in how the retainer 2012 is deployed within the receiver 2010 which also changes how the shank 2004 is "popped" into the mechanism as a whole. These differences mainly concern the sizing of certain receiver 2010 surfaces with respect to the retainer 2012 so as to provide an abutment surface for the retainer that results in a subsequent interference fit between the retainer 2012 and the receiver 2010. Also, ridges or other high friction coefficient treatments on a head 2008 of the shank 2004 provide for gripping between the shank 2004 the retainer 2012 during certain assembly steps. Like the retainer 1012, the retainer 2012 includes an additional lower outer tier or skirt cooperating with the receiver 2010 that allows for a low profile, similar to the assembly 1001, previously described herein. FIGS. 107, 130 and 131, for example, further show a closure structure 2018 for capturing a longitudinal connecting member, for example, a rod 2021 which in turn engages the compression insert 2014 that presses against the shank head 2008 into fixed frictional contact with the retainer 2012, so as to capture, and fix the longitudinal connecting member 2021 within the receiver 2010 and thus fix the member 2021 relative to the vertebra 17. Substantially similar to the assemblies 1 and 1001 previously described herein, the receiver 2010 and the shank 2004 cooperate in such a manner that the receiver 2010 and the shank 2004 can be secured at any of a plurality of angles, articulations or rotational alignments relative to one another and within a selected range of angles both from side to side and from front to rear, to enable flexible or articulated engagement of the receiver 2010 with the shank 2004 until both are locked or fixed relative to each other near the end of an implantation procedure. The illustrated closure top 2018 and the rod 2021 are the same or substantially similar in form and function to the respective closure top 18 and rod 21 previously described herein with respect to the assembly 1, and thus shall not be re-described in this section. Furthermore, FIG. 132 illustrates an alternative deformable rod 2021' and cooperating closure top 2018' that are identical or substantially similar to the respective deformable rod 21' and closure top 18' previously described herein.

The shank 2004 is substantially similar in form, function and materials to the shank 4 previously described herein. Thus, the shank 2004 has a body 2006, a head 2008, a shank thread 2024, a neck 2026, a tip 2028, a shank body top 2032 where the thread 2024 terminates, a head spherical surface 2034, a head top edge 2038, a head upper frusto-conical surface 2039, an internal drive 2046 and a cannulation bore 2050 the same or substantially similar to the respective shank body 6, head 8, shank thread 24, neck 26, tip 28, shank body top 32, head spherical surface 34, head top edge 38, head upper frusto-conical surface 39, internal drive 46 and bore 50 previously described herein with respect to the shank 4 of the assembly 1. Furthermore, at a location directly beneath a hemisphere of the head 2008, the shank surface 2034 includes a plurality of parallel ridges 2035, running about the head 2008 and parallel to the plane of the circular shank top edge 2038. The ridges 2035 aid the retainer in gripping the shank head 2008 during certain assembly steps as shown, for example, in FIGS. 127 and 128 and described in greater detail below.

Figure 109:
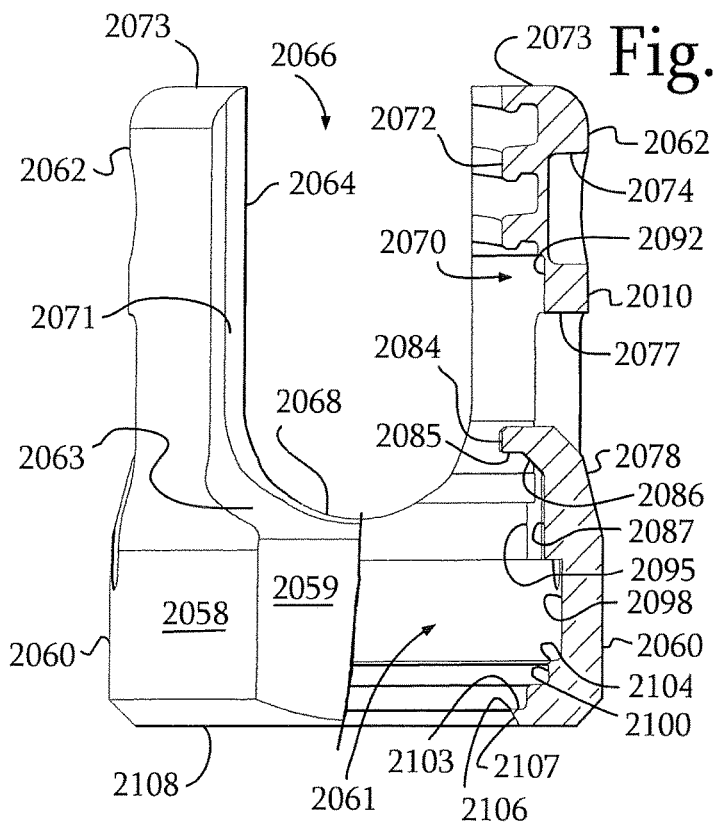
FIG. 109 is an enlarged front elevational view of the receiver of FIG. 107 with portions broken away to show the detail thereof.
Figure 110:
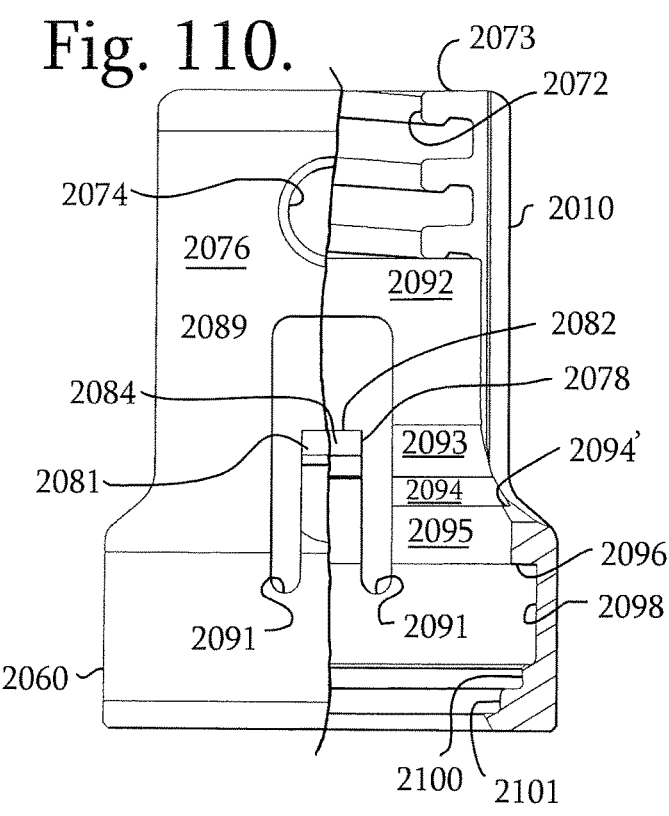
FIG. 110 is side elevational view of the receiver of FIG. 109 with portions broken away to show the detail thereof.
Figure 111:
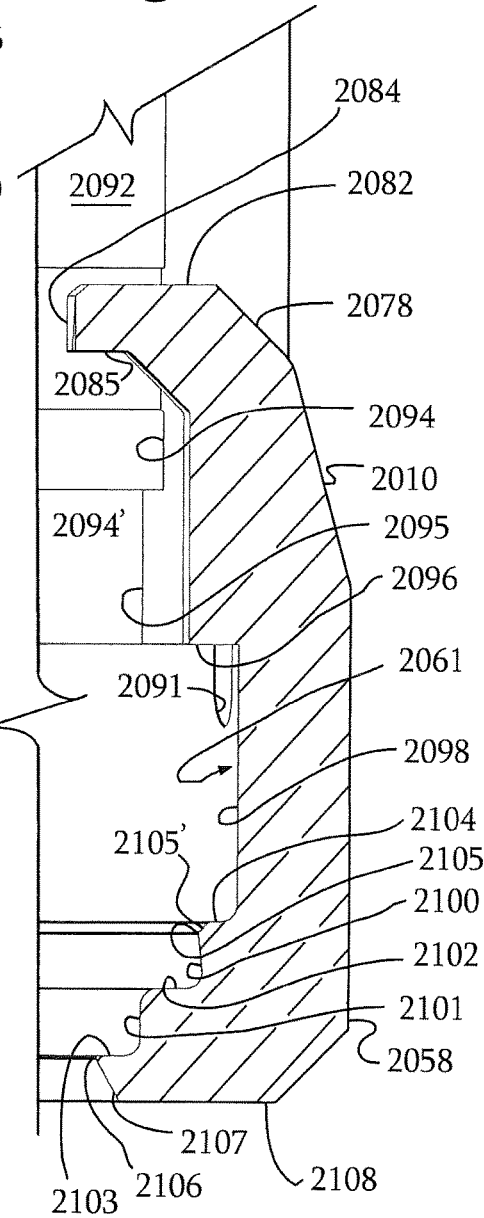
FIG. 111 is an enlarged an partial front elevational view of the receiver of FIG. 109.
Figure 112:
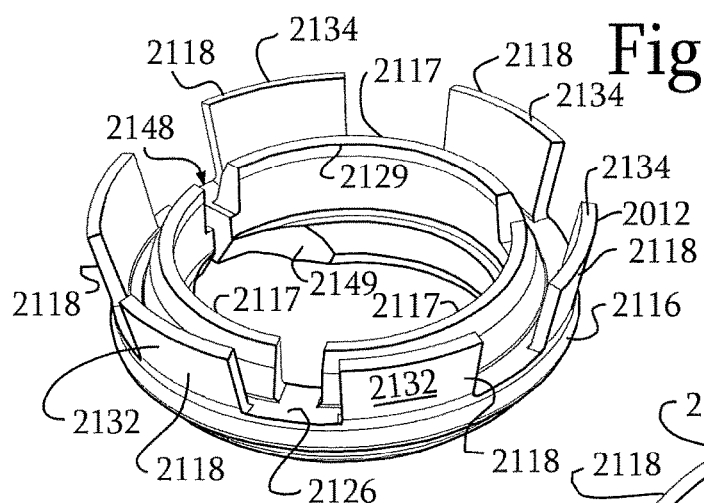
FIG. 112 is an enlarged perspective view of the retainer of FIG. 107.
Figure 113:
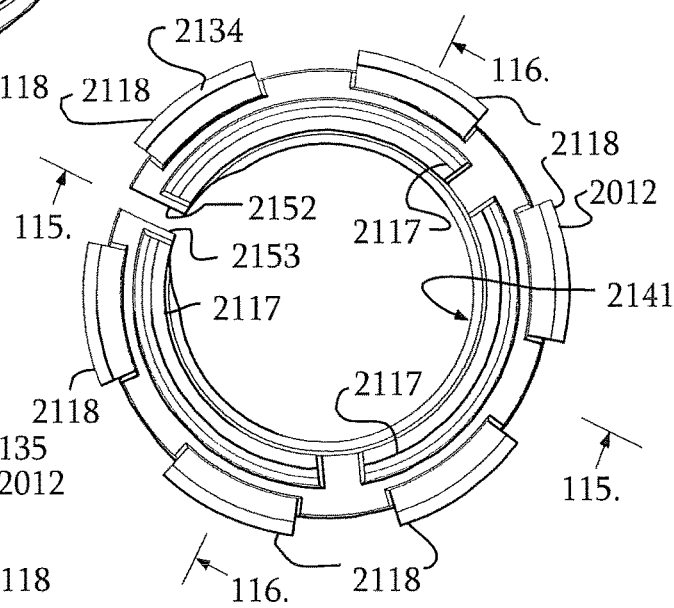
FIG. 113 is a top plan view of the retainer of FIG. 112.
Figure 114:
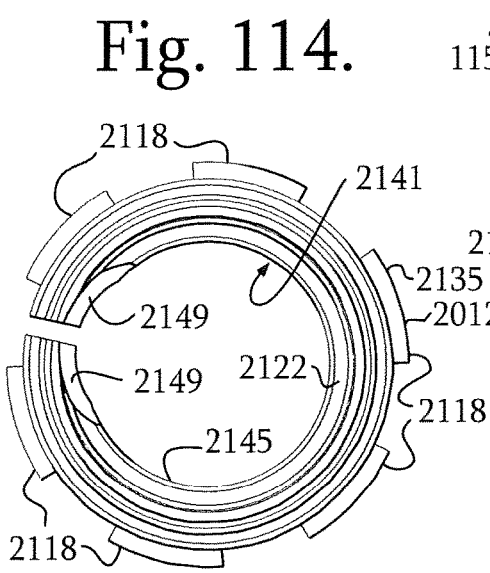
FIG. 114 is a reduced bottom plan view of the retainer of FIG. 112.
Figure 115:
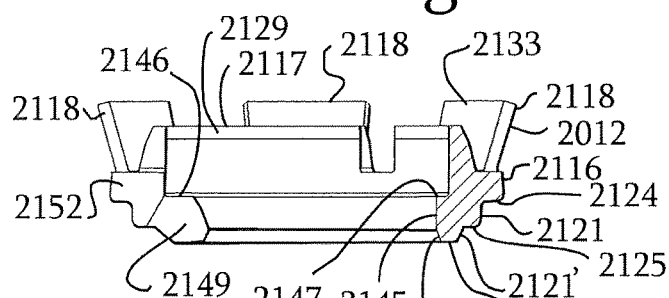
FIG. 115 is a reduced cross-sectional view taken along the line 115-115 of FIG. 113.
Figure 116:
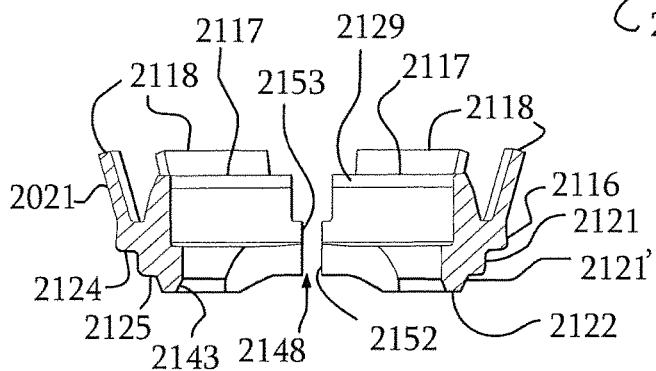
FIG. 116 is a reduced cross-sectional view taken along the line 116-116 of FIG. 113.

With particular reference to FIGS. 109-111, the receiver 2010 is substantially similar in form, function and materials to the receivers 1010 and 10 previously described herein. However, there are a few differences between the receiver 2010 and the receiver 1010 as the receiver 2010 does not include the spaced apertures 1056, but otherwise includes seating surfaces described in greater detail below that provide a stop for holding the retainer 2012 in a desired position during certain assembly steps and a later interference type fit between the retainer 2012 and the receiver 2010. First, with respect to the similarities between the receivers, the receiver 2010 includes outer curved surfaces 2058 and outer planar surfaces 2059 of the receiver base 2060, opposed arms 2062, inset surfaces 2063 between the arms 2062, a U-shaped channel 2064 having an upper opening 2066 and a seat 2068, arm inner planar surfaces 2069 on either side of a generally cylindrical inner arm surface, generally 2070, a guide and advancement structure 2072, arm top surfaces 2073, outer circular apertures 2074, outer cylindrical arm surfaces 2076, opposed through apertures 2077, opposed holding tabs 2078, tab sloping outer surfaces 2080 and 2081, tab top surfaces 2082, tab insert engaging surfaces 2084, tab lower surfaces 2085, tab inner lower sloping surfaces 2086, tab inner cylindrical surfaces 2087, tab side surfaces 2088, top surfaces 2089 of the apertures 2077, side surfaces 2090 of the apertures 2077 and U-shaped bottom surfaces 2091 of the apertures 2077, that are the same or substantially similar to respective outer curved surfaces 58 and outer planar surfaces 59 of the receiver base 60, opposed arms 62, inset surfaces 63 between the arms 62, the U-shaped channel 64 having the upper opening 66 and seat 68, arm inner planar surfaces 69, cylindrical inner arm surfaces, generally 70, guide and advancement structure 72, arm top surfaces 73, outer circular apertures 74, outer cylindrical arm surfaces 76, opposed through apertures 77, opposed holding tabs 78, tab sloping outer surfaces 80 and 81, tab top surfaces 82, tab insert engaging surfaces 84, tab lower surfaces 85, tab inner lower sloping surfaces 86, tab inner cylindrical surfaces 87, tab side surfaces 88, top surfaces 89 defining the apertures 77, side surfaces 90 defining the apertures 77 and U-shaped bottom surfaces 91 defining the apertures 1077 previously described herein with respect to the receiver 10.

With further reference to the receiver inner arm surfaces, generally 2070 and the cavity 2061, such surface features are substantially similar to the inner arm surface 1070 and the surfaces defining the cavity 1061 of the receiver 1010 of the assembly 1001, but not completely identical thereto. So, with respect to the similarities, the receiver 2010 includes inner arm surfaces 2092, 2093 and 2094 and step surfaces 2094' that are the same in form and function to the respective arms surfaces 1092, 1093, 1094 and step surface 1094' previously described herein with respect to the receiver 1010. Also, with respect to the surfaces defining the receiver cavity 2061, the receiver 2010 includes a cylindrical surface 2095, a chamber ceiling surface 2096, a cylindrical expansion chamber surface 2098 that are the same or substantially similar in form and function to the respective cylindrical surface 1095, chamber ceiling surface 1096 and cylindrical surface 1098 of the receiver 1010.

With regard to surfaces that define the retainer final seating portion of the chamber 2061, the receiver 2010 includes a lower cylindrical surface 2101, annular seating surfaces 2102 and 2103, a lower edge 2106, a flared surface 2107, a base bottom surface 2108 and a lower opening 2110 that are the same or substantially similar to the respective lower cylindrical surface 1101, annular seating surfaces 1102 and 1103, lower edge 1106, flared or frusto-conical surface 1107, base bottom surface 1108 and lower opening 1110 of the receiver 1010. With particular reference to FIG. 111, although somewhat similar the cylindrical surface 1101, the receiver 2010 surface that is located between the annular surface 2102 and a transition step 2104 differs from the surface 1104. The transition step 2104 also varies slightly from the transition step 1104 of the receiver 1010. In the receiver 2010, the beveled transition step 2104 extends further radially inwardly than the step 1104, providing a step edge 2105 and adjacent beveled or sloped surface 2105' that acts as a stop for the retainer 2012 (see FIG. 122) unless and until the retainer 2012 is forced into a close fit engagement with the edge 2105, force being required to move the retainer 2012 beyond the edge 2105 as shown in FIGS. 128 and 129 and as will be discussed in greater detail below. The surface 2100, rather than being parallel to a central axis of the receiver 2010, is angled slightly outwardly towards the receiver base surface 2058. Thus, unlike the receiver 1010 in which the surface 1100 is perpendicular to the surface 1102, in the receiver 2010, the surface 2100 is at an acute angle with respect to the surface 2102, albeit, only slightly less than ninety degrees. This slight slope of the surface 2100 allows for some clearance and ease in when moving the retainer 2012 past the edge 2105 and then down into abutment with the annular seating surfaces 2102 and 2103.

With particular reference to FIGS. 107 and 112-116, the lower open or split friction fit retainer 2012, that operates to capture the shank upper portion 2008 within the receiver 2010 is shown. Unlike the retainers 12 and 1012, in all stages of assembly with the shank 2004, and in subsequent operation, the retainer 2012 is partially constrained within the receiver, being captured within the receiver cavity 2061 at a location below the surface 2096, the retainer 1012 being rotatable with respect to the receiver, but not pivotable thereto and not readily removable out of the receiver once deployed downward into the receiver cavity 2061. The retainer 2012 has a central axis that is operationally the same as a central axis associated with the receiver 2010 when the shank upper portion 2008 and the retainer 2012 are installed within the receiver 2010. The retainer 2012 includes a body 2115 having an outer cylindrical surface 2116, upstanding inner panels or tangs 2117 and upstanding outer panels 2118 that are substantially similar to the respective body 1115, outer surface 1116, inner tangs 1117 and outer tangs 1118 previously described herein with respect to the assembly 1001. However, the outer tangs 2118 do not include outer ridges or other surface treatment because the retainer 2012 tangs 2118 are not compressed inwardly by the receiver during shipping or assembly with the shank 2008. The inner tangs 2117 also differ slightly from the tangs 1117 in that an inner radiused surface 2129 does not have quite as much surface area as the inner surface 1129. The sizing of the surface 2129 roughly corresponds to the sizing of the shank ridges 2035, providing optimal gripping between the shank head 2008 and the radiused surface 2129 for a desirable friction fit during manipulation of the shank 2004 with respect to the receiver 2010 prior to locking of the polyaxial mechanism of the assembly 2001. As with the retainer 1012, the retainer 2012 includes three inner panels 2117 and six outer panels 2118. However, it is foreseen that there may be fewer or greater numbers of inner and outer panels.

The retainer 2012 includes a cylindrical lower skirt 2121, a frusto-conical bottom skirt 2121' and a bottom surface 2122 that are substantially the same or similar to the respective skirt features 1121 and 1121' and bottom surface 1122 previously discussed herein with respect to the retainer 1012. Between the outer cylindrical surface 2116 and the skirt 2121 is a linking substantially planar annular surface 2124. Between the skirt 2121 and the bottom skirt 2121' is a linking substantially planar annular surface 2125. It is the surface 2124 that abuts against the receiver edge 2105 during certain assembly steps as shown, for example, in FIG. 122.

Other features of the retainer 2012 include tang 2117 outer surfaces 2128, inner radiused surfaces 2129, top surfaces 2130, tang 2118 outer surfaces 2132, inner surfaces 2133 and top surfaces 2134 that are similar to the respective retainer 1012 tang 1117 outer surfaces 1128, inner radiused surfaces 1129, top surfaces 1130, tang 1118 outer surfaces 1132, inner surfaces 1133 and top surfaces 1134. As stated above, the inner tang radiused surfaces 2129 do differ from the tang surfaces 1129 with respect to surface area, but otherwise similarly function to provide for friction fit during manipulation of the shank with respect to the retainer. The retainer 2012 further includes a central channel 2141, an inner frusto-conical surface 2143, an inner cylindrical surface 2145, a step surface 2146 and inner shank gripping edge 2147, a slit 2148, cupped or cut-out surfaces 2149 and surfaces 2152 and 2153 defining the slit 2148 that are the same or substantially similar to the respective central channel 1141, inner frusto-conical surface 1143, inner cylindrical surface 1145, step surface 1146 and inner shank gripping edge 1147, slit 1148, cupped or cut-out surfaces 1149 and surfaces 1152 and 1153 defining the slit 1148 of the retainer 1012 previously described herein.

Figure 117:
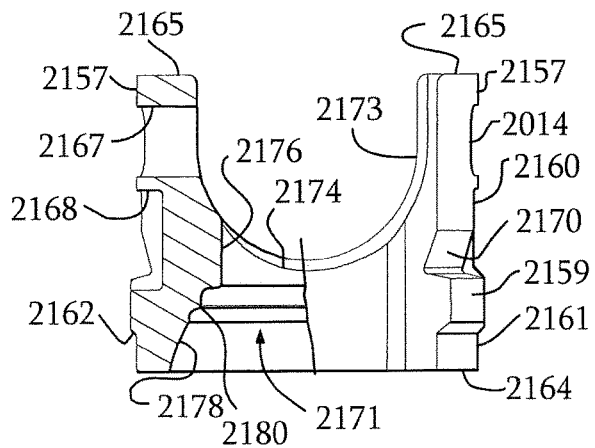
FIG. 117 is an enlarged front elevational view of the insert of FIG. 107 with portions broken away to show the detail thereof.
Figure 118:
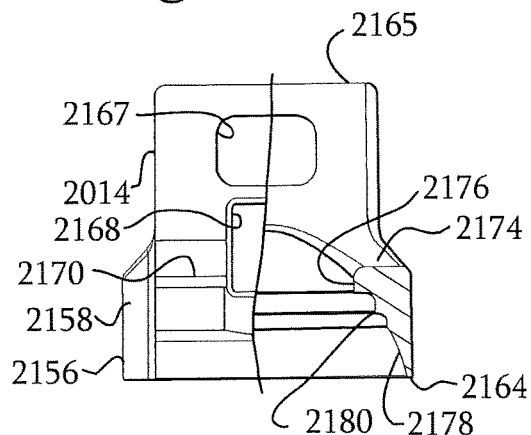
FIG. 118 is a side elevational view of the insert of FIG. 117 with portions broken away to show the detail thereof.

With particular reference to FIGS. 107 and 117-118, the locking compression insert 2014 is illustrated that is sized and shaped to be received by and down-loaded into the receiver 2010 at the upper opening 2066. The compression insert 2014 is so substantially similar to the inserts 14 and 1014 previously described herein that it will not be discussed further, except to identify the reference numerals that point to the various features. Thus, the insert 2014 includes a body 2156, arms 2157, cylindrical body surfaces 2158, interference fit surfaces 2159, arm outer surfaces 2160, a lower cylindrical surface 2161 a sloping ledge transition surface 2162, a planar bottom 2164, arm top surfaces 2165, through apertures 2167, shallow apertures 2168, grooves 2170, a through bore 2171, a U-shaped channel or saddle 2173, a saddle seat 2174, an inner cylindrical surface 2176, a lower radiused surface 2178 and a shank gripping portion 2180 that are the same or substantially similar in form, function and materials to the respective body 156, arms 157, cylindrical body surfaces 158, interference fit surfaces 159, arm outer surfaces 160, lower cylindrical surface 161, sloping ledge transition surface 162, planar bottom 164, arm top surfaces 165, through apertures 167, shallow apertures 168, grooves 170, through bore 171, saddle 173, saddle seat 174, inner cylindrical surface 176, lower radiused surface 178 and shank gripping portion 180 of the insert 14 previously described herein.

Figure 119:
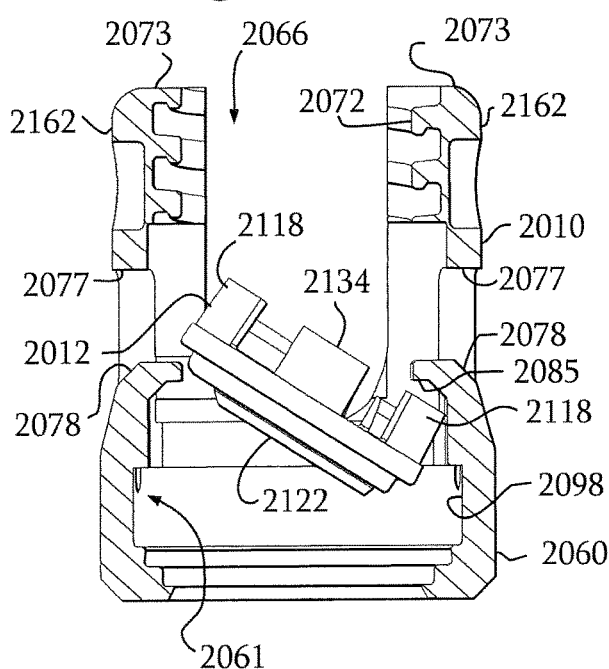
FIG. 119 is an enlarged front elevational view of the retainer and receiver of FIG. 107 with portions of the receiver broken away to show the detail thereof, the retainer being shown downloaded into the receiver to a partially inserted stage of assembly.
Figure 120:
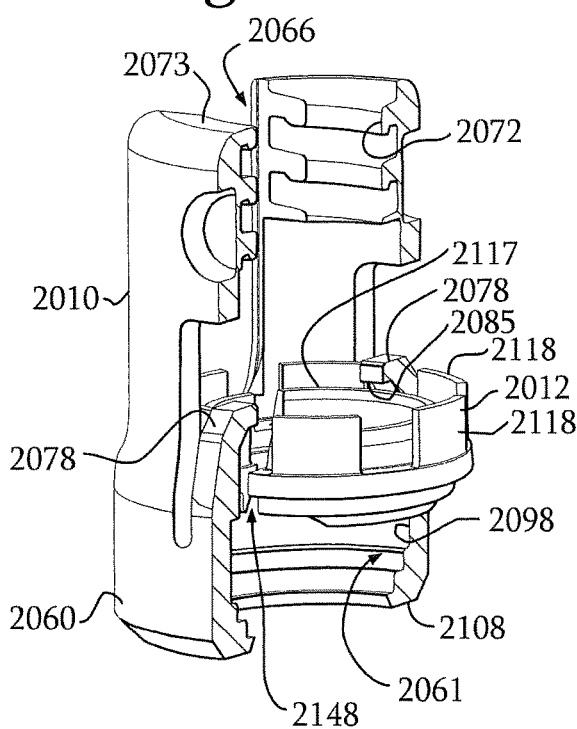

Pre-assembly of the receiver 2010, retainer 2012 and compression insert 2014 is shown in FIGS. 119-124. With particular reference to FIG. 119, first the retainer 2012 is inserted into the upper receiver opening 2066, leading with the outer panels 2118 with the panel 2118 top surfaces 2134 facing one arm 2062 and the retainer bottom surface 2122 facing the opposing arm 2062. The retainer 2012 is then lowered in such sideways manner into the channel 2064 and partially into the receiver cavity 2061, followed by tilting the retainer 2012 such that at least one panel top surface 2134 is located beneath the surface 2085 of one of the receiver holding tabs 2078 and the opposed holding tab 2078 is located generally between a pair of panels 2118, for example, at or near the retainer slit 2148 as shown in FIG. 120. Then, the retainer 2012 is tilted into a position wherein the central axis of the retainer 2012 is generally aligned with the receiver central axis and the receiver holding tabs 2078 are each located between pairs of adjacent panels 2118 and extend over retainer body top surfaces 2126 located opposite one another, with each tab surface 2085 being located directly above a top surface 2126 or the slit 2148. FIG. 120 also illustrates the retainer 2012 at a compressed state with the slit 2148 surfaces 2152 and 2153 being at a near touching state so that the retainer cylindrical surface slides past the receiver inner surface 2095.

After the panels 2118 are located between holding tabs 2078, the retainer 2012 is lowered into the receiver cavity 2061 with the resilient panels 2118 being pressed inwardly, using tooling, or by the use of a downward force that results in compression of the panels 2118 toward the receiver central axis. With reference to FIG. 121, the retainer 2012 is pressed past the receiver surfaces 2095 and allowed to "deploy", the tangs 2118 expanding after dropping into the cavity defined primarily by the cylindrical surface 2098, the outer tangs 2118 located beneath the surface 2096, capturing the retainer 2012 within the receiver cavity 2061. With reference to FIG. 122, at this time also, the retainer 2012 is prohibited from moving into a fully seated position within the lower portion of the receiver cavity 2061. The Edge 2105 and adjacent surface 2105' provide an abutment stop with the retainer annular surface 2124 being temporarily seated thereupon. Downward force is required to move the retainer 2012 into a fully seating position with the receiver surfaces 2102 and 2103. Therefore, the retainer is advantageously prohibited at this time from moving down past the edge 2105 or moving up past the surface 2096 because of the outward deployment of the tangs 2118. With reference to FIG. 123, at this time the insert 2014 is dropped into the receiver channel 2064 and then rotated into place (see FIG. 124) in a manner the same as described previously herein with respect to the insert 14 and the receiver 10. Now, the insert 1014 is also fully captured within the receiver 2010 by the guide and advancement structure 2072 prohibiting movement of the insert 1014 up and out through the receiver opening 2066 as well as by captured retainer 2012 located below the insert.

With further reference to FIG. 124, the pre-assembled receiver, insert and retainer are ready for shipping and also ready for attachment to the shank 2004. Such pre-assembly is placed above the shank upper portion 2008 until the shank upper portion is received within the opening 2110. With particular reference to FIGS. 125-128, as the shank upper portion 2008 is moved into the interior 2061 of the receiver base, the shank upper portion 2008 presses upwardly against the retainer 2012 in the receiver recess partially defined by the cylindrical surface 2098, as well as the cylindrical surfaces 2100 and 2101 as best shown in FIG. 125 (showing maximum expansion). The retainer 2012 is blocked from further upper movement by the outer tangs 2118 abutting against the ceiling surface 2096. With reference to FIG. 126, as the shank head 2008 continues to move upwardly toward the channel 2064, the shank head surface 2034 eventually abuts up against the insert 2014. However, the insert 1014 is prohibited from moving upward by the receiver guide and advancement structure 2072. Also with reference to FIG. 126 as well as FIG. 127, at this time, the shank head spherical surface 2034 at the ridges 2035 comes into gripping contact with the radiused surfaces 2129 of the retainer inner tangs 2117 and the retainer 2012 begins to return towards a neutral or nominal state as the center of the sphere of the shank head 2008 has passed beyond the retainer surface 2147. With reference to FIG. 128, the shank 2004 is shown in an initial stage of pull down, with the radiused surfaces 2129 fairly tightly gripping against the ridged surface portion 2035. With reference to FIG. 129, further pulling of the shank 2004 downwardly away from the receiver 2010, pulls the retainer 2116 past the receiver abutment edge 2105 and the retainer is then placed in a fully seated position with the retainer surfaces 2124 and 2125 fully abutting against and seating on the receiver surfaces 2102 and 2103. The radiused surfaces 2129 are still in frictional contact with the ridged surfaces 2035, providing a fairly tight friction fit between the head 2008 and the retainer 2012, the surface 2034 being pivotable with respect to the retainer 2012 with some force. Thus, a tight, non-floppy ball and socket joint is now created between the retainer 2012 and the shank upper portion 2008. Although still fully captured within the receiver, the outer tangs or panels 2118 are still only partially restrained with respect to the receiver, as a user is able to rotate the retainer about the receiver central axis prior to locking of the shank with respect to the receiver. Thus, at this time also, the retainer is fully seated on the receiver surfaces 2102 and 2103 and the surfaces 2116 and 2121 are pressed outwardly into abutting relationship with the receiver with the lower skirt 2121' spaced from the receiver flared surface 2107 and the retainer bottom surface 2122 in approximately the same plane as the receiver bottom surface 2108. With reference to FIG. 130, downward pressure of the shank head 2008 on the retainer edge 2147 further expands the retainer body 2115 outwardly, the retainer body formed in part by the lower skirt surfaces 2121 and 2121' advantageously allows for the head 2008 to seat lower within the receiver than in other known polyaxial bone anchors as well as lower than that shown in the assembly 1. The skirt feature 2121 and 2121' thus allows for a more stable lower seating surface in combination with the retainer cupped surface 2149 that allows for increased angular orientation of the shank with respect to the retainer, and thus with respect to the entire bone screw assembly, such an angular increase being possible without the need to provide a cut-out or cupped surface at and near the receiver bottom 2108. Also advantageous is the fact that the partially constrained retainer 2012 may be rotated with respect to the receiver 2010 about the receiver central axis, allowing for the user to choose the location of the increased angle of orientation between the receiver 2010 and the shank 2004.

With reference to FIG. 130, after the retainer 2012 is moved downwardly into the receiver 2010 and seated on the surfaces 2102 and 2103, the insert 2014 remains located spaced above the shank head 2008 as the receiver spring tabs 2078 and/or the receiver stepped surface 2094 prohibits downward movement of the insert 2014 unless a downward force is applied on the insert either by a tool or the rod 2021 and closure top 2018 shown in FIG. 130, for example and discussed previously herein with respect to the almost identical locking insert 14. At this time, prior to locking with a closure top, the receiver 2010 may be articulated to a desired angular position with respect to the shank 2004 (such as the angular orientations shown in FIGS. 133 and 134, for example), that will be held, but not locked, by the frictional engagement between the retainer 2012 inner panels 2117 and the shank upper portion 2008. As discussed above with respect to the assembly 1, at this time, the lock and release insert 2014 may be pressed into interference fit relationship with the receiver surfaces 2095 by a tool or by the closure top 2018 pressing down upon the rod 2021 that in turn presses down upon the insert 2014 as shown in FIG. 130. With reference to FIGS. 131 and 132, the closure top 2018 and the rod 2021 may be loosened or removed and the assembly 2001 may be outfitted with the deformable rod 2921' and cooperating closure top 2018' without unlocking the polyaxial mechanism, as previously described herein with respect to the assembly 1. The insert 2014 may also be unlocked, if desired, as described above with respect to the assembly 1.

With reference to FIGS. 133-134, different angular or articulated positions of the shank 2004 with respect to the receiver 2010 are shown, some making full use of the slit 2148 and adjacent cut-out or cupped surfaces 2149 of the retainer 2112. For example, in FIG. 134, the shank 2008 is pivoted toward and into engagement with the cupped surfaces 2149 (about thirty degree articulation) as compared to the arrangement shown in FIG. 133, wherein the shank 2004 is pivoted in a direction opposite to the retainer slit 2148 and the surfaces 2149 (about twenty degree articulation). An alternative receiver similar to the receiver 1010' previously described herein may also be used with the other components of the assembly 2001 to provide for additional degrees of angular articulation.

With reference to FIGS. 135-137, an alternative non-locking compression insert 2014' is illustrated for use with the shank 2004, receiver 2010, retainer 2012, closure top 2018 and rod 2021 previously described herein. The insert 2014' is substantially similar to the non-locking insert 214 previously described herein. During assembly with the receiver, the insert 2014' is rotated and the receiver holding tab surfaces 2084 slide along grooves 2070' until they spring into the apertures 2066' having bars 2067' that are the same or similar to the apertures and bars 267 previously described herein with respect to the insert 214. The bars 2067' holding the non-locking insert 2014' in place above the retainer 2012 until placed into locking engagement with the shank head 1008 by pressure from the rod 2021 and closure top 2018. It is noted that because of how the retainer 2012 is initially captured within the receiver cavity 2061, the bars 2067' may not be necessary, as a slight dropping of the insert 2014' would not cause accidental and unwanted early deployment of the retainer 2012 (as could possibly happen with the retainer 1012) as the retainer 2012 is already "deployed", i.e., the tangs 2118 are already in a neutral position within the receiver chamber during all of the assembly steps with both the insert 2014 and the shank 2004.

It is to be understood that while certain forms of the present invention have been illustrated and described herein, it is not to be limited to the specific forms or arrangement of parts described and shown.

The invention claimed is:

1. A pivotal bone anchor assembly configured for arrangement with a displacement tool prior to securement of an elongate rod to a bone of a patient via a closure, the pivotal bone anchor assembly comprising:
    a shank comprising a head and an anchor portion opposite the head configured for fixation to the bone;
    a receiver comprising a base defining an axial bore centered about a longitudinal axis and in communication with a bottom of the receiver through a bottom opening, and a pair of upright arms extending upwardly from the base to define an open channel configured for receiving the elongate rod, the axial bore extending upward through the open channel to a top of the receiver and having an interior insert-engaging surface, the receiver further including tool receiving structures configured for engagement by the displacement tool; and
    a compression insert configured for positioning into an initial position in the axial bore separate from the head of the shank being received in the axial bore, with the compression insert in the initial position being constrained from vertical movement along the longitudinal axis of the receiver by surface engagements between the axial bore and the compression insert;
    wherein after the head of the shank is received within the axial bore and prior to the elongate rod being securely locked in the open channel via the closure, the compression insert is configured for forced downward displacement within the axial bore by direct engagement with the displacement tool that is also engaged with the tool receiving structures of the receiver, the insert being configured for downwardly displacement from the initial position to a deployed position having an interference fit engagement against the interior insert-engaging surface of the axial bore, so as to inhibit the compression insert from moving back up within the axial bore.

2. The pivotal bone anchor assembly of claim 1, wherein the interior insert-engaging surface of the axial bore and the compression insert in the deployed position have a non-overlapping interference fit engagement with respect to each other.

3. The pivotal bone anchor assembly of claim 1, wherein the compression insert further comprises an upper saddle surface configured to engage the elongate rod.

4. The pivotal bone anchor assembly of claim 1, wherein the compression insert is configured to be top-loaded into the receiver.

5. The pivotal bone anchor assembly of claim 1, wherein the compression insert is configured to be positioned within the receiver axial bore prior to the head of the shank.

6. The pivotal bone anchor assembly of claim 1, wherein the compression insert is configured to be non-threadably rotated into its initial position within the receiver axial bore.

7. The pivotal bone anchor assembly of claim 1, wherein the compression insert further comprises a lateral protruding structure configured to engage the interior insert-engaging surface of the receiver in the interference fit engagement.

8. The pivotal bone anchor assembly of claim 1, further comprising a retainer configured to be positioned within the axial bore of the receiver so as to capture and hold the head of the shank therein.

9. The pivotal bone anchor assembly of claim 8, wherein the retainer is configured to be non-pivoting with respect to the receiver.

10. The pivotal bone anchor assembly of claim 8, wherein the retainer includes at least one of a slit or slot extending through a thickness thereof and configured to allow for an expansion of the retainer around the head of the shank upon an uploading of the head into the axial bore through the bottom opening.

11. The pivotal bone anchor assembly of claim 10, wherein the retainer is configured to be held in an expansion region of the axial bore prior to capturing the head of the shank.

12. The pivotal bone anchor assembly of claim 8, wherein the retainer is configured to be positioned within the axial bore of the receiver prior to the head of the shank.

13. The pivotal bone anchor assembly of claim 1, wherein the shank is cannulated along an entire length thereof from a distal tip of the anchor portion to a proximal end surface of the head.

14. The pivotal bone anchor assembly of claim 1, further comprising the closure and the elongate rod, and wherein the closure is configured to engage the elongate rod but without contacting the compression insert when the elongate rod is securely locked within the pivotal bone anchor assembly via the closure.

15. The pivotal bone anchor assembly of claim 1, further comprising the closure, and wherein the closure is configured to be mechanically engageable with the receiver to securely lock the elongate rod within the pivotal bone anchor assembly.

16. The pivotal bone anchor assembly of claim 15, wherein the mechanical engagement between the closure and the receiver further includes rotating the closure into engagement with the receiver.

17. The pivotal bone anchor assembly of claim 15, wherein the mechanical engagement between the closure and the receiver further comprises a threaded engagement selected from the group consisting of a square-shaped thread, a reverse angle thread, and a buttress thread.

\* \* \* \* \*